US009699544B2

(12) United States Patent
Song et al.

(10) Patent No.: US 9,699,544 B2
(45) Date of Patent: *Jul. 4, 2017

(54) TERMINAL AND CONTROL METHOD THEREOF

(71) Applicant: LG Electronics Inc., Seoul (KR)

(72) Inventors: Seungkyu Song, Seoul (KR); Seehyung Lee, Seoul (KR); Sangmo Park, Seoul (KR); Seonghyok Kim, Seoul (KR); Dongchul Jin, Seoul (KR); Hyunjin Kim, Seoul (KR); Gukchan Lim, Seoul (KR); Jinsu Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,702

(22) Filed: Jul. 9, 2015

(65) Prior Publication Data

US 2015/0312669 A1 Oct. 29, 2015

Related U.S. Application Data

(63) Continuation of application No. 13/536,065, filed on Jun. 28, 2012, now Pat. No. 9,089,270.

(30) Foreign Application Priority Data

| Jun. 29, 2011 | (KR) | 10-2011-0063728 |
| Sep. 9, 2011 | (KR) | 10-2011-0092211 |
| Nov. 21, 2011 | (KR) | 10-2011-0121306 |

(51) Int. Cl.
*H04M 1/66* (2006.01)
*H04R 1/10* (2006.01)
(Continued)

(52) U.S. Cl.
CPC ....... *H04R 1/1041* (2013.01); *A61B 5/02438* (2013.01); *A61B 5/0404* (2013.01);
(Continued)

(58) Field of Classification Search
CPC .............. A61B 5/02438; A61B 5/0404; A61B 5/0488; A61B 5/1172; A61B 5/165;
(Continued)

(56) References Cited

U.S. PATENT DOCUMENTS

| 6,485,416 B1 | 11/2002 | Platt et al. |
| 7,769,435 B2 | 8/2010 | Kuo et al. |

(Continued)

FOREIGN PATENT DOCUMENTS

| CN | 200960123 Y | 10/2007 |
| CN | 101540795 A | 9/2009 |

(Continued)

*Primary Examiner* — Timothy Pham
(74) *Attorney, Agent, or Firm* — Birch, Stewart, Kolasch & Birch, LLP

(57) ABSTRACT

A user terminal device, and a method of controlling a user terminal device are discussed. The user terminal device includes an ear accessory of the user terminal device including a first electrocardiogram (ECG) electrode contacted with an ear of a user, a second ECG electrode contacted with a hand of the user, and a first speaker configured to output an audio signal; a display; and a controller configured to display, on the display, bio information based on a first ECG signal from the first ECG electrode when the ear of the user is contacted with the first ECG electrode, and control an audio playback in response to a second ECG signal from the second ECG electrode when the hand of the user is contacted with the second ECG electrode.

16 Claims, 52 Drawing Sheets

(51) Int. Cl.

| | | |
|---|---|---|
| A61B 5/024 | (2006.01) | |
| A61B 5/0404 | (2006.01) | |
| A61B 5/0488 | (2006.01) | |
| A61B 5/1172 | (2016.01) | |
| A61B 5/16 | (2006.01) | |
| A61B 5/00 | (2006.01) | |
| H04M 1/05 | (2006.01) | |
| H04M 1/21 | (2006.01) | |
| H04M 1/725 | (2006.01) | |

(52) U.S. Cl.
CPC .......... *A61B 5/0488* (2013.01); *A61B 5/1172* (2013.01); *A61B 5/165* (2013.01); *A61B 5/6898* (2013.01); *A61B 5/7203* (2013.01); *H04M 1/05* (2013.01); *H04M 1/21* (2013.01); *H04M 1/72519* (2013.01); *H04M 1/72527* (2013.01); *A61B 5/7405* (2013.01); *H04M 2250/12* (2013.01)

(58) Field of Classification Search
CPC ...... A61B 5/6898; A61B 5/7203; H04M 1/05; H04M 1/21; H04M 1/72519; H04M 1/72527; H04M 2250/12
USPC ......................................... 455/411
See application file for complete search history.

(56) References Cited

U.S. PATENT DOCUMENTS

| | | | |
|---|---|---|---|
| 7,788,104 B2 | 8/2010 | Matsuo et al. | |
| 2001/0012201 A1 | 8/2001 | Fries et al. | |
| 2004/0147814 A1 | 7/2004 | Zancho et al. | |
| 2004/0152957 A1 | 8/2004 | Stivoric et al. | |
| 2005/0081847 A1 | 4/2005 | Lee et al. | |
| 2005/0239493 A1 | 10/2005 | Batkin et al. | |
| 2006/0004298 A1 | 1/2006 | Kennedy et al. | |
| 2006/0061468 A1 | 3/2006 | Ruha | |
| 2006/0166702 A1 | 7/2006 | Dietz et al. | |
| 2007/0244669 A1 | 10/2007 | Vogel et al. | |
| 2008/0027340 A1* | 1/2008 | Kuo | A61B 5/02405 600/509 |
| 2008/0146892 A1 | 6/2008 | LeBoeuf et al. | |
| 2008/0171945 A1* | 7/2008 | Dotter | A61B 5/024 600/514 |
| 2008/0274770 A1 | 11/2008 | Park et al. | |
| 2009/0023391 A1 | 1/2009 | Falck | |
| 2009/0326406 A1 | 12/2009 | Tan et al. | |
| 2010/0217100 A1* | 8/2010 | LeBoeuf | A61B 5/00 600/301 |
| 2010/0274144 A1* | 10/2010 | Hu | A61B 5/02405 600/500 |
| 2011/0015496 A1 | 1/2011 | Sherman et al. | |
| 2011/0065482 A1 | 3/2011 | Koide et al. | |
| 2011/0301435 A1 | 12/2011 | Albert et al. | |
| 2012/0116184 A1* | 5/2012 | Shieh | A61B 5/01 600/301 |

FOREIGN PATENT DOCUMENTS

| | | |
|---|---|---|
| CN | 102027734 A | 4/2011 |
| EP | 2 278 776 A1 | 1/2011 |
| JP | 2008-161641 A | 7/2008 |
| KR | 10-2003-0041387 A | 5/2003 |
| KR | 10-2006-0111159 A | 10/2006 |
| KR | 10-2010-0060795 A | 6/2010 |
| WO | WO 2011/040877 A1 | 4/2011 |

\* cited by examiner

TERMINAL AND CONTROL METHOD THEREOF

CROSS-REFERENCE TO RELATED APPLICATIONS

This application is a Continuation of co-pending U.S. application Ser. No. 13/536,065 filed on Jun. 28, 2012, which claims priority under 35 U.S.C. §119 and 35 U.S.C. §365 to Korean Patent Applications No. 10-2011-0063728 filed on Jun. 29, 2011, No. 10-2011-0092211 filed on Sep. 9, 2011, and No. 10-2011-0121306 filed on Nov. 21, 2011. The entire contents of all of the above applications are hereby incorporated by reference.

BACKGROUND OF THE INVENTION

Field of the Disclosure

The present disclosure relates to a terminal and a control method thereof.

Depending on whether a terminal can be moved, it is classified into a mobile/portable terminal and a stationary terminal. Again, the mobile/portable terminal is classified into a handheld terminal and a vehicle mount terminal, depending on whether a user can carry it personally.

Description of the Related Art

As such a terminal has diversified functions, it is implemented with a multimedia player form having complex functions such as capturing pictures or videos, playing music or video files, playing games, or receiving broadcasts.

In order to support and advance the functions of such a terminal, improving structural parts and/or software parts may be in consideration.

In general, in the case of a personal computer (PC), the size of a monitor is relatively large, and the performance of a central processing unit (CPU) is relatively high, so that various functions may be performed. In order to efficiently control such various functions, the PC includes diverse input devices such as a keyboard or a mouse.

Due to the advent of a mobile/portable terminal having a relatively large display unit and a high-performance CPU such as a touch-based mobile phone, e-book reader, smart pad, and tablet PC without a keypad, the mobile/portable terminal may perform various functions.

However, since the mobile/portable terminal does not have an external input device such as a keyboard or a mouse in many cases, various techniques are in search in order to easily control various functions thereof.

SUMMARY OF THE INVENTION

Embodiments provide a terminal for easily controlling various functions even if it does not include an external input device such as a keyboard or a mouse, and a control method thereof.

In one embodiment, a terminal includes: at least one body sensor; at least one wireless communication module; a display unit; a memory for storing a program that processes at least one body signal detected by the at least one body sensor; and a control unit for executing the memory.

The terminal may further include: a light emitting diode; and a light receiving diode for receiving the light emitted from the light emitting diode, wherein the at least one body sensor includes a blood movement measuring sensor for generating a blood movement measurement signal from the current that the light receiving diode provides.

The terminal may further include an ECG electrode, wherein the at least one body sensor includes an electrocardiogram (ECG) sensor for generating an ECG signal from the ECG electrode.

The memory may further store an ECG pattern; and the program may perform user authentication when an ECG waveform detected from the ECG signal and the ECG pattern of the user are identical from comparison.

The at least one wireless communication module may include a body communication module for demodulating a signal generated from the ECG electrode in order to generate demodulated data, and providing a signal modulated by modulating transmission data to the ECG electrode;

The terminal may further include a proximity sensor, wherein the ECG sensor starts to generate an ECG signal through the ECG electrode when the proximity of an object is detected through the proximity sensor during a phone call; the control unit may obtain an excitement of a user from the ECG signal; the control unit may end a call or may output an alarm when the excitement is more than a predetermined level; the proximity sensor may be disposed adjacent to the ECG electrode; and the ECG electrode may be disposed adjacent to a call speaker.

The ECG electrode may be disposed at an ear accessory; and the control unit may determine whether to output an audio signal to an ear speaker of the ear accessory on the basis of an ECG signal recognized through the ECG electrode.

The terminal may further include a hand contact ECG electrode, wherein the hand contact ECG electrode is disposed at the ear accessory or the terminal; and the control unit performs an operation related to audio playback or call reception on the basis of an ECG signal recognized through the hand contact ECG electrode.

The details of one or more embodiments are set forth in the accompanying drawings and the description below. Other features will be apparent from the description and drawings, and from the claims.

DETAILED DESCRIPTION OF THE EMBODIMENTS

Hereinafter, a portable terminal according to the present invention will be described in more detail with reference to the accompanying drawings. The suffix "module" and "unit" for components, which used in the description below, is assigned and mixed in consideration of only easiness in writing the specification. That is, the suffix itself does not have different meanings or roles.

A portable terminal described in this specification may include a mobile phone, a smart phone, a laptop computer, a digital broadcast terminal, a Personal Digital Assistant (PDA), a Portable Multimedia Player (PMP), and a GPS navigation system. However, it is apparent to those skilled in the art that a configuration according to embodiments of the present invention may be applicable to a stationary terminal such as a digital TV and a desktop computer, besides a portable terminal.

A structure of a portable terminal according to an embodiment will be described below with reference to FIG. 1.

Figure 1:
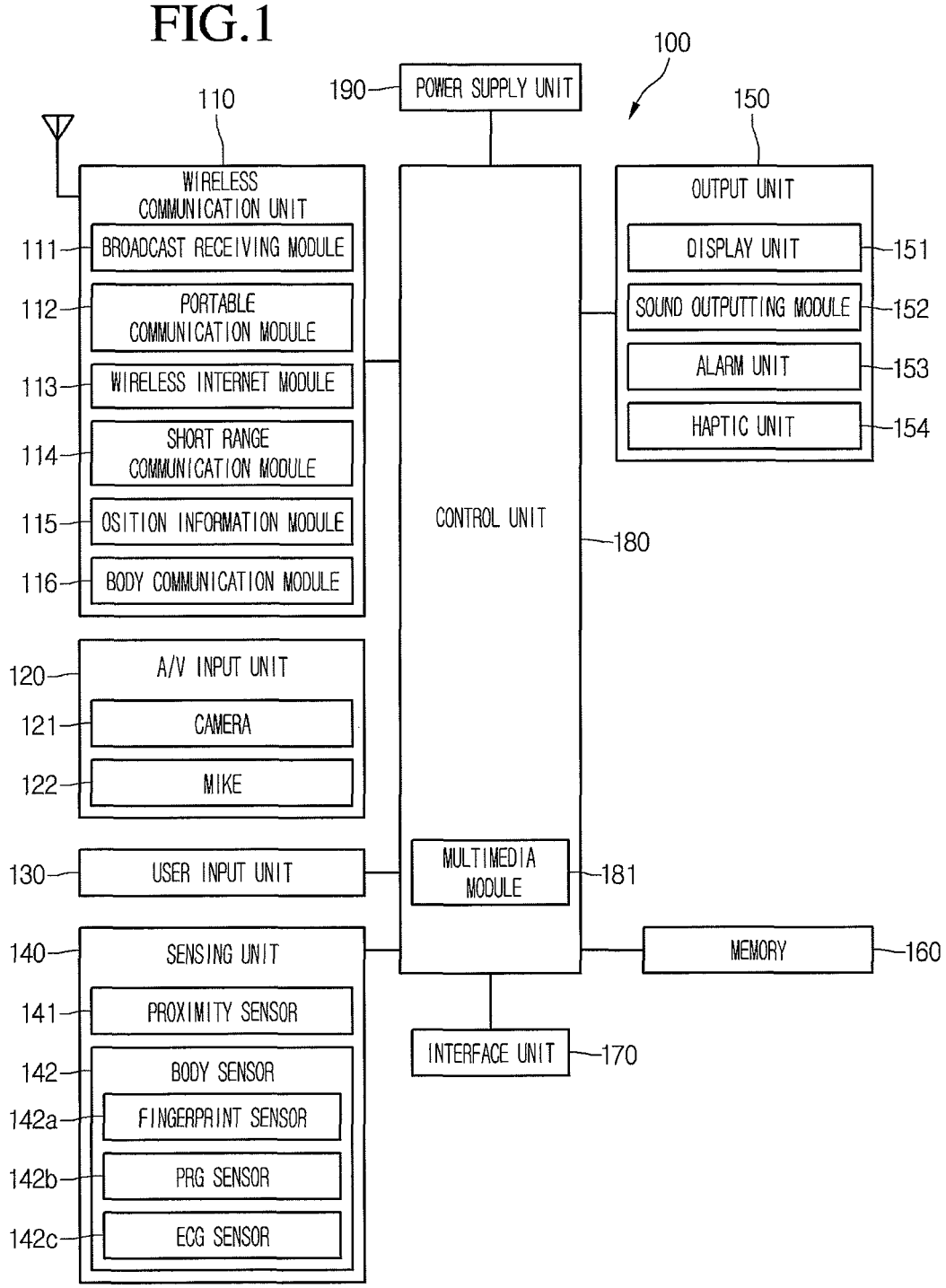
FIG. 1 is a block diagram of a portable terminal according to an embodiment.

FIG. 1 is a block diagram of a portable terminal according to an embodiment.

The portable terminal 100 includes a wireless communication unit 110, an Audio/Video (A/V) input unit 120, a user input unit 130, a sensing unit 140, an output unit 150, a memory 160, an interface unit 170, a control unit 180, and a power supply unit 190. Since the portable terminal 100 is not limited to the components shown in FIG. 1, it may be implemented with more or less components.

Hereinafter, the components will be described sequentially.

The wireless communication unit 110 may include at least one module that allows wireless communication between the portable terminal 100 and a wireless communication system or between the portable terminal 100 and a network that the portable terminal 100 belongs. For example, the wireless communication unit 110 may include a broadcast receive module 111, a mobile communication module 112, a wireless internet module 113, a short range communication module 114, a position information module 115, and a body communication module 116.

The broadcast receive module 111 receives a broadcast signal and/or broadcast related information from an external broadcast management server through a broadcast channel.

The broadcast channel may include a satellite channel a terrestrial channel. The broadcast management server may refer to a server that generates and transmits a broadcast signal and/or broadcast related information or a server that receives a pre-generated broadcast signal and/or broadcast related information and transmits it/them to a terminal. The broadcast signal may include a broadcast signal in the combination form of a data broadcast signal and a TV broadcast signal or a radio broadcast signal, in addition to a TV broadcast signal, a radio broadcast signal, and a data broadcast signal.

The broadcast related information may refer to information on a broadcast channel, a broadcast program, or a broadcast service provider. The broadcast related information may be provided through a mobile communication network. In this case, the broadcast related information may be received by the mobile communication module 112.

The broadcast related information may exist in various forms. For example, the broadcast related information may be in forms such as Electronic Program Guide (EPG) of DMB (Digital Multimedia Broadcasting) or Electronic Service Guide (ESG) of DVB-H (Digital Video Broadcast-Handheld (DVB-H).

The broadcast receiving module 111 may receive a digital broadcast signal by using a digital broadcast system such as Digital Multimedia Broadcasting-Terrestrial (DMB-T), Digital Multimedia Broadcasting-Satellite (DMB-S), Media Forward Link Only (MediaFLO), Digital Video Broadcast-Handheld (DVB-H), and Integrated Services Digital Broadcast-Terrestrial (ISDB-T). Of course, the broadcast receiving module 111 may be configured to be appropriate for the digital broadcast system and other broadcast systems.

A broadcast signal and/or broadcast related information received through the broadcast receiving module 111 may be stored in the memory 160.

The mobile communication module 112 transmits/receives a wireless signal to/from at least one of a base station, an external terminal, and a server on a mobile communication network. The wireless signal may include various forms of data according to a voice call signal, video call signal, or character/multimedia message transmission.

The wireless internet module 113 refers to a module for wireless internet access, and may be embedded in or externally mounted on the portable terminal 100. A wireless internet technique includes Wireless LAN (WLAN), i.e. Wi-Fi, Wireless broadband (Wibro), World Interoperability for Microwave Access (Wimax), and High Speed Downlink Packet Access (HSDPA).

The short range communication module 114 refers to a module for short range communication. A short range communication technique includes Bluetooth, Radio Frequency Identification (RFID), infrared Data Association (IrDA), Ultra Wideband (UWB), and ZigBee.

The position information module 115 is a module for obtaining the position of a portable terminal, and its representative example includes a Global Position System (GPS).

The body communication module 116 outputs a modulated signal to an electrode that contacts the body after modulating the received data from the control unit 180 in order for body communication. Additionally, the body communication module 116 demodulates the received signal from the electrode that contacts the body in order for body communication, and then, delivers the demodulated data to the control unit 180. The modulation for body communication may be Frequency Modulation (FM). The demodulation for body communication may be demodulation corresponding to the FM.

Referring to FIG. 1, the A/V input unit 120 is used for an audio signal or video signal input, and may include a camera 121 and a mike 122. The camera 121 processes an image frame of a still image or a moving image obtained by an image sensor during a video call mode or a capture mode. The processed image frame may be displayed on a display unit 151.

The image frame processed in the camera 121 may be stored in the memory 160 or transmitted to an external through the wireless communication unit 110. At least two cameras 121 may be equipped depending ton a usage environment.

The mike 122 receives an external sound signal through a microphone during a call mode, a recording mode, or a voice recognition mode, and then, processes the received signal as electrical voice data. In the case of a call mode, the processed voice data may be converted into a format available for transmission to a mobile communication base station by using the mobile communication module 112, and then, may be outputted. Various noise canceling algorithms may be implemented in the mike 122 in order to cancel the noise occurring while an external sound signal is received.

The user input unit 130 generates input data for an operation control of a terminal by a user. The user input unit 130 may include a key pad, a dome switch, a touch pad (resistive/capacitive), a jog wheel, and a jog switch.

The sensing unit 140 generates a sensing signal for controlling an operation of the portable terminal 100 by sensing a current state of the portable terminal 100 such as the close/open state of the portable terminal 100, the position of the portable terminal 100, the user contact of the portable terminal 100, the orientation of the portable terminal 100, and the acceleration/deceleration of the portable terminal 100. For example, if the portable terminal 100 is the form of a slide phone, the sensing unit 140 senses whether the slide phone is opened/closed. Additionally, the sensing unit 140 senses whether the power supply unit 190 supplies power or whether the interface unit 170 is combined with an external device. Moreover, the sensing unit 140 may include a proximity sensor 141 and a body sensor 142.

The body sensor 142 may include a finger print sensor 142a, a photoplethysmographic (PPG) signal sensor 142b, and an Electrocardiogram (ECG) sensor 142c.

The fingerprint sensor 142a generates fingerprint recognition information from a signal of a fingerprint recognition electrode. The fingerprint sensor 142a may or may not include a fingerprint recognition electrode conceptually.

The PPG sensor 142b generates a blood movement measurement signal from the current that is provided from a light receiving diode that receives the light emitted from a light emitting diode. The PPG sensor 142b may or may not include a light emitting diode and a light receiving diode conceptually.

The ECG sensor 142c generates an ECG signal from a signal of an ECG electrode. The ECG sensor 142c may or may not include an ECG electrode conceptually.

The output unit 150 generates a visual, auditory or tactile output, and includes a display unit 151, a sound outputting module 152, an alarm unit 153, and a haptic module 154.

The display unit 151 displays (outputs) information processed by the portable terminal 100. For example, when a portable terminal is in a call mode, the display unit 151 displays call related User Interface (UI) or Graphic User Interface (GUI). When the portable terminal 100 is in a video call mode or a capture mode, the display unit 100 displays a captured or/and received image, UI, and GUI.

The display unit 151 includes at least one of a liquid crystal display (LCD), a thin film transistor-liquid crystal display (TFT LCD), an organic light-emitting diode (OLED), a flexible display, and a 3D display.

Some displays may be configured with a transparent type or a light transmission type in order to see an external through them. This may be called a transparent display, and its representative example is a Transparent OLED (TOLED). The display unit 151 may be configured with a rear structure or a light transmission type structure. According to such a structure, a user may see an object at the rear of a terminal body through an area that the display unit 151 of the terminal body occupies.

At least two display units 151 may be provided according to an implementation form of the portable terminal 100. For example, a plurality of display units may be spaced from each other on one side, may be integrally disposed on one side, or may be disposed at different sides, respectively.

When the display unit 151 and a touch operation sensing sensor (hereinafter, referred to as a touch sensor) have a mutual layer structure (hereinafter, referred to as a touch screen), it may serve as an input device in addition to an output device. A touch sensor may have a form such as a touch film, a touch sheet, and a touch pad.

The touch sensor may be configured to convert a change of a pressure applied to a specific portion of the display unit 151 or a change of a capacitance occurring at a specific portion of the display unit 151 into an electrical input signal. The touch sensor may be configured to detect a pressure during touching in addition to a touched position and area.

If a touch input is provided for a touch sensor, signal(s) corresponding thereto is(are) transmitted to a touch controller. The touch controller processes the signal(s) and then transmits corresponding data to the control unit 180. By doing so, the control unit 180 recognizes which area of the display unit 151 is touched.

Referring to FIG. 1, the proximity sensor 141 may be disposed in an inner area of a portable terminal surrounded by the touch screen or near the touch screen. The proximity sensor 141 is a sensor for detecting an object that approaches a predetermined detection side or an object that exists near the proximity sensor 141, by using electromagnetic force or infrared without mechanical contact. The proximity sensor 141 has a longer lifecycle and a higher utilization than a contact type sensor.

The proximity sensor 141 may include a transmission type photoelectric sensor, a direct reflection type photoelectric sensor, a mirror reflection type photoelectric sensor, a high frequency oscillation type proximity sensor, a capacitance type proximity sensor, a magnetic type proximity sensor, and an infrared proximity sensor. If the touch screen is a capacitive type, it is configured to detect the proximity of the pointer by using the change in an electric field according to the proximity of the pointer. In this case, the touch screen (i.e., a touch sensor) may be classified as a proximity sensor.

For convenience of description, an action for recognizing that the pointer is positioned on the touch screen is called "proximity touch", and an action that a pointer actually contacts the touch screen is called "contact touch". The position where a pointer contacts the touch screen through proximity touch means that the pointer contacts the touch screen vertically through proximity touch.

The proximity sensor detects proximity touch and a proximity touch pattern (for example, proximity touch distance, proximity touch direction, proximity touch speed, proximity touch time, proximity touch position, and proximity touch moving state). Information on the detected proximity touch operation and proximity touch pattern may be outputted on a screen.

The audio output module 152 may output audio data received from the wireless communication unit 110 or stored in the memory 160 during call signal reception, a call mode, a recording mode, a voice recognition mode, or a broadcast receiving mode. The sound outputting module 152 outputs a sound signal, which is related to a function of the portable terminal 100 (for example, a call signal incoming sound and a message incoming sound). The sound outputting module 152 may include a receiver, a speaker, and a buzzer.

The alarm unit 153 outputs a signal notifying an event occurrence of the portable terminal 100. Examples of the event occurring in the portable terminal 100 includes call signal reception, message reception, key signal input, and touch input. The alarm unit 153 may output a signal notifying event occurrence through vibration in addition to a video signal or an audio signal. Since the video signal or the audio signal may be outputted through the display unit 151 or the sound outputting module 152, they 151 and 152 may be classified as part of the alarm unit 153.

The haptic module 154 generates various haptic effects that a user can feel. A representative example of a haptic effect that the haptic module 154 generates includes vibration. The intensity and pattern of vibration that the haptic module 154 generates is controllable. For example, different vibrations are combined and outputted or are sequentially outputted.

The haptic module 154 may generate various haptic effects such as pin arrangement that vertically moves with respect to a skin contact surface, injection or suction power of air through an injection inlet or a suction inlet, rubbing for skin surface, electrode contact, an effect by stimuli such as electrostatic force, and an effect by cold/warm sense reproduction using a device that suctions or emits heat, in addition to the vibration.

The haptic module 154 may be implemented to deliver a haptic effect through direct contact and also allows a user to feel a haptic effect through a muscle sense of a finger or an arm. At least two haptic modules 154 may be equipped according to a configuration aspect of the portable terminal 100.

The memory 160 may store a program for an operation of the control unit 180, and may temporarily store input/output data (for example, a phone book, a message, a still image, and, a moving image. The memory 160 may store data regarding the vibrations and sounds of various patterns, which are outputted during touch input on the touch screen.

The memory 160 may include at least one storage medium of a flash memory type, a hard disk type, a multimedia card micro type, a card type memory (for example, SD or XD memory), Random Access Memory (RAM), Static Random Access Memory (SRAM), Read-Only Memory (ROM), Electrically Erasable Programmable Read-Only Memory (EEPROM), Programmable Read-Only Memory (PROM), magnetic memory, magnetic disk, and optical disk. The portable terminal 100 may operate in relation to a web storage that performs a storage function of the memory 160 on internet.

The interface unit 170 serves as a path to all external devices connected to the portable terminal 100. The interface unit 170 receives data from an external device or power to deliver it to each component in the portable terminal 100, or transmits data in the portable terminal 100 to an external device For example, the interface unit 170 may include a wire/wireless headset port, an external charging port, a memory card port, a port for connecting to a device having an identification module, an audio Input/Output (I/O) port, a video I/O port, and an earphone jack.

The identification module is a chip for storing various information to certify the usage permission of the portable terminal 100, and may include User Identify Module (UIM), Subscriber Identity Module (SIM), and Universal Subscriber Identity Module (USIM). A device having an identification module (hereinafter, referred to as an identification device) may be manufactured with a smart card type. Accordingly, the identification device may be connected to the portable terminal 100 through a port.

When the portable terminal 100 is connected to an external cradle, the interface unit may serve as a path through which power from the cradle is supplied to the portable terminal 100, or a path through which various command signals inputted from the cradle is delivered to the portable terminal 100. The various command signals or power inputted from the cradle may operate as a signal that recognizes that the portable terminal 100 is properly mounted on the cradle.

The control unit 180 generally controls overall operations of the portable terminal 100. For example, the control unit 180 controls and processes operations related to voice call, data communication, and video call. The control unit 180 may include a multimedia module 181 for playing multimedia. The multimedia module 181 may be implemented in the control unit 180, and may be implemented, being separated from the control unit 180.

The control unit 180 may perform a pattern recognition process for recognizing handwriting input and picture drawing input on the touch screen as a character and an image, respectively.

The power supply unit 190 receives external power and internal power according to a control of the control unit 180, and then, supplies power necessary for an operation of each component.

Various embodiments described herein may be implemented using a computer or similar device thereto readable medium through software, hardware or a combination thereof.

In terms of hardware implementation, embodiments described herein may be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electric units for performing other functions. In some cases, embodiments may be implemented by the control unit 180.

In terms of software implementation, embodiments related to a procedure or function may be implemented with an additional software module for performing at least one function or operation. A software code may be implemented by a software application written using a proper program language. The software code is stored in the memory 160, and is executed by the control unit 180.

The external appearance of a portable terminal according to an embodiment will be described with reference to FIGS. 2 to 9.

Figure 2:
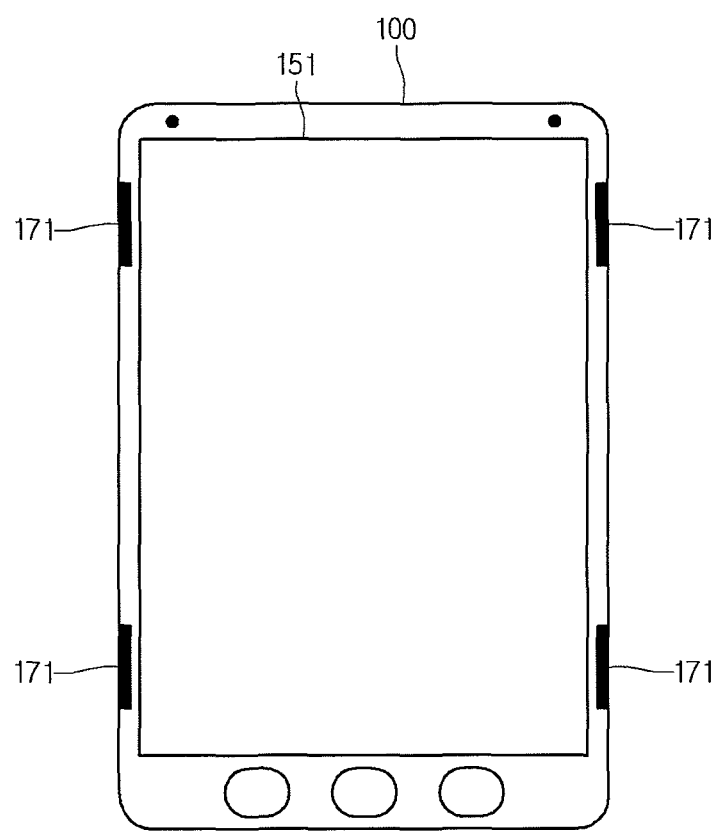
FIG. 2 is a front view of a portable terminal according to an embodiment.

FIG. 2 is a front view of a portable terminal according to an embodiment.

As shown in FIG. 2, the portable terminal 100 includes a display unit 151 at the front and four ECG electrodes 171. The four ECG electrodes 171 are disposed at the top and bottom of the left bezel and the top and bottom of the right bezel of the portable terminal 100. In various embodiments, the number of electrodes and their positions may vary.

Figure 3:
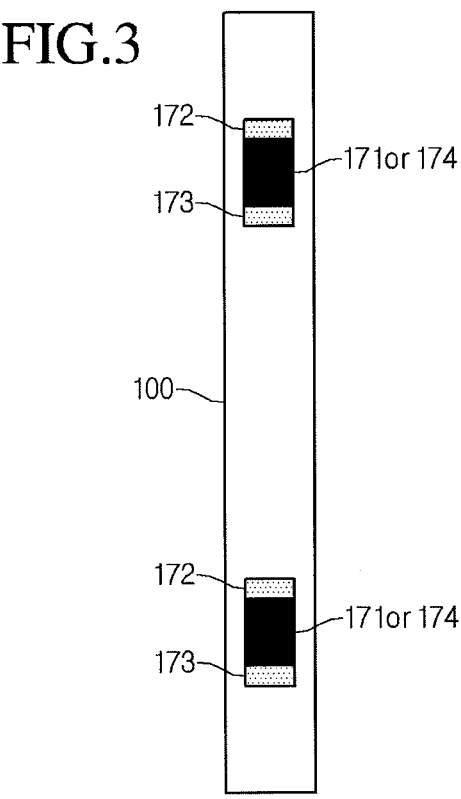
FIG. 3 is a right side view of a portable terminal according to an embodiment.

FIG. 3 is a right side view of a portable terminal according to an embodiment.

As shown in FIG. 3, the portable terminal 100 includes two ECG electrodes 171 at the right bezel. Each of the light emitting diode 172 and the light receiving diode 173 for the PPG sensor 142b may be disposed adjacent to the ECG electrode 171. Thereby, ECG measurement and blood movement measurement are possible at the same time.

Moreover, the portable terminal 100 includes two fingerprint recognition electrodes 174 instead of the two ECG electrodes 171 at the right bezel. The light emitting diode 172 and the light receiving diode 173 for the PPG sensor 142b may be disposed adjacent to each of the ECG electrodes 174. Thereby, fingerprint measurement and blood movement measurement are possible at the same time.

In FIG. 3, the number of the ECG electrodes 171 and their positions, the number of the light emitting diodes 172 and their position, the number of the light receiving diodes 173 and their positions, and the number of the fingerprint electrodes 174 and their positions may vary.

Figure 4:
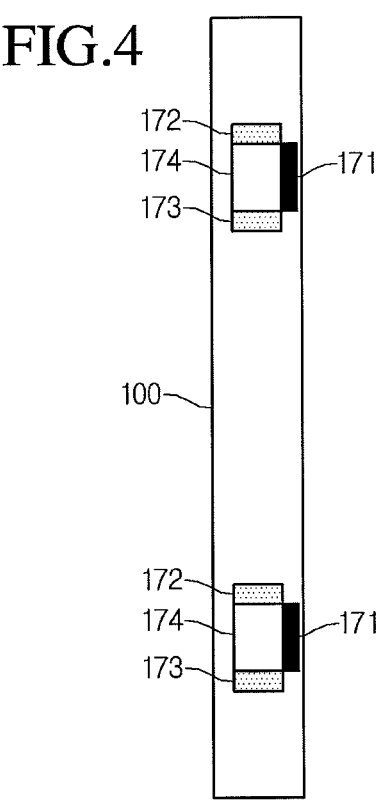
FIG. 4 is a right side view of a portable terminal according to an embodiment.

FIG. 4 is a right side view of a portable terminal according to an embodiment.

As shown in FIG. 4, the portable terminal 100 includes two fingerprint recognition electrodes 174 at the right bezel. The light emitting diode 172 and the light receiving diode 173 for the PPG sensor 142b may be disposed adjacent to each of the fingerprint recognition electrodes 174. Additionally, the ECG electrode 171 may be disposed adjacent to each of the fingerprint recognition electrodes 174. Thereby, fingerprint measurement and blood movement measurement are possible at the same time.

In FIG. 4, the number of the ECG electrodes 171 and their positions, the number of the light emitting diodes 172 and their position, the number of the light receiving diodes 173 and their positions, and the number of the fingerprint electrodes 174 and their positions may vary.

Figure 5:
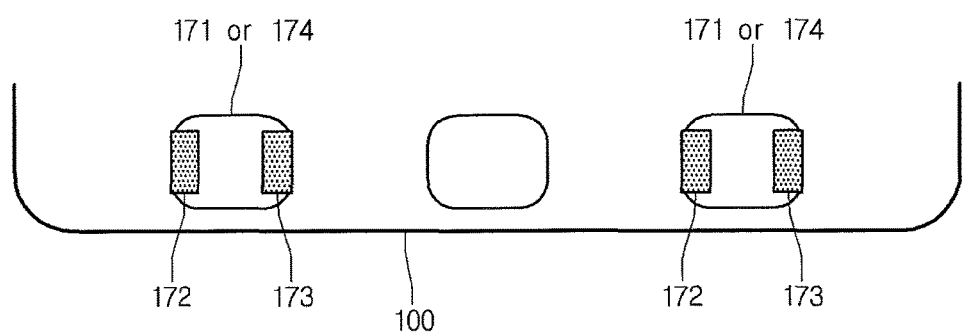
FIG. 5 is view illustrating the front bottom of a portable terminal according to an embodiment.

FIG. 5 is a view illustrating the front bottom of a portable terminal according to an embodiment.

As shown in FIG. 5, the portable terminal 100 includes two ECG electrodes 171 at the front bottom. Each of the light emitting diode 172 and the light receiving diode 173 for the PPG sensor 142b may be disposed adjacent to the ECG electrode 171. Thereby, ECG measurement and blood movement measurement are possible at the same time.

Moreover, the portable terminal 100 includes two fingerprint recognition electrodes 174 instead of the two ECG electrodes 171 at the front bottom. The light emitting diode 172 and the light receiving diode 173 for the PPG sensor 142b may be disposed adjacent to each of the fingerprint recognition electrodes 174. Thereby, fingerprint measurement and blood movement measurement are possible at the same time.

In FIG. 5, the number of the ECG electrodes 171 and their positions, the number of the light emitting diodes 172 and their position, the number of the light receiving diodes 173 and their positions, and the number of the fingerprint electrodes 174 and their positions may vary.

Figure 6:
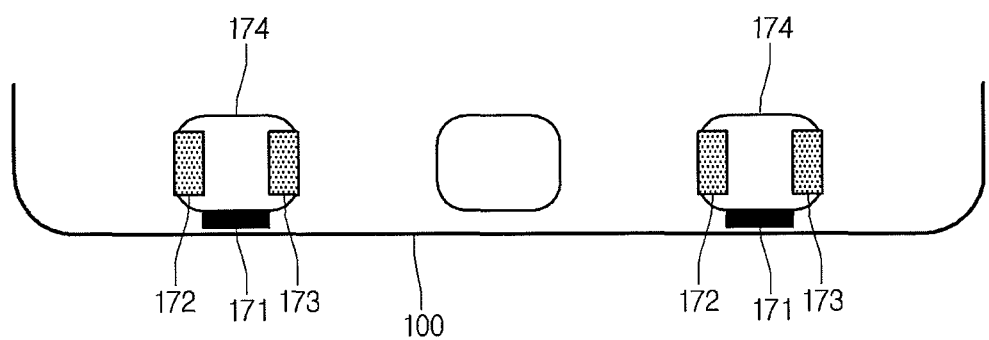
FIG. 6 is view illustrating the front bottom of a portable terminal according to an embodiment.

FIG. 6 is a view illustrating the front bottom of a portable terminal according to an embodiment.

As shown in FIG. 6, the portable terminal 100 includes two fingerprint recognition electrodes 174 at the right bezel. The light emitting diode 172 and the light receiving diode 173 for the PPG sensor 142b may be disposed adjacent to each of the fingerprint recognition electrodes 174. Additionally, the ECG electrode 171 may be disposed adjacent to each of the fingerprint recognition electrodes 174. Thereby, fingerprint measurement and blood movement measurement are possible at the same time.

In FIG. 6, the number of the ECG electrodes 171 and their positions, the number of the light emitting diodes 172 and their position, the number of the light receiving diodes 173 and their positions, and the number of the fingerprint electrodes 174 and their positions may vary.

In FIGS. 3 to 6, the ECG electrode 171 or the fingerprint recognition electrode 174 may be disposed at a function button such as a power button, a home button, an event obtaining button, and a next event period playing button. Here, the event obtaining button may correspond to a recording button or a picture capturing button. The next event period playing button may correspond to a next image displaying button, a next page displaying button, a next music playing button, or a next video period playing button.

Figure 7:
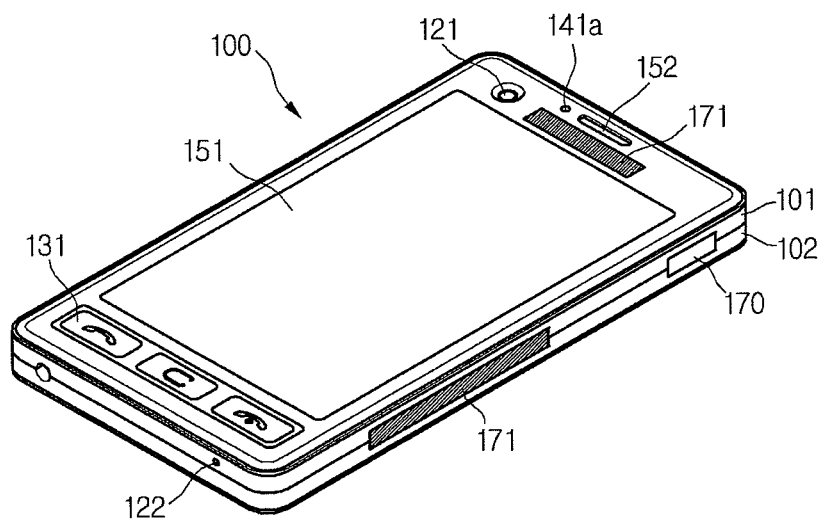
FIG. 7 is a front perspective view of a portable terminal according to an embodiment.

FIG. 7 is a front perspective view of a portable terminal according to an embodiment.

Referring to FIG. 7, the portable terminal 100 may have a bar-shaped body. However, the present invention is not limited thereto, and thus may be applicable to various structures such as a slide type, a folder type, a swing type, and a swivel type, where at least two bodies are combined for relative movement.

Bodies 101 and 102 include a case (for example, casing, housing, and cover) constituting the outer appearance. In this embodiment, the case may be divided into the front case 101 and the rear case 102. Various electronic components are embedded in a space between the front case 101 and the rear case 102. At least one middle case may be additionally disposed between the front case 101 and the rear case 102.

The cases may be formed by injecting synthetic resins or may be formed of metallic materials such as stainless steel (STS) or titanium (Ti).

The bodies 101 and 102 of the portable terminal 100 may include a display module 151, a sound outputting module 152, a camera 121, a user input unit 130, a mike 122, and an interface 170.

The display module 151 occupies a great part of the main surface of the front case 101. The sound outputting module 152 and the camera 121 are disposed at an area adjacent to one end of the both ends of the display module 151, and the user input unit 130 and the mike 122 are disposed at an area adjacent to the other end.

The user input unit 130 and the interface 170 may be disposed at the sides of the front case 101 and the rear case 102.

The user input unit 130 may be manipulated in order to receive a command for controlling an operation of the portable terminal 100.

The user input unit 130 may be called a manipulating portion, and may include a key button 131. The user input unit 130 may be in a tactile manner through which a user manipulates it with tactile sense.

Additionally, according to an embodiment of the present invention, the proximity sensor 141, and the plurality of ECG electrodes may be disposed at the bodies 101 and 102 of the portable terminal 100.

The proximity sensor 141 is disposed at the front of the portable terminal 100 in order to detect an object that approaches a specific position of the body. For example, the proximity sensor 141 is disposed adjacent to the sound outputting module 152 that operates as a speaker outputting a call sound during a call mode and the ECG electrode 171 used for sensing ECG, so that whether the head of user approaches the sound outputting module 152 is sensed during a call mode.

Additionally, one of the plurality of ECG electrodes 171 may be disposed adjacent to the sound outputting module 152 at the front of the portable terminal 100, and another may be disposed at the side of the portable terminal 100. When one of the plurality of ECG electrodes 171 is disposed at the side of the portable terminal 100, it may be disposed at the side of the front case 101, the side of the rear case 102, or the sides of the front case 101 and the rear case 102.

The ECG electrode 171 disposed at the front of the portable terminal 100 may be used to sense an ECG signal of a user, contacting the ear or head of a user during a call.

The ECG electrode 171 disposed at the side of the portable terminal 100 may be used to sense an ECG signal of a user, contacting the hand of a user during a call.

The plurality of ECG electrode 171 may be disposed at a position where it can easily contact the skin surface of a user while the user makes a call using the portable terminal 100 or manipulates the portable terminal 100.

Figure 8:
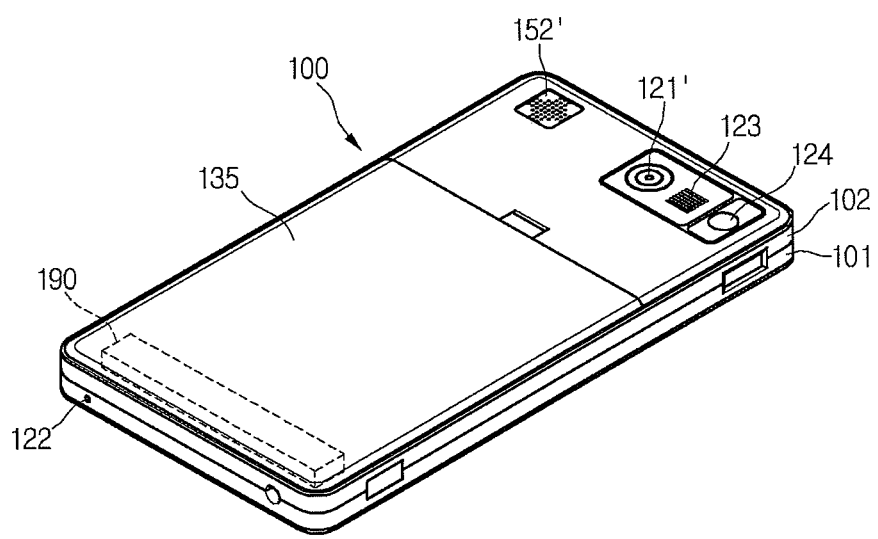
FIG. 8 is a rear perspective view of a portable terminal according to an embodiment.

FIG. 8 is a rear perspective view of a portable terminal according to an embodiment.

Referring to FIG. 8, a camera 121' may be additionally mounted at the body rear of the portable terminal 100, i.e. the rear case 102. The camera 121' substantially may have an opposite capturing direction to the camera 121 of FIG. 2, and may have different pixels than the camera 121.

For example, the camera 121 may have low pixels in order to capture the face of a user and than transmit the captured face image to the other party without difficulties, and the camera 121' may have high pixels in order to capture a general object without the need for transmission. The cameras 121 and 121' may be installed at the terminal body in order to make rotation and popup possible.

A flash 123 and a mirror 124 may be additionally disposed adjacent to the camera 121'. The flash 123 emits light toward an object when the camera 121' captures the object. The mirror 124 may be used in order that a user looks at himself/herself when the user captures himself/herself (self-shooting) by using the camera 121'.

A sound outputting module 152' may be additionally disposed at the body rear of the portable terminal 100. The sound outputting module 152' may perform a stereo function together with the sound outputting module 152 of FIG. 2, and also may be used for implementing a speaker phone mode during a call.

A broadcast signal receiving antenna 124 may be additionally disposed at the body side of the portable terminal 100, in addition to an antenna for a call. The antenna 124 constituting part of the broadcast receiving module 111 of FIG. 1 may be installed to be drawn from the terminal body.

The power supply unit 190 is mounted at the body of the portable terminal 100 in order to supply power to the portable terminal 100. The power supply unit 190 may be embedded in the portable terminal 100, or may be installed to be detachable from the external body of the portable terminal 100.

Figure 9:
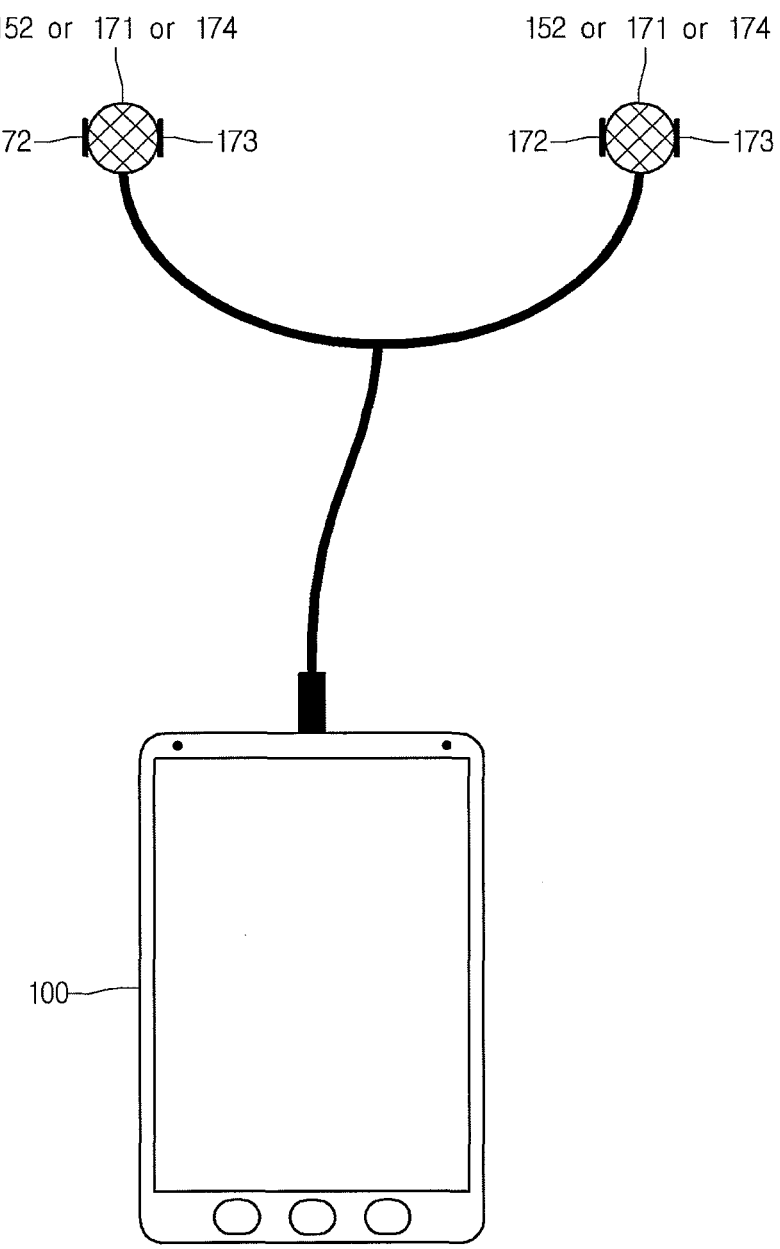
FIG. 9 is view illustrating a body sensing accessory connected to a portable terminal according to an embodiment.

FIG. 9 is a view illustrating a body sensing accessory connected to a portable terminal according to an embodiment.

The body sensing accessory shown in FIG. 9 may be connected to the earphone jack 176 of the portable terminal 100. Especially, the body sensing accessory shown in FIG. 9 may be an earphone or the headset connected to the earphone jack 176 of the portable terminal 100. As shown in FIG. 9, the body sensing accessory may include two sound outputting modules 152. The light emitting diode 172 and the light receiving diode 173 for the PPG sensor 142b may be disposed adjacent to each of the sound outputting modules 152. By doing so, even if the portable terminal 100 does not provide a blood movement measurement function, a user may measure a blood movement, while listening to music.

Moreover, the body sensing accessory may include the two ECG electrodes 171 instead of the two sound outputting module 152. Each of the light emitting diode 172 and the light receiving diode 173 for the PPG sensor 142b may be disposed adjacent to the ECG electrode 171. By doing so, even if the portable terminal 100 does not provide an ECG measurement function and a blood movement measurement function, a user may measure an ECG and a blood movement at the same time.

Moreover, the body sensing accessory may include the two fingerprint recognition electrodes 174 instead of the two sound outputting modules 152. The light emitting diode 172 and the light receiving diode 173 for the PPG sensor 142b may be disposed adjacent to each of the fingerprint recognition electrodes 174. By doing so, even if the portable terminal 100 does not provide a fingerprint measurement function and a blood movement measurement function, a user may measure a fingerprint and a blood movement at the same time.

Figure 10:
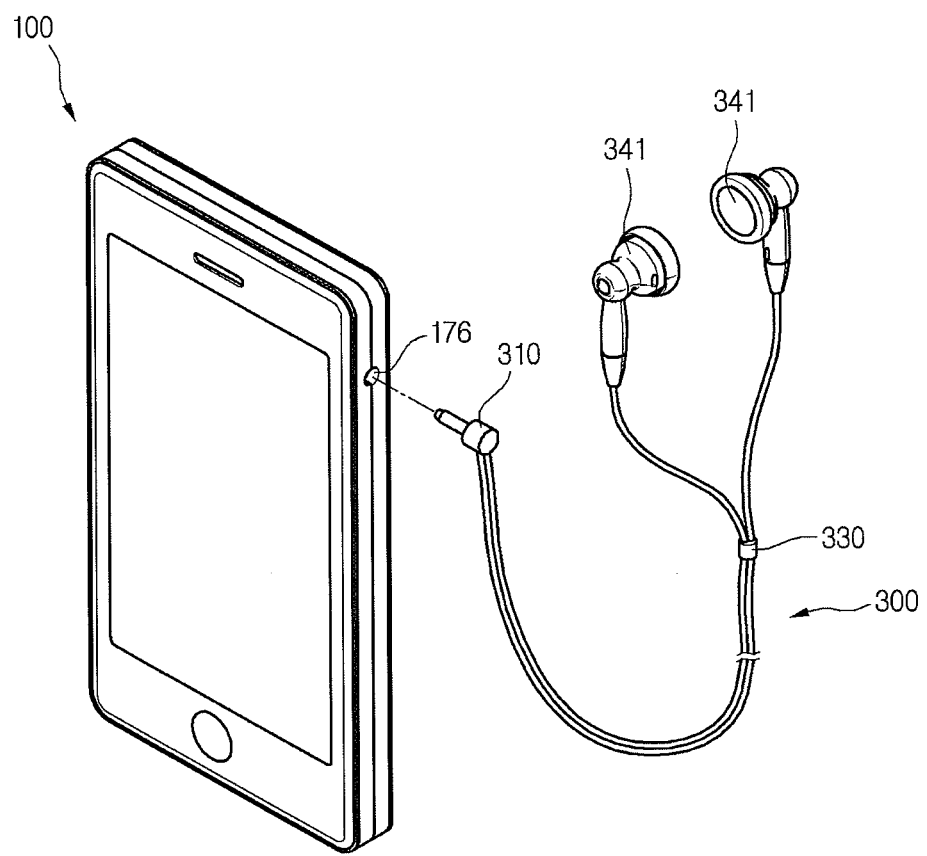
FIG. 10 is schematic view of a portable terminal having an earphone connected according to an embodiment.

FIG. 10 is schematic view of a portable terminal having an earphone connected according to an embodiment.

Referring to FIG. 10, the earphone 300 may be detachable to the main body of the portable terminal 100 through the earphone jack 176.

The main body of the portable terminal 100 may have various types such as a slide type and a folder type. The main body of the portable terminal 100 is equipped with the earphone jack 176 from which the earphone 300 is detachable. The earphone jack 176 may include a predetermined number of connection terminals.

For example, if the earphone 300 is a 4-pole earphone, it includes a mike 300 for collecting a sound signal of a user in order to support Push To Talk (PTT) service, and accordingly, one of the connection terminals of the earphone jack 176 may include a mike terminal to deliver the user sound signal, collected by the mike 330, into the portable terminal 100.

Moreover, the earphone 300 may further include a plurality of ECG electrodes 341 in order to obtain an ECG signal of a user. When a user plugs the earphone 300 in the ears, electrodes 341 may be disposed at the main body of the earphone 300 in order to contact the skin surface of the user and sense an ECG signal.

Furthermore, if the earphone 300 includes a plurality of ECG electrodes 341 for sensing an ECG signal, the earphone jack 176 may further include a terminal for delivering ECG signals, collected by the plurality of ECG electrodes 341 for sensing an ECG signal, to the portable terminal 100.

Figure 11:
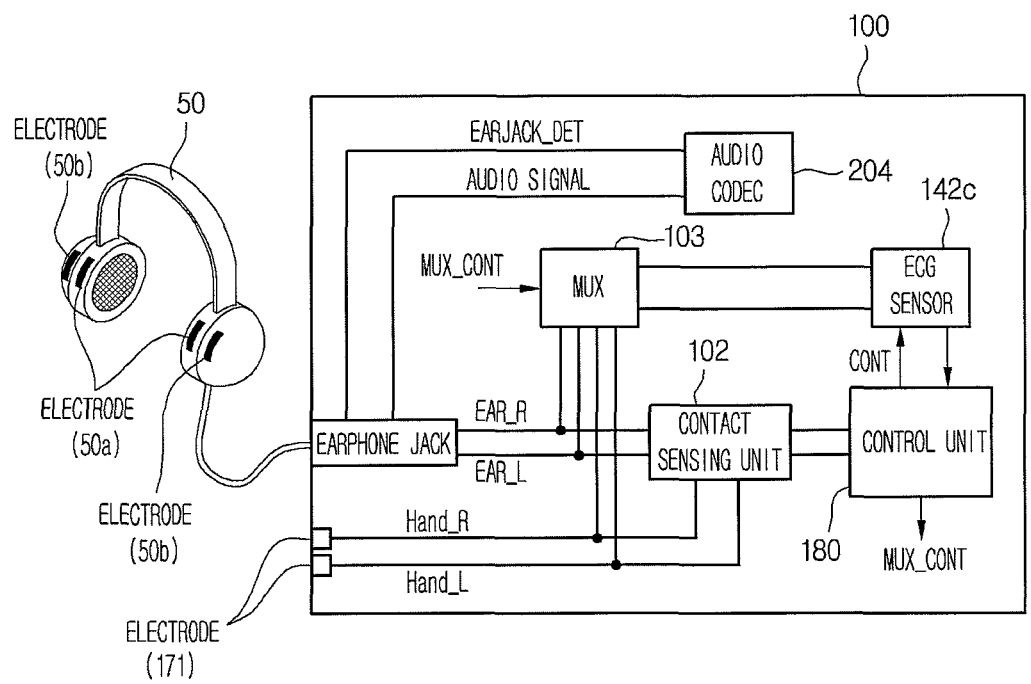
FIG. 11 is a view illustrating a bio information measuring device using a wired headset according to an embodiment.

FIG. 11 is a view illustrating a bio information measuring device using a wired headset according to an embodiment. As shown in FIG. 11, a portable terminal includes an embedded ECG sensor 142c, and an earphone jack 176 may include at least one pin for an audio signal and at least one pin for ECG signal.

As shown in FIG. 11, the wired headset 50 includes at least one ECG electrode 50a disposed at a portion that contacts the ear and at least one ECG electrode 50b disposed at a portion, i.e. the outside of the wired headset 50, where the hand frequently contacts when a user wears the wired headset 50.

The headset 50 is connected to the earphone jack 176 of the portable terminal through a plug at the end of the cable. The earphone jack 176 includes a pin for outputting a bio signal such as an ECG signal measured by the headset 60 into the ECG sensor 142c, in addition to a pin (or terminal) for outputting an audio signal to the wired headset 50.

The portable terminal 100 to which the plug of the wired headset 50 is connected may additionally include a contact sensing unit 102, a multiplexer (MUX) 103, and an ECG sensor 142c, in addition to an audio codec 240 and the control unit 180 in the portable terminal of FIG. 1. However, if the portable terminal 100 does not include an ECG electrode, the MUX 103 may be unnecessary.

The contact sensing unit 102 senses whether the ECG electrode of the wired headset 50 and the ECG electrode of the portable terminal 100 contact the user's ear or hand.

According to a contact sensing state sensed by the contact sensing unit 102, the control unit 180 controls the audio codec 240, the MUX 103, and the ECG sensor 142c.

When a user selects a predetermined music related application (for example, an MP3 function) by using the portable terminal 100, the audio codec 240 outputs an audio signal (i.e. music) through an internal sound outputting module (i.e. a speaker). When the plug of the wired headset 50 is connected to the earphone jack 176, the audio codec 240 senses it and then outputs the audio signal to the earphone jack 176 in order to output the audio signal to the wired headset 50.

The MUX 103 delivers an ECG signal, sensed by the ECG electrode of the wired headset 50 or the ECG electrode of the portable terminal 100, into the ECG sensor 142c according to a control MUX_CONT of the control unit 180.

The ECG sensor 142c generates an analog ECG signal by using the potential difference of the ECG signal sensed through at least one ECG electrode at the wired headset 50 or one side of the portable terminal. In general, in relation to an ECG, a potential difference of an electrical signal varies according to a measurement position. For example, a portion such as the hand close to the heart has a high potential difference, so that an ECG waveform may be sensed well. However, a portion such as the ear far from the heart has a low potential difference, so that an ECG waveform may not be sensed well.

Therefore, the control unit 180 determines whether the hand or the ear contacts the ECG electrode or whether one hand or both hands contact(s) the ECG electrode even when the hand contacts the ECG electrode, in order to output different control signals CONT to the ECG sensor 142. Therefore, the ECG sensor 142c amplifies an ECG signal with a gain determined by the control signal CON in order to generate the amplified ECG signal. The amplified ECG signal is delivered to the control unit 180, so that the control unit 180 displays the amplified ECG signal or information, obtained from the amplified ECG signal, on the display unit 151. Thus, the information on the display unit 151 is provided to a user.

Especially, the control unit 180 of FIG. 11 may include an MCU or an application program separated from the control unit 180 of FIG. 1. This is for the load of the control unit 180, and the control unit 180 of FIG. 11 is connected to the control unit 180 of FIG. 1. Additionally, pins (or terminals) of the earphone jack are divided for an audio signal and an ECG signal.

Also, when ear contact and hand contact occur frequently, corresponding contact is processed according to a priority. As one example, when at least two contacts, i.e. ear and hand contacts, occur, the hands contacts the electrode of the portable terminal while a user wears the headset, a priority is given to the electrode at the ear.

Figure 12:
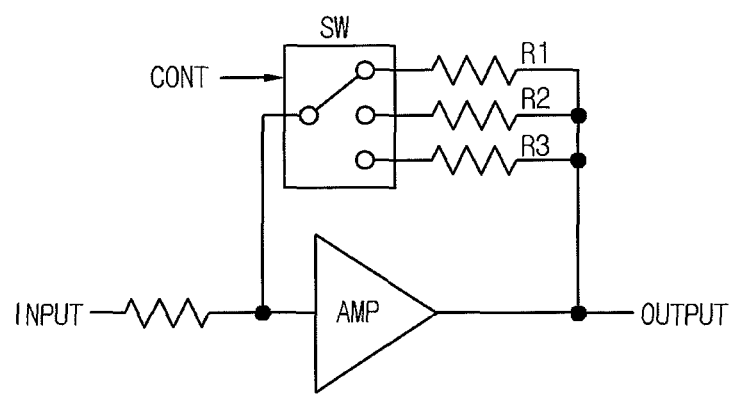
FIG. 12 is a view of a gain controlling unit equipped in an ECG sensor according to an embodiment.

FIG. 12 is a view of a gain controlling unit equipped in an ECG sensor according to an embodiment.

Referring to FIG. 12, a switch SW switches one of resistors R1, R2, and R3 according to a control signal CONT outputted from the control unit 180. The amplification unit AMP amplifies an input signal (i.e. an electrical signal outputted from an electrode) by a gain determined by the switched resistor. At this point, when the both ears contact an ECG electrode of the headset, the resistor R1 is connected, and when the hand contacts an ECG electrode of the headset, the resistor R2 is connected, and when the hand contacts an ECG electrode of the portable terminal 100, the resistor R3 is connected.

Listening to music and user's health check in an ECG sensor application device by using the headset, and a control operation of a portable terminal according to an embodiment will be described below with reference to FIG. 11.

1. Listening to Music and User's Health Check

When a user selects a predetermined music related application, for example, an MP3 function, by using a portable terminal, the audio codec 240 outputs an audio signal (i.e. music) through the internal sound outputting module (i.e., a speaker) 152.

During this state, when the plug of the headset 50 is connected to the earphone jack 176 of the portable terminal 100, the audio codec 240 does not output the audio signal to the internal sound outputting module (i.e. a speaker) 152 according to an earphone jack detect signal EARJACK_DET, but outputs the audio signal to the earphone jack 176, so that the audio signal is outputted to the ear speaker (not shown) of the headset 50. As a result, a user may listen to music, wearing the headset 50.

While a user listens to music, he/she executes a predetermined application for ECG measurement, the ECG electrode 50a at the ear contact portion, i.e. the inside of the headset 50, outputs an ECG signal EAR_R and EAR_L, measured from the both ears of the user, to the earphone jack 176 of the portable terminal. The contact sensing unit 102 detects that a current user wears the headset and the contact points of the headset are the both ears on the basis of the ECG signals EAR_R and EAR_L received through the receiving pin (i.e. a terminal) of the earphone jack 176, and then, outputs the detected contact state to the control unit 180.

According to the contact detect state, the control unit 180 outputs a control signal MUX_CONT to the MUX 103, and also outputs a gain control signal CONT to the ECT sensor 142c in order to control an amplification rate of an ECG signal. The MUX 103 outputs the ECG signal EAR_R and EAR_L, applied through the earphone jack 176, to the ECG sensor 142c according to the control signal MUX_CONT.

Accordingly, the ECG sensor 142c amplifies the ECG signal EAR_R and EAR_L, inputted through the MUX 103, by different application rates according the gain control signal CONT outputted from the control unit 180, and then, outputs the amplified ECG signal to the control unit 180. The control unit 180 displays the corresponding ECG signal on the display unit 151.

According to embodiments, an audio signal and an ECG signal are physically separated through the inner pin (i.e. a terminal) of the earphone jack 176. Therefore, while a user listens to music through the headset, a bio signal measured from the headset is detected through the ECG sensor 142c of the portable terminal in order to display a user's ECG waveform. Therefore, ECG measurement and listening to music are easily performed.

Moreover, while a user wears the headset 50 and executes an application for ECG measurement without executing an MP3 function, the headset 50 may be only used for the purpose of ECG measurement.

2. Operation Control of Portable Terminal on the Basis of Ear Contact and Hand Contact of Headset As mentioned above, ECG measurement is performed through the ECG electrode 50a attached to the inside of the headset 50. However, controls related to operations performed in the portable terminal such as listening to music and call reception are performed basically through the contact of the headset electrode 50a at the outside of the headset 50. However, since the both sides or one side of the headset are or is available, speaking accurately, a combination of the electrodes 50a and 50b at the headset 50 may be mainly used. Additionally, as mentioned in the above embodiment, ECG electrodes at different positions may be used for the operation control of the portable terminal. However, in relation to the operation of the portable terminal 100, the priority of the ECT electrode of the headset 50 is high and the priority of the ECG electrode at the portable terminal may be low.

Accordingly, while a user wears the headset 50, even if one hand contacts the electrode 50b of the headset 50 and the other hand contacts the ECG electrode 171 of the portable terminal 100, an operation of the portable terminal 100 is controlled according to the contact of the headset electrode 50b. However, when a user wears the headset 50, in case that he/she contacts the ECG electrode 171 without contacting the headset electrode 50b, an operation of the portable terminal 100 may be controlled according to the ECG electrode 171.

Table 1 and Table 2 illustrate cases of when an operation of a portable terminal is controlled according to the ear contact and hand contact of the headset.

TABLE 1

| User gesture | Contact point with headset | Operation of portable terminal |
|---|---|---|
| Detach headset | None | None/pause |
| Wear both sides of headset | Both ears | MP3 play |
| Wear both sides of headset + one hand contact | Both ears + one hand | Forward/Reverse |
| Wear both sides of headset + one hand double contact | Both ears + one hand | Pause/play |
| Wear one side of headset | One ear | Pause |

TABLE 2

| User gesture | Contact point with headset | Operation of portable terminal |
|---|---|---|
| Detach headset | None | None |
| Wear headset (one side or both sides) | One ear or both ears | Call connection when receiving a call |
| Wear headset + one hand contact | One ear or both ears + one hand | 1. call connection when receiving a call 2. call waiting |
| Detach headset | None | End |

As shown in FIG. 11, the contact sensing unit 102 determines whether a user wears the headset 50 or a user's hand contacts an ECG electrode according to the voltage size of an ECG signal measured from a plurality of ECG electrodes 50*a* attached to the inside of the headset 50, a plurality of ECG electrodes 50*b* attached to the outside of the headset 50, and a plurality of ECG electrode 171 attached to a portable terminal. The reason is that an ECG signal measured from the ear is different from that measured from the hand, and furthermore, hand contacts on the headset and the portable terminal may be different.

Accordingly, the control unit 180 may perform an MP3 playback control (for example, playback, fast forward, rewind, pause, and other), a call operation (for example, call connection and call end), a lock control (for example, screen lock release), according to a contact detect state outputted from the contact sensing unit 102.

Hereinafter, controlling MP3 playback and a call connection operation according to ear contact and hand contact will be described below.

As shown in Table 1, when the headset is taken off with no function in execution, no operation is performed. However, when a user wears and takes off the headset 50 while an MP3 function is executed, the MP3 playback stops temporarily. And, the MP3 playback starts again when the user wears the headset 50 again.

Moreover, while a user wears the both sides of the headset 50, in case that the one hand contacts the electrode 50*b* (or the electrode 171) at the side of the headset 50, the control unit 180 may perform a forward or reverse operation on the MP3 playback according to a touch of the right-side electrode or the left-side electrode.

Moreover, while a user wears the both sides of the headset 50, in case that one hand double-contacts the headset 50*b* (or the electrode 171), the control unit 180 stops or perform the MP3 playback. At this point, the double contact may be distinguished by the right or left electrode. Additionally, when only one side of the headset remains after a user wears the both sides of the headset, the control unit 180 stops the MP3 playback.

Moreover, the control unit 180 may process a call reception according to the ear contact and hand contact of the headset. As shown in Table 2, when a call is received with the both sides of the headset put on (for example, one side or both sides), a call is immediately connected. Additionally, when a call is received with the both sides of the headset put on (for example, one side or both sides), a call connection is performed, and later, when one hand contacts the electrode 50*a* or 171, call waiting is performed (if the one hand contacts again, a call is performed). Afterward, when the user takes off the headset, the control unit 180 ends the call.

Figure 13:
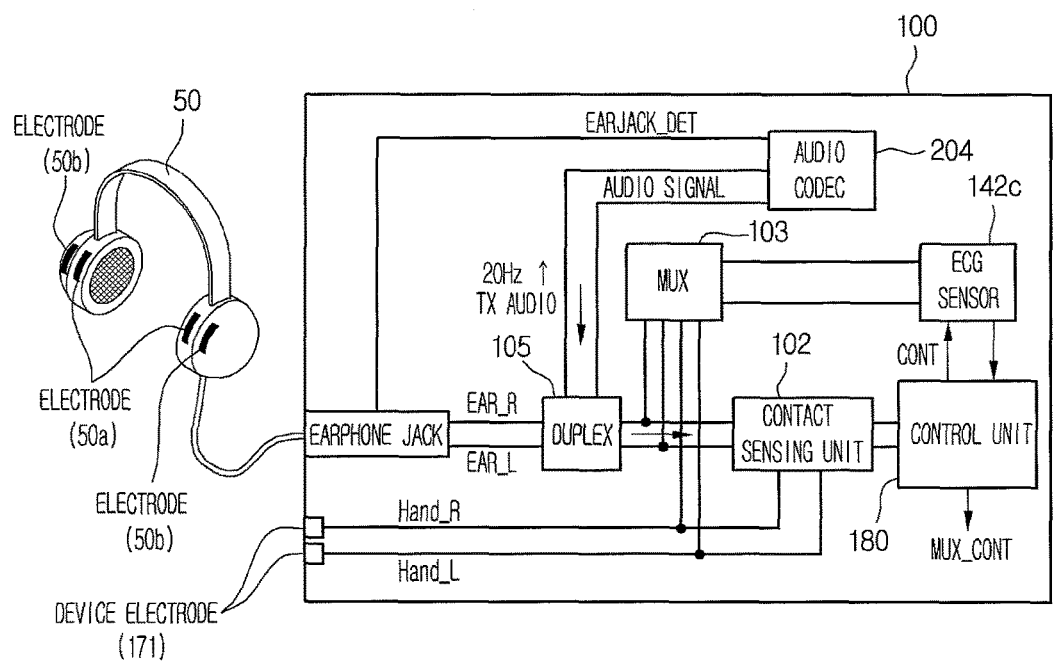
FIG. 13 is a view illustrating a bio information measuring device using a wired headset according to another embodiment.

FIG. 13 is a view illustrating a bio information measuring device using a wired headset according to another embodiment. Although an audio signal and an ECG signal are separated by increasing the number of pins in the earphone jack 176 according to the embodiment of FIG. 11, the embodiment of FIG. 13 uses the earphone jack 176 as it is but uses a duplexer 105 that separates TX/RX signals by the frequency band.

That is, the duplex 105 outputs an audio signal of about 20 Hz, which is to be transmitted, to the earphone jack 176, and delivers an ECG signal of about 20 Hz, received from the headset 50 through the earphone jack 176, to the contact sensing unit 102. Since other operations are the same as those of FIG. 11, detailed description will be omitted.

The ECG sensor 142*c* may be embedded in the portable terminal. However, the present invention is not limited thereto, and the ECG sensor 142*c* may be embedded in the headset. In this case, the headset analyzes an ECG signal in order to measure ECG, and then transmits it the portable terminal.

Figure 14:
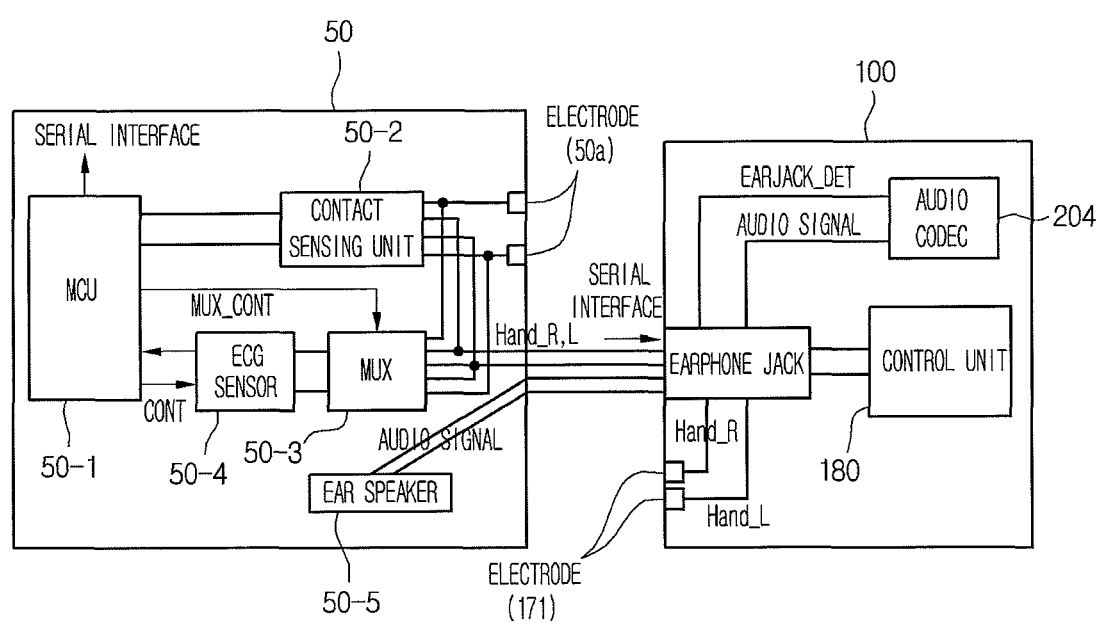
FIG. 14 is a view illustrating a bio information measuring device using a wired headset according to another embodiment.

FIG. 14 is a view illustrating a bio information measuring device using a wired headset according to another embodiment. This embodiment includes the ECG sensor embedded in the headset.

As shown in FIG. 14, when a user executes an MP3 function with the headset 50 connected to the portable terminal 100, an audio signal outputted from an audio codec 50-2 is outputted to an ear speaker 50-5 of the headset 50 through the earphone jack 176.

When the headset 50 is connected to the earphone jack 176 of the portable terminal 100 or an audio signal is outputted through the ear speaker 50-5, a contact sensing unit 50-2 detects the contact (for example, ear or hand contact) from the headset 50 in order to output a contact detect signal to an MCU 50-1. The MCU 50-1 determines the types of contact (for example, ear or hand) according to the contact detect signal outputted from the contact sensing unit, and then, outputs a control signal MUX_CONT for controlling a MUX 50-3 and a control signal CONT for controlling a gain of an ECG sensor 50-4.

The MUX 50-3 operates according to the control signal MUX_CONT in order to output the ECG signal, detected by the electrode 50*a*, to the ECG sensor 50-4, and outputs a signal Hand_R and Hand_L, detected by the electrode 50*b* at the side of the headset, to the earphone jack 176 of the portable terminal 100.

The ECG sensor 50-4 amplifies an ECG signal detected from the ear according to the gain control signal CONT outputted from the MCU 50-2, and outputs the amplified ECG signal to the MCU 50-2. Then, the MCU 50-1 outputs the ECT signal amplified by the ECG sensor 50-4 to the earphone jack 176 of the portable terminal through a serial interface.

Accordingly, the control unit 100 of the portable terminal displays the ECG waveform received through the earphone jack 176 on the display unit 151. While an MP3 function is executed or a call is received, the control unit 100 controls various operations of the portable terminal (for example, MP3 playback, call reception, and screen lock release) as shown in Table 1 and Table 2, by using the hand detect signals Hand_R and Hand_L, which are detected by the electrode 50*b* of the headset and delivered through the earphone jack 176, and the hand detect signals Hand_R and Hand_L, which are detected by the electrode 171 of the portable terminal.

In relation to the operations of FIGS. 11 to 14, the electrode 50*b* of the headset 50 and the electrode 171 of the portable terminal may be used for detecting an ECG signal and also controlling an operation of the portable terminal Especially, when the ECG sensor is embedded in the headset 50, the headset 50 measures a user's ECG signal and transmits it to the portable terminal.

According to the method and structure of applying an ECG sensor by using the headset shown in FIGS. 11 to 14, the headset is connected to the portable terminal by a wire. However, the present invention is not limited thereto. That is, when the headset is connected to the portable terminal wirelessly, the almost same operation is provided.

Figure 15:
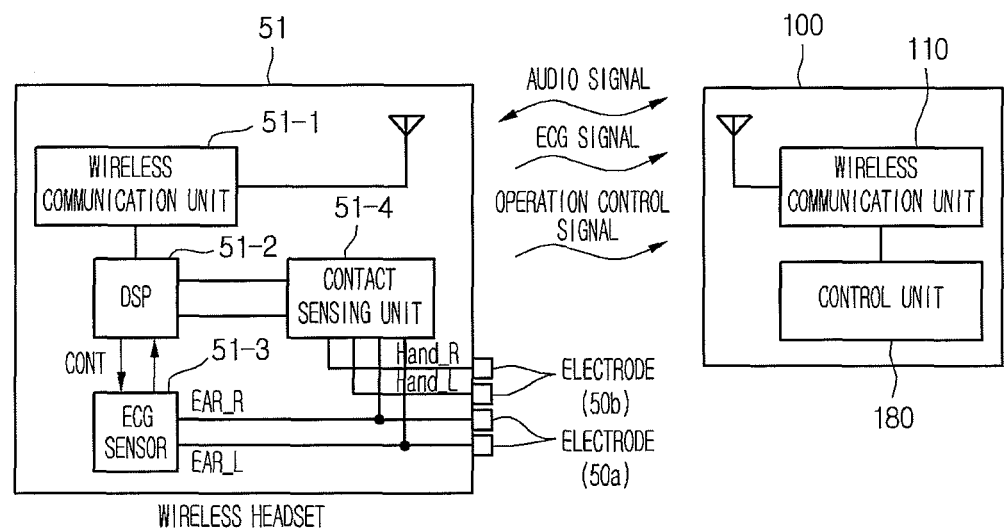
FIG. 15 is a view illustrating a bio information measuring device using a wireless headset according to an embodiment.

FIG. 15 is a view illustrating a bio information measuring device using a wireless headset according to an embodiment.

The wireless headset 51 includes a wireless communication unit 50-1. The wireless communication unit 51-1 mainly performs short range communication such as Bluetooth.

When a user executes an MP3 function in the portable terminal 100 with the wireless headset 51 put on, the wireless communication unit 11 transmits an audio signal through an antenna according to a control of the control unit 180. Then, the transmitted audio signal is received by an antenna of the wireless headset 51 and is applied to the wireless communication unit 51-2. Accordingly, a DSP 51-2 processes the received audio signal and outputs it to an ear speaker (not shown) in order to play music.

While the music is played or an MP3 function is not executed, a user selects an application for ECG measurement from a menu and executes it. Then, a corresponding signal is delivered to the headset 51 and the DSP 51-2 starts an operation for ECG measurement.

That is, the electrode at the inside of the headset 51 outputs a user's bio signal, i.e. an ECG signal, and the electrode at the outside of the headset 51 outputs user's hand touché signals Hand_R and Hand_L. The contact sensing unit 51-2 detects hand contact or ear contact from the signals outputted from the electrodes 50a and 50b in order to a contact detect signal to the DSP 51-2. Also, the ECG sensor 51-3 amplifies the ECG signal measured by the electrode 50a according to the gain control signal of the DSP 51-2 in order to output it to the DSP 51-2.

Accordingly, the DSP 51-2 outputs the ECG signal measured by the ECG sensor 51-3 to the portable terminal 100 through the wireless communication unit 51-2, and the control unit 180 displays the ECG waveform received through the wireless communication unit 110 on the display unit 151.

Moreover, while the MP3 function is executed to play a predetermined music through the ear speaker of the wireless headset 51, as shown in Table 1, if a user contacts the electrode 50b or changes a wearing state of the headset, the contact sensing unit 51-4 determines hand contacts Hand_R and Hand_L and ear contacts Ear_R and Ear_L in order to output a determination result to the DSP 51-2, and generates an operation control signal for controlling an operation of the portable terminal according to the contact detect signal outputted from the contact sensing unit 51-4, in order to transmit the operation control signal to the wireless communication unit 51-1.

Accordingly, the control unit 180 of the portable terminal controls an MP3 function as shown in Table 1 according to the operation control signal received through the wireless communication unit 110. Moreover, while a user wears the wireless headset 51 or listens to music with the wireless headset 51 put on, a call is received, as shown in Table 2, a call receiving operation is performed according to a contact state of the two electrodes 50a and 50b of the wireless headset 51.

Next, a circuit of a portable terminal according to an embodiment will be described below with reference to FIG. 16.

Figure 16:
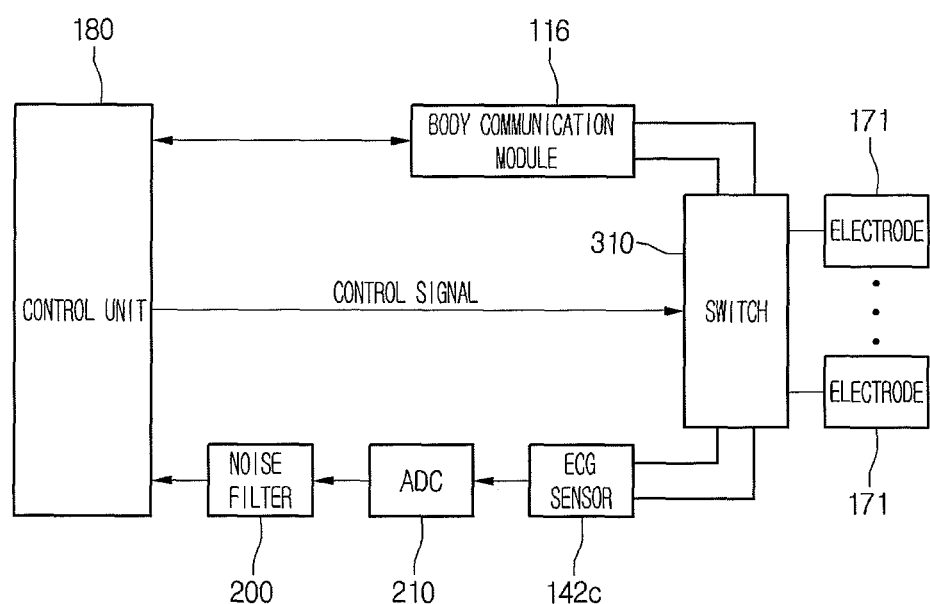
FIG. 16 is a block diagram illustrating part of a circuit of a portable terminal according to an embodiment.

FIG. 16 is a block diagram illustrating part of a circuit of a portable terminal according to an embodiment.

As shown in FIG. 16, the portable terminal 100 further includes a switch 310, a noise filter 200, an analog-digital converter (ADC) 210.

A plurality of ECG electrodes 171 correspond to ports for receiving an ECG signal from a body.

The switch 310 connects the two body-contacted electrodes among the plurality of ECG electrode 171 to the ECG sensor 142c, or to the body communication module 116 according to a control signal of the control unit 180.

The ECG sensor 142c detects an analog ECG signal from the signal of the two body-contacted electrodes.

The ADC 210 converts the analog ECG signal into a digital ECG signal.

The noise filter 200 removes the noise from the digital ECG signal in order to generate the filtered ECG signal, and then delivers the filtered ECG signal to the control unit 180.

The body communication module 116 modulates the data received from the control unit 180 for body communication, and outputs the modulated signal to the two body-contacted electrodes through the switch 310. Additionally, the body communication module 116 demodulates the received signal from the two body-contacted electrodes, and then, delivers the demodulated data to the control unit 180. The modulation for body communication may be Frequency Modulation (FM). The demodulation for body communication may be demodulation corresponding to the FM.

The control unit 180 compares a pattern of the ECG signal received through the ECG sensor 142c with an ECG pattern of a user previously stored in the memory 160. If they are identical, the control unit 180 controls the switch 310 to be connected to the body communication module 116.

Figure 17:
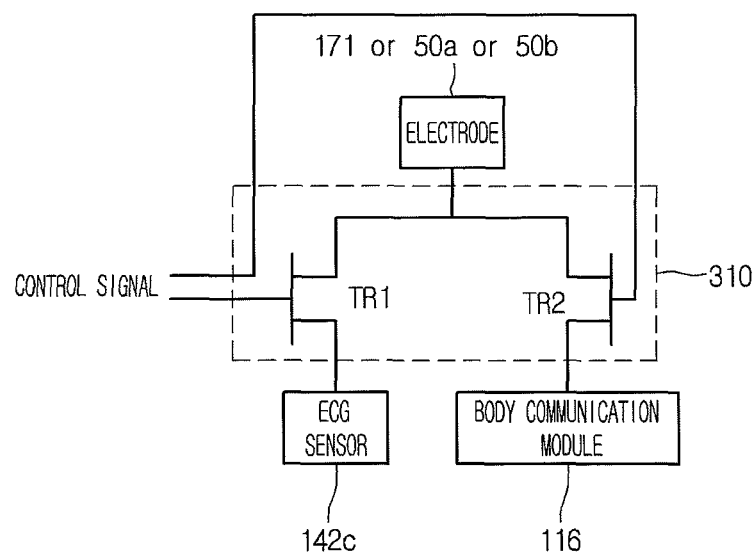
FIG. 17 is schematic structure of a switch according to an embodiment.

FIG. 17 is schematic structure of a switch according to an embodiment.

Referring to FIG. 17, the switch 310 may include a first transistor TR1 and a second transistor TR2 in order for an ECG electrode 171 at the body of the portable terminal 100, an ear contact electrode 50a of an ear accessory, and a hand contact electrode 50b. It is assumed that the first transistor TR1 and the second transistor TR2 are a Field Effect Transistor (FET), but may be different kinds of transistors.

The first transistor TR1 related to the ECG electrode 171 includes a gate electrode through which a control signal is supplied, a drain electrode connected to the ECG electrode 171, and a source electrode connected to the ECG sensor 142c. If the number of the ECG electrodes 171 is more than two, the number of the first transistors TR1 may be more than two.

The second transistor TR1 related to the ECG electrode 171 includes a gate electrode through which a control signal is supplied, a drain electrode connected to the ECG electrode 171, and a source electrode connected to the body communication module 116. If the number of the ECG electrodes 171 is more than two, the number of the second transistors TR2 may be more than two.

The first transistor TR1 related to the ear contact ECG electrode 50a or 341 of the ear accessory includes a gate electrode through which a control signal is supplied, a drain electrode connected to the ear contact ECG electrode 50a or 341, and a source electrode connected to the ECG sensor 142c. If the number of the ear contact ECG electrodes 50a or 341 is more than two, the number of the first transistors TR1 may be more than two.

The second transistor TR2 related to the ear contact ECG electrode 50a or 341 of the ear accessory includes a gate electrode through which a control signal is supplied, a drain electrode connected to the ECG electrode 50a or 341, and a source electrode connected to the body communication module 116. If the number of the ECG electrodes 50a or 341 is more than two, the number of the second transistors TR2 may be more than two.

The first transistor TR1 related to the hand contact ECG electrode 50b includes a gate electrode through which a control signal is supplied, a drain electrode connected to the ECG electrode 50b, and a source electrode connected to the ECG sensor 142c. If the number of the ECG electrodes 50b is more than two, the number of the first transistors TR1 may be more than two.

The second transistor TR2 related to the hand contact ECG electrode 50b includes a gate electrode through which a control signal is supplied, a drain electrode connected to the ECG electrode 50b, and a source electrode connected to the body communication module 116. If the number of the ECG electrodes 50b is more than two, the number of the second transistors TR2 may be more than two.

Additionally, according to an embodiment of the present invention, the control unit 180 provides a control signal to the switch 310 based on whether an ear accessory such as the earphone 300 or the headset 51 is attached to the portable terminal 100, in order to connect the electrodes 171 at the body outside surface of the portable terminal 100 or the electrodes 341 at the main body of the earphone 300 to the ECG sensor 142c. Additionally, the control unit 180 provides a control signal to the switch 310 based on whether an ear accessory is attached to the portable terminal 100, in order to connect the electrodes 171 at the body outside surface of the portable terminal 100 or the electrodes 341 at the main body of the earphone 300 to the body communication module 116.

For example, if an ear accessory is attached to the portable terminal 100, the control unit 180 provides a control signal to the switch 310 in order to connect the ear contact ECG electrode of an ear accessory and/or the hand contact ECG electrode of an ear accessory to the ECG sensor 142c.

Additionally, if an ear accessory is attached to the portable terminal 100, the control unit 180 provides a control signal to the switch 310 in order to connect the ear contact ECG electrode of an ear accessory and/or the hand contact ECG electrode of an ear accessory to the body communication module 116.

Additionally, for example, if an ear accessory is not attached to the portable terminal 100, the control unit 180 may connect the electrodes 171 at the body outside surface of the portable terminal 100 to the ECG sensor 142c and/or the body communication module 116.

Again, referring to FIG. 17, the switch 203 controls the ECG signal obtained through the ECG electrodes 171, 50a, 50b, or 341 to be inputted into the ECG sensor 142c and/or the body communication module 116, on the basis of the control signal.

According to an embodiment, if an ear accessory is not attached to the portable terminal 100 and the proximity sensor 141a detects the proximity of an object during a call, the control unit 180 may connect the electrodes 171 at the body outside surface of the portable terminal 100 to the ECG sensor 142c and/or the body communication module 116.

According to an embodiment, if an ear accessory is not attached to the portable terminal 100, the control unit 180 may connect the electrode 50a, 50b, or 341 at the ear accessory to the ECG sensor 142c and/or the body communication module 116.

Moreover, only when the portable terminal 100 operates in a call mode, the control unit 180 may activates the proximity sensor 141a. Accordingly, the proximity sensor 141a is activated only in a call mode, so that it detects an object approaching the sound outputting module 152 and outputs a detect signal as a control signal.

The control unit 180 analyzes an ECG signal in order to check a user's emotion state and health state.

If no ECG electrode is connected to the ECG sensor 142c, the control unit 180 cuts off power to the ECG sensor 142c, the ADC 210, and the noise filter 200 in order to reduce power consumption.

Next, the noise filer 200 according to various embodiments will be described with reference to FIGS. 18 to 21.

Unlike dedicated ECG measurement equipment, the portable terminal 100 is exposed to various noise environments. For example, when the portable terminal measures ECG, a text message or a call may arrive, and at this point, alarm sound, bell sound, and vibration may be the noise of an ECG signal. Moreover, a user may measure ECG in order to check a user's health or record a user's current emotion state while being on the move, listening to music, watching a video, or being at a concert. Noise may occur during winter due to electrostatic, and noise of about 60 Hz frequency may occur due to AC power during charging of the portable terminal 100.

As mentioned above, when ECG is measured through the portable terminal 100, a noise filter that is applicable to various noise environment is required.

Especially, while the control unit 180 measures ECG through the ECG sensor 142c, once a text message or a call reception is detected, the control unit 180 turns off the alarm unit 153.

Hereinafter, a filter that removes another noise will be described.

Figure 18:
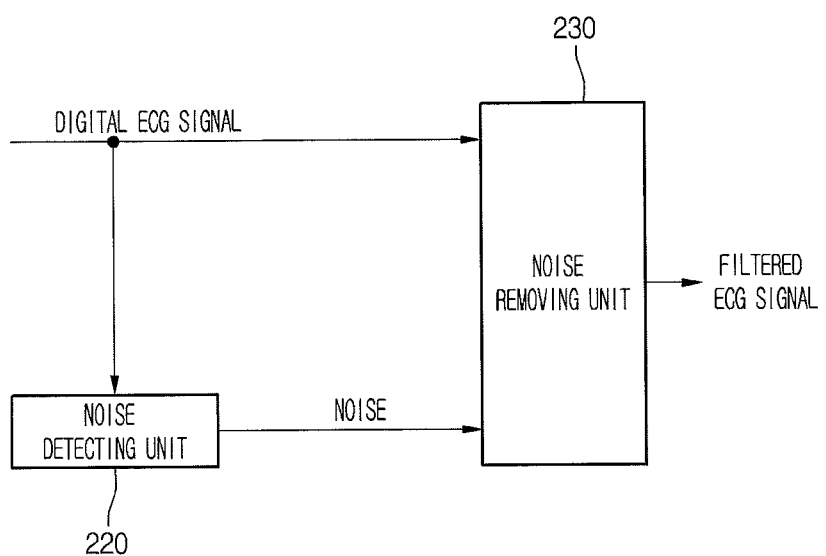
FIG. 18 is a block diagram of a noise filter according to an embodiment.

FIG. 18 is a block diagram of a noise filter according to an embodiment.

As shown in FIG. 18, the noise filter 200 includes a noise detecting unit 220, and a noise removing unit 230.

The noise detecting unit 220 detects the noise from a digital ECG signal. The detected noise may be a noise signal on a time axis or a noise frequency pattern on a frequency axis.

The noise removing unit 230 removes the noise from a digital ECG signal. Especially, when the noise detecting unit 220 detects a noise signal, the noise removing unit 230 may correspond to a subtraction unit that reduces a noise signal from a digital ECG signal. Additionally, when the noise detecting unit 220 detects a noise frequency pattern, the noise removing unit 230 may correspond to a notch filter that cuts off a noise frequency pattern from a digital ECG signal.

Figure 19:
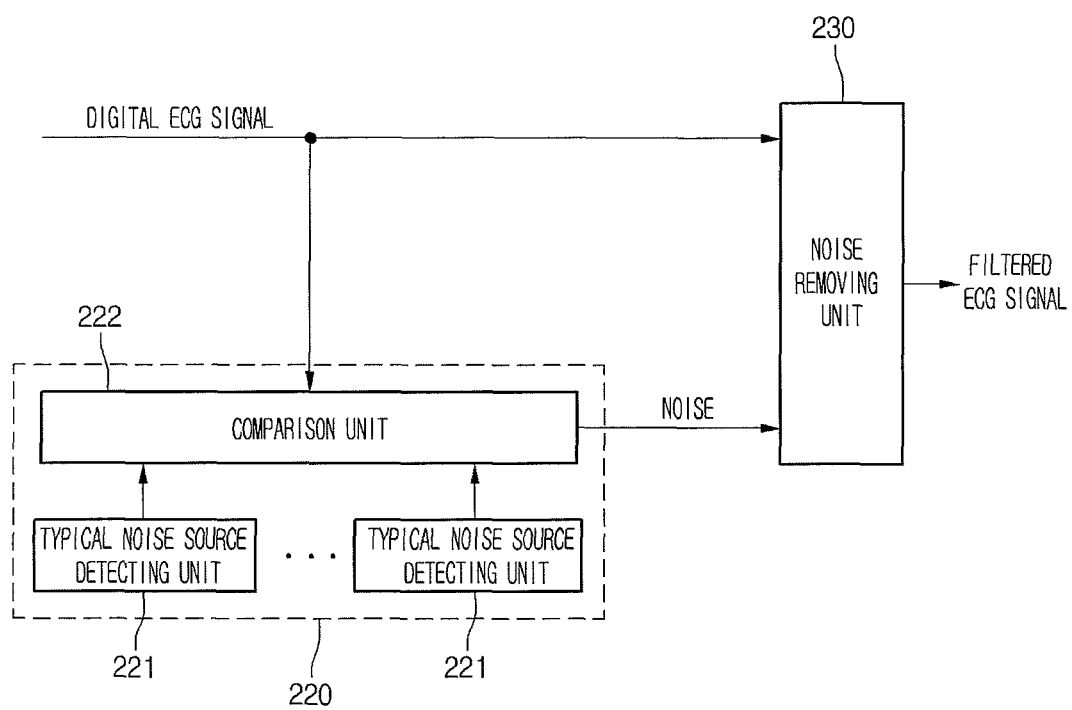
FIG. 19 is a block diagram of a noise filter according to an embodiment.

FIG. 19 is a block diagram of a noise filter according to an embodiment.

As shown in FIG. 19, the noise filter 200 includes a noise detecting unit 220, and a noise removing unit 230. The noise detecting unit 220 includes at least one typical noise source detecting unit 221 and a comparison unit 222.

The typical noise source detecting unit 221 detects a typical noise source and outputs a noise source signal. The typical noise source detecting unit 222 may correspond to a vibration sensor, an electromagnetic sensor, a source detecting unit, and an AC power detecting unit. The vibration sensor detects vibration and outputs a noise source signal corresponding to the vibration detect signal. The electromagnetic sensor detects an electromagnetic wave and outputs a noise source signal corresponding to the electromagnetic detect signal. The sound detecting unit detects a sound source and outputs a noise source signal corresponding to the signal source. The AC power detecting unit detects an AC power and outputs a noise source signal corresponding to the AC power signal.

The comparison unit 222 compares a digital ECG signal with a noise source signal and outputs noise. The comparison unit 222 outputs a noise signal or a noise frequency pattern.

Figure 20:
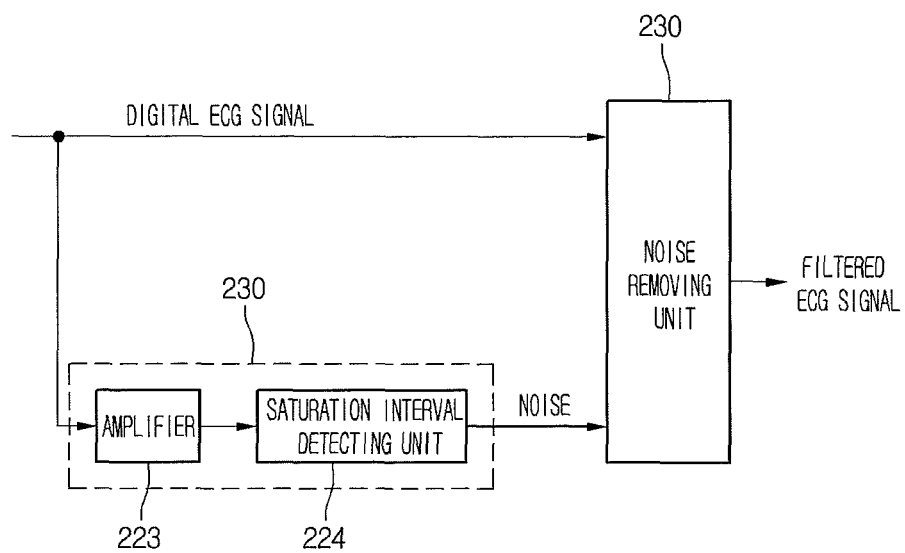
FIG. 20 is a block diagram of a noise filter according to an embodiment.

FIG. 20 is a block diagram of a noise filter according to an embodiment.

As shown in FIG. 20, the noise filter 200 includes a noise detecting unit 220, and a noise removing unit 230. The noise detecting unit 220 includes an amplifier 223 and a saturation interval detecting unit 224.

The amplifier 223 amplifies a digital ECG signal and generates an amplified digital ECG signal.

The saturation interval detecting unit 224 detects a saturation interval from the amplified ECG signal to detect the noise corresponding to the detected saturation interval. The saturation interval detecting unit 224 outputs a noise signal or a noise frequency pattern.

Through the noise filter of FIG. 20, noise due to electrostatic during winter or noise of about 60 Hz frequency during charging of the portable terminal 100 may be removed.

Figure 21:
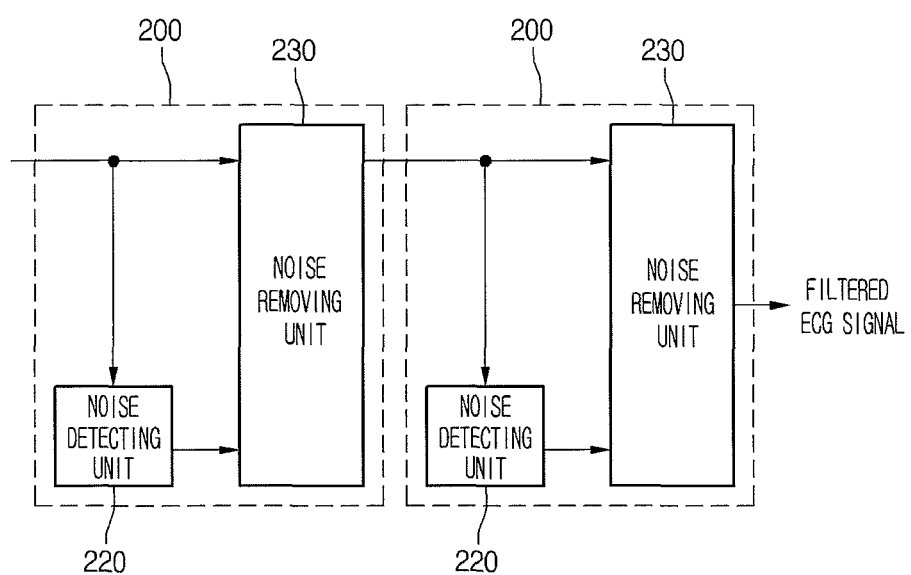
FIG. 21 is a block diagram of a noise filter according to another embodiment.

FIG. 21 is a block diagram of a noise filter according to another embodiment.

As shown in FIG. 21, a plurality of noise filters 200 may be connected in series. For example, the portable terminal 100 may include a first filter corresponding to the noise filter of FIG. 19 and a second filter corresponding to the noise filter of FIG. 20.

Figure 22:
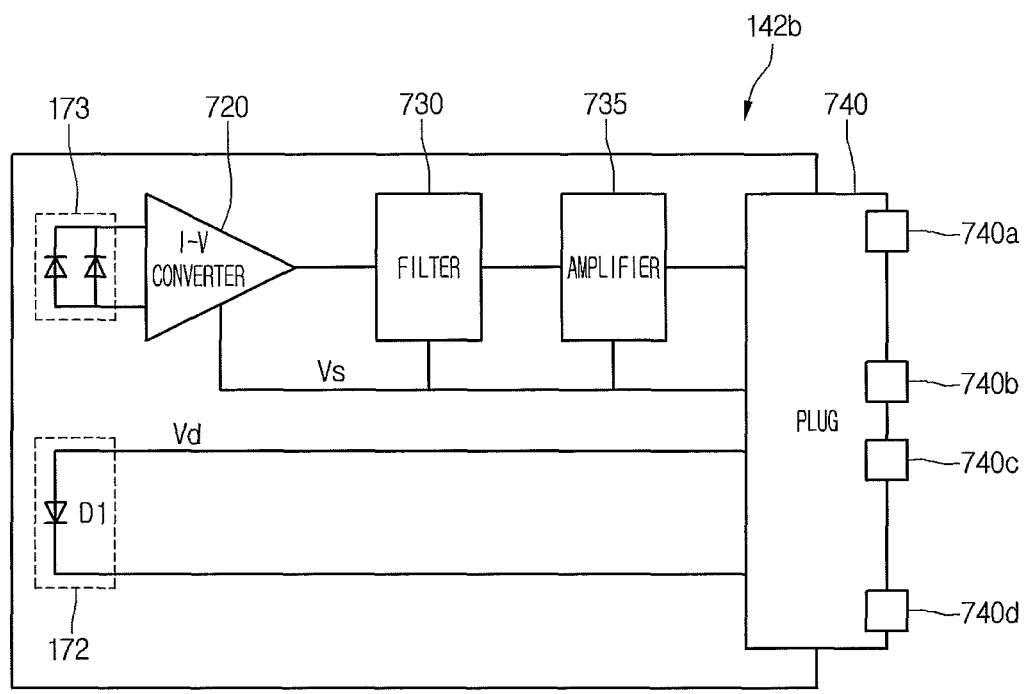
FIG. 22 is a view of an earphone jack type PPG sensor according to an embodiment.
Figure 23:
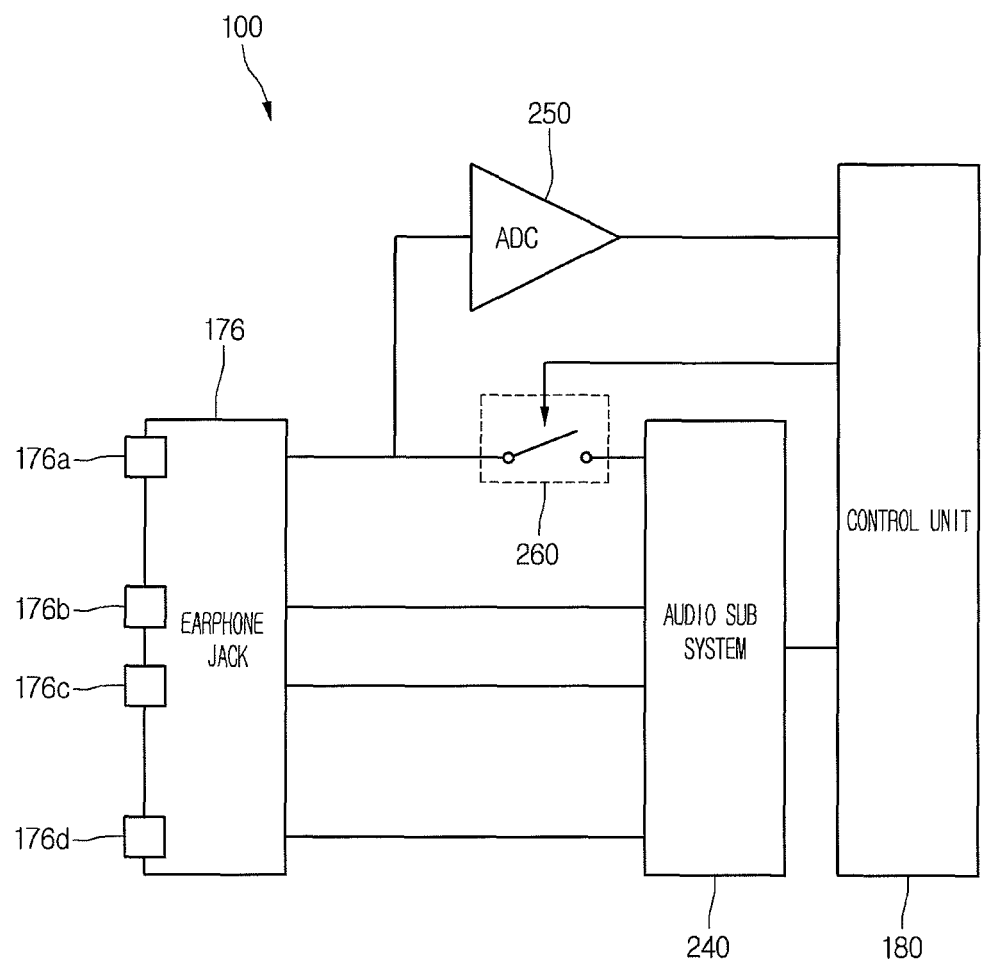
FIG. 23 is a block diagram illustrating additional components of a portable terminal according to an embodiment.

With reference to FIGS. 22 and 23, an earphone jack type photoplethysmographic (PPG) signal sensor and a portable terminal supporting the same will be described.

FIG. 22 is a view of an earphone jack type PPG sensor according to an embodiment.

As shown in FIG. 22, the earphone jack type PPG sensor 142b includes a light emitting diode 172, a light receiving diode 173, a current-voltage (I-V) converter 720, a filter 730, an amplifier 735, and a plug 740. The plug includes a mike signal port 740a, a first ear speaker port 740b, a second ear speaker port 740c, and a ground port 740d.

The anode terminal of the light emitting diode 172 is connected to the second ear speaker port 740c, and its cathode terminal is connected to the ground port 740d. The anode terminal and the cathode terminal of the light receiving diode 173 are respectively connected to two input terminals of the I-V converter 720. The output terminal of the I-V converter 720 is connected to the input terminal of the filter 730. The output terminal of the filter 730 is connected to the input terminal of the amplifier 735. The output terminal of the amplifier 735 is connected to the mike signal port 740a.

FIG. 23 is a block diagram illustrating additional components of a portable terminal according to an embodiment.

As shown in FIG. 23, the portable terminal 100 includes an earphone jack 176, an audio codec 240, an ADC 250, and a switch 260. The earphone jack 176 includes a mike signal port 176a, a first ear speaker port 176b, a second ear speaker port 176c, and a ground port 176d.

The input terminal of the ADC 250 is connected to the mike signal port 176a. The output terminal of the ADC 250 is connected to the control unit 180. One end of the switch 260 is connected to the mike signal port 176a and the other end is connected to the mike signal input terminal of the audio codec 240. The first ear speaker port 176b and the second ear speaker port 176c are connected to the two audio output terminal of the audio codec, respectively.

In order to use the earphone jack 176 for audio usually, the control unit 180 provides a control signal to the switch 260 in order to turn it on.

Once the plug 740 is inserted into the earphone jack 176, the mike signal port 740a, the first ear speaker port 740b, the second ear speaker port 740c, and the ground port 740d are connected to the mike signal port 176a, the first ear speaker port 176b, the second ear speaker port 176c, and the ground port 176d, respectively.

Then, the light emitting diode 172 emits light by an initial voltage applied to the second ear speaker port 176c.

Moreover, the I-V converter 720, the filter 730, and the amplifier 735 operate abnormally by an initial voltage applied to the first ear speaker port 176b. That is, the light receiving diode 173 receives the light emitted from the light emitting diode 172 in order to generate a current signal. The I-V converter 720 converts the generated current signal into a voltage signal by an initial voltage. The filter 730 filters a voltage signal by an initial voltage in order to generate a filtered voltage signal. The amplifier 735 amplifies the voltage signal filtered by an initial voltage in order to generate an initial PPG signal.

The initial PPG signal is not an accurate blood movement measurement signal, but increases a DC level of the mike signal port 176a.

The ADC 250 converts the initial PPG signal into a digital signal and provides it to the control unit 180.

When the control unit 180 detects a DC level increase of the mike signal port 176a, it is recognized that the PPG sensor 142b is inserted into the earphone jack 176. Moreover, in order to use the earphone jack 176 for the PPG sensor 142b, the control unit 180 provides a control signal to the switch 260 in order to turn it off.

Moreover, in order to provide stable power to the PPG sensor 142b, the control unit 180 controls the audio codec 240 in order to provide DC voltage to the first ear speaker port 176b and the second ear speaker port 176c.

Once stable power is provided to the PPG sensor 142b, the light emitting diode 172 emits light normally by the DC voltage applied to the second ear speaker port 740c. Moreover, the I-V converter 720, the filter 730, and the amplifier 735 operate normally by the DC voltage applied to the first ear speaker port 740b. Accordingly, the amplifier 735 provides a normal blood movement measurement signal to the mike signal port 740a, and the ADC 250 converts a normal blood movement measurement signal into a digital signal and provides it to the control unit 180.

Then, a method of changing a mode of a portable terminal will be described with reference to FIGS. 24 to 27.

Figure 24:
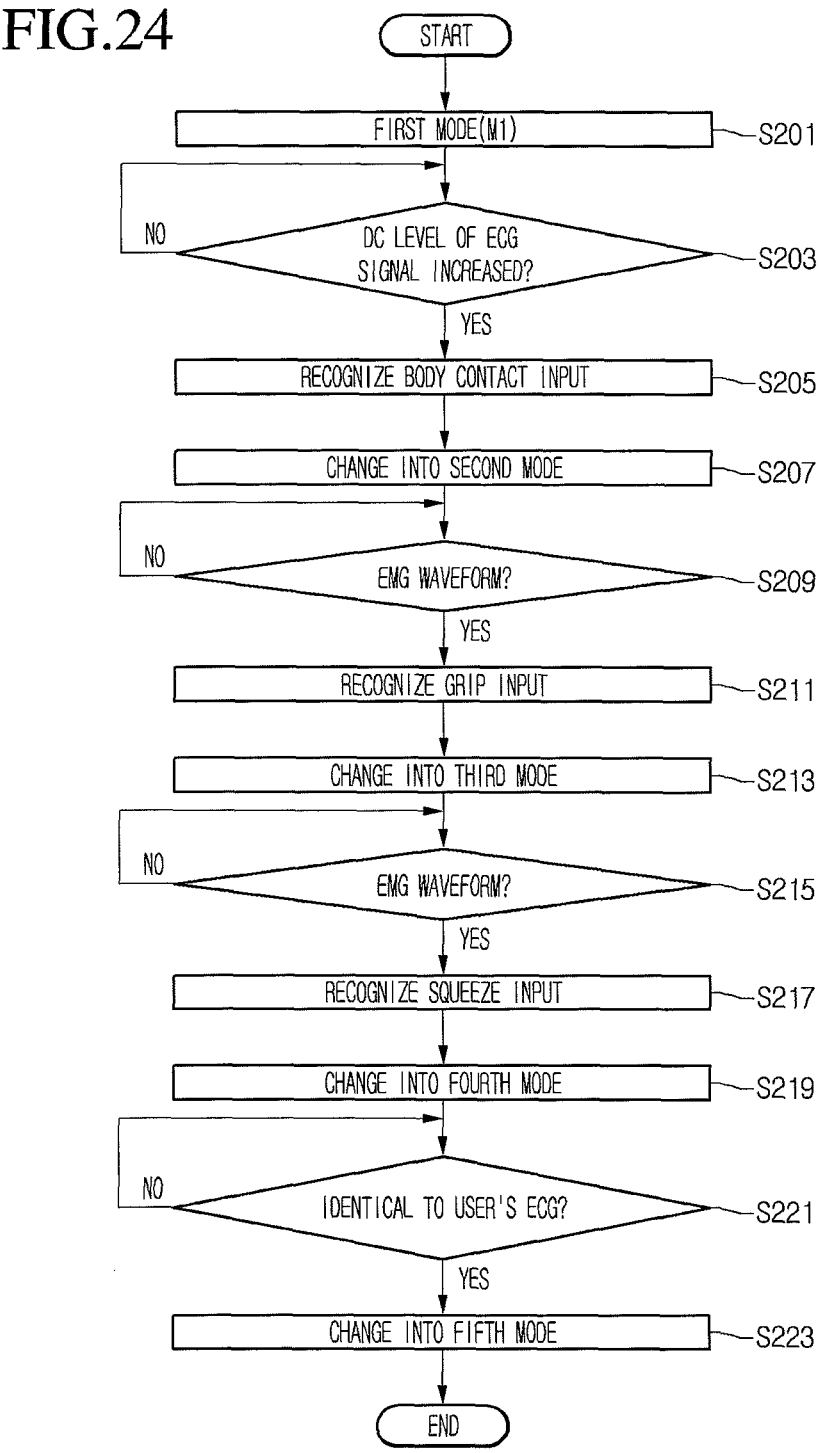
FIG. 24 is a flowchart of a mode changing method according to an embodiment.

FIG. 24 is a flowchart of a mode changing method according to an embodiment.

First, the control unit 180 of the portable terminal 100 is in a first mode M1 in operation S201. According to an embodiment, the first mode M1 may be a sleep mode. According to an embodiment, the first mode M1 may be a call reception state. According to an embodiment, the first mode M1 may be a message reception state.

In the first mode M1, the control unit 180 confirms a DC level increase of an ECG signal in operation S203. When the user's hand contacts one of the plurality of ECG electrodes 171, the DC level of an ECG signal is increased, but an ECG waveform does not occur. When the user's hand contacts at least two of the plurality of ECG electrodes 171, the DC level of an ECG signal is increased, and an ECG waveform occurs.

Once the DC level of an ECG signal is increased, the control unit 180 recognizes that interrupt corresponding to a body contact input occurs in operation S205, and changes the first mode M1 into a second mode M2 in response to interrupt corresponding to a body contact input in operation S207.

In the second mode M2, the control unit 180 confirms the detection of an ECG waveform in operation S209. In general, when the user's hand contacts at least two of the plurality of ECG electrodes 171, an ECG waveform occurs.

Once an ECG waveform is detected, the control unit 180 recognizes that interrupt corresponding to a grip input occurs in operation S211, and changes the second mode M2 into a third mode M3 in response to interrupt corresponding to the grip input in operation S213.

In the third mode M2, the control unit 180 confirms the detection of a squeeze waveform in operation S215. In general, when the user's hand contacts at least two of the plurality of ECG electrodes 171, a user squeezes the portable terminal 100, an electromyogram (EMG) waveform occurs due to the strength of an EMG signal.

Once an EMG waveform is detected, the control unit 180 recognizes that interrupt corresponding to a squeeze input occurs in operation S217, and changes the third mode M3 into a fourth mode M4 in response to interrupt corresponding to the squeeze input in operation S219.

In the fourth mode M4, the control unit 180 confirms a pattern of the received ECG signal is identical to a pattern of a user's ECG signal in operation S221.

Once they are identical, the control unit 180 determines that a user authentication is successful, and changes the fourth mode M4 into a fifth mode M5.

Figure 25:
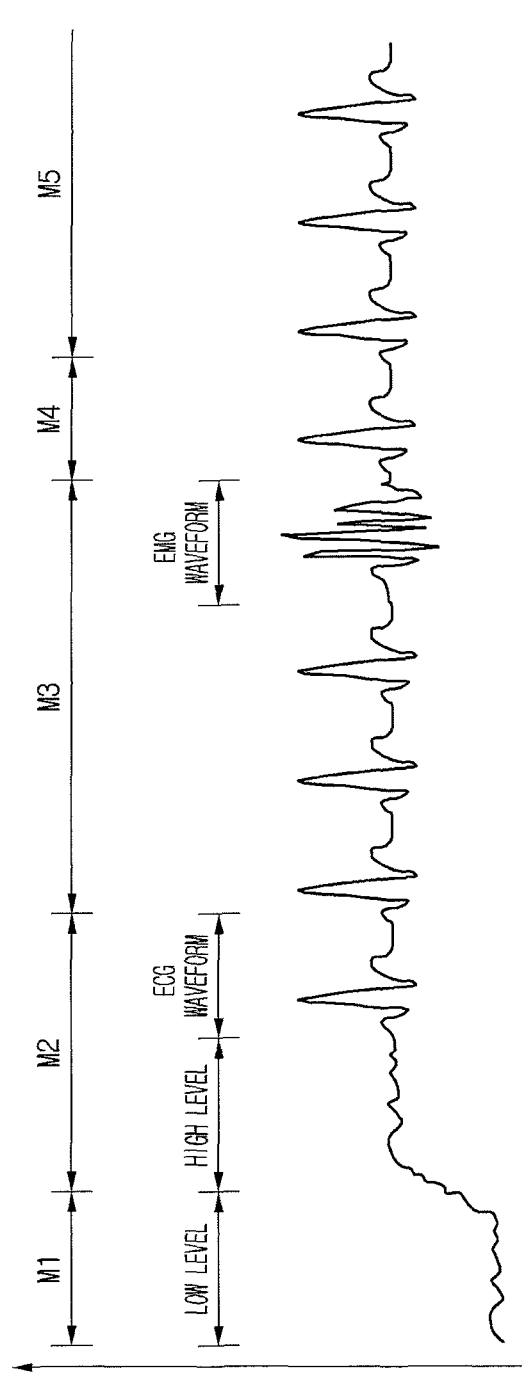
FIG. 25 is a graph illustrating a relation between a plurality of modes and an ECG signal according to an embodiment.

FIG. 25 is a graph illustrating a relation between a plurality of modes and an ECG signal according to an embodiment.

As shown in FIG. 25, when the DC level of an ECG signal is less than the predetermined level, the control unit 180 is in the first mode M1.

When the user's hand contacts one of the plurality of ECG electrodes 171, the DC level of an ECG signal becomes more than the predetermined level, and the control unit 180 changes the first mode M1 into the second mode M2.

When the user's hand contacts at least two of the plurality of ECG electrodes 171, an ECG waveform occurs, and the control unit 180 changes the second mode M2 into the third mode M3.

When the user's hand contacts at least two of the plurality of ECG electrodes 171 and the user squeezes the portable terminal 100, as shown in FIG. 25, an EMG waveform occurs, and the control unit 180 changes the third mode M3 into the fourth mode M4.

When the user's hand contacts at least two of the plurality of ECG electrodes 171 and the user release the portable terminal 100, an ECG waveform occurs again. At this point, the control unit 180 performs user authentication and it is successful, the control unit 180 changes the fourth mode M2 into the fifth mode M5.

Figure 26:
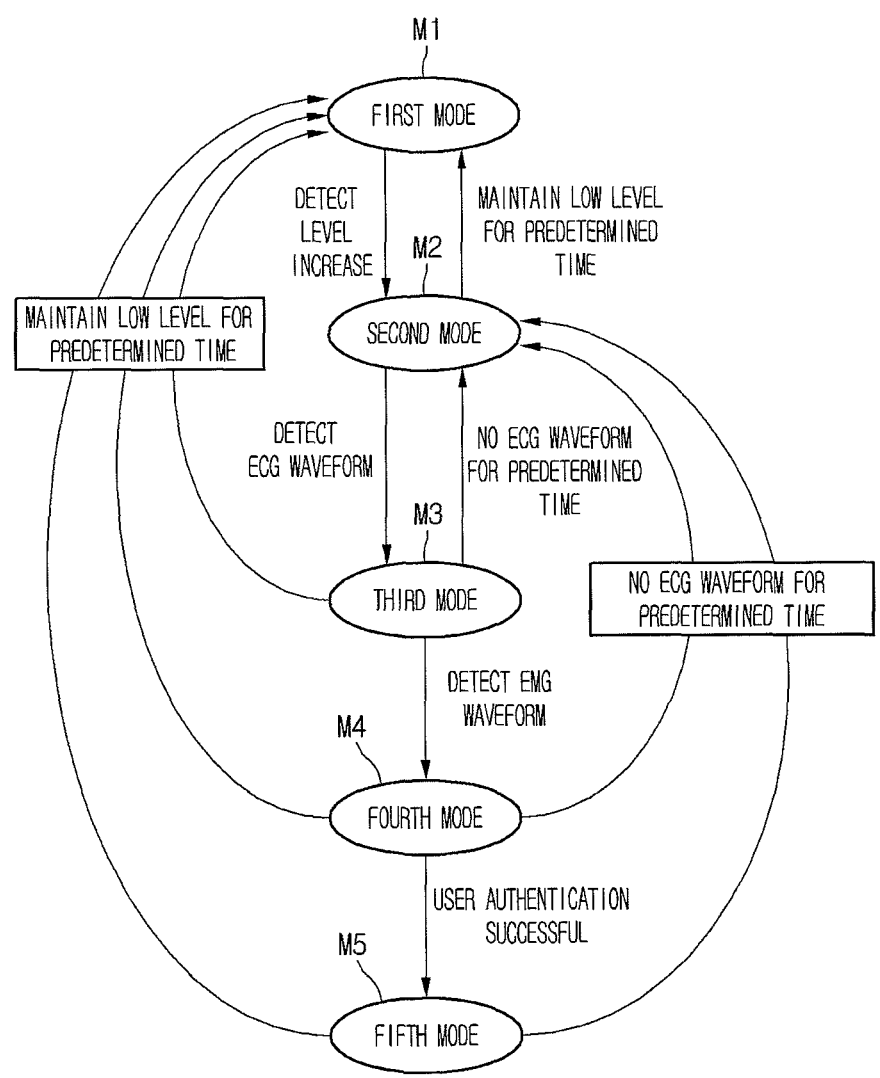
FIG. 26 is a mode changing graph according to an embodiment.

FIG. 26 is a mode changing graph according to an embodiment.

As shown in FIG. 26, when a DC level increase of an ECG signal is detected in the first mode M1, the control unit 180 changes the first mode M1 into the second mode M2.

Once an ECG waveform occurs in the second mode M2, the control unit 180 changes the second mode M2 into the third mode M3. When the DC level of an ECG signal maintains a low level for a predetermined time in the second mode M2, the control unit 180 changes the second mode M2 into the first mode M1.

Once an EMG waveform occurs in the second mode M2, the control unit 180 changes the second mode M2 into the third mode M3. When the DC level of an ECG signal maintains a low level for a predetermined time in the third mode M3, the control unit 180 changes the third mode M3 into the first mode M1. If an ECG waveform is not detected for a predetermined time in the third mode M3, the control unit 180 changes the third mode M3 into the second mode M2.

Once an ECG waveform occurs in the fourth mode M4, the control unit 180 performs user authentication, and if it is successful, changes the fourth mode M4 into the fifth mode M5. When the DC level of an ECG signal maintains a low level for a predetermined time in the fourth mode M4, the control unit 180 changes the fourth mode M4 into the first mode M1. If an ECG waveform is not detected for a predetermined time in the fourth mode M4, the control unit 180 changes the fourth mode M4 into the second mode M2.

When the DC level of an ECG signal maintains a low level for a predetermined time in the fifth mode M5, the control unit 180 changes the fifth mode M5 into the first mode M1. If an ECG waveform is not detected for a predetermined time in the fifth mode M5, the control unit 180 changes the fifth mode M5 into the second mode M2.

According to an embodiment, if user authentication is successful through an ECG signal and an EMG waveform occurs in the third mode M3, the control unit 180 changes the third mode M3 into the fourth mode M4. In this case, since the user authentication is performed, the control unit 180 may not perform user authentication in the fourth mode M4.

In the above, the first mode M1, the second mode M2, the third mode M3, the fourth mode M4, and the fifth mode M4 are mentioned, but some of them may be omitted. That is, according to an embodiment, the first mode M1 may be omitted. According to an embodiment, the fourth mode M4 may be omitted. According to an embodiment, the fifth mode M5 may be omitted. According to an embodiment, the third mode M3 and the fourth mode M4 may be omitted.

Additionally, at least two modes of the above modes may be combined to constitute one mode. According to an embodiment, the first mode M1 and the second mode M2 may be combined. According to an embodiment, the second mode M2 and the third mode M3 may be combined. According to an embodiment, the third mode M3 and the fourth mode M4 may be combined.

Furthermore, some changing paths may be omitted. For example, a changing path from the third mode M3 into the first mode M1 may be omitted.

A condition for changing one mode to another mode may be changed.

According to an embodiment, modes may be divided based on before and after an EMG waveform occurs. At this point, if a previous mode corresponds to a terminal lock state and a subsequent mode corresponds to a terminal unlock state, a user may unlock the terminal by squeezing it. Additionally, if a previous mode corresponds to a sleep state and a subsequent mode corresponds to a wake state, a user may wake the terminal by squeezing it. If a previous mode corresponds to a call reception state and a subsequent mode corresponds to a call state, a user may make a call by squeezing the terminal. If a previous mode corresponds to a message reception state and a subsequent mode corresponds to a message displaying state, a user may confirm the message by squeezing the terminal. If a previous mode corresponds to an application standby state and a subsequent mode corresponds to an application execution state, a user may execute the application by squeezing the terminal Additionally, if a previous mode corresponds to a content's one interval playback state and a subsequent mode corresponds to a content's next interval playback state, a user may turn a page over, display the next image, or play the next music, by squeezing the terminal.

Figure 27:
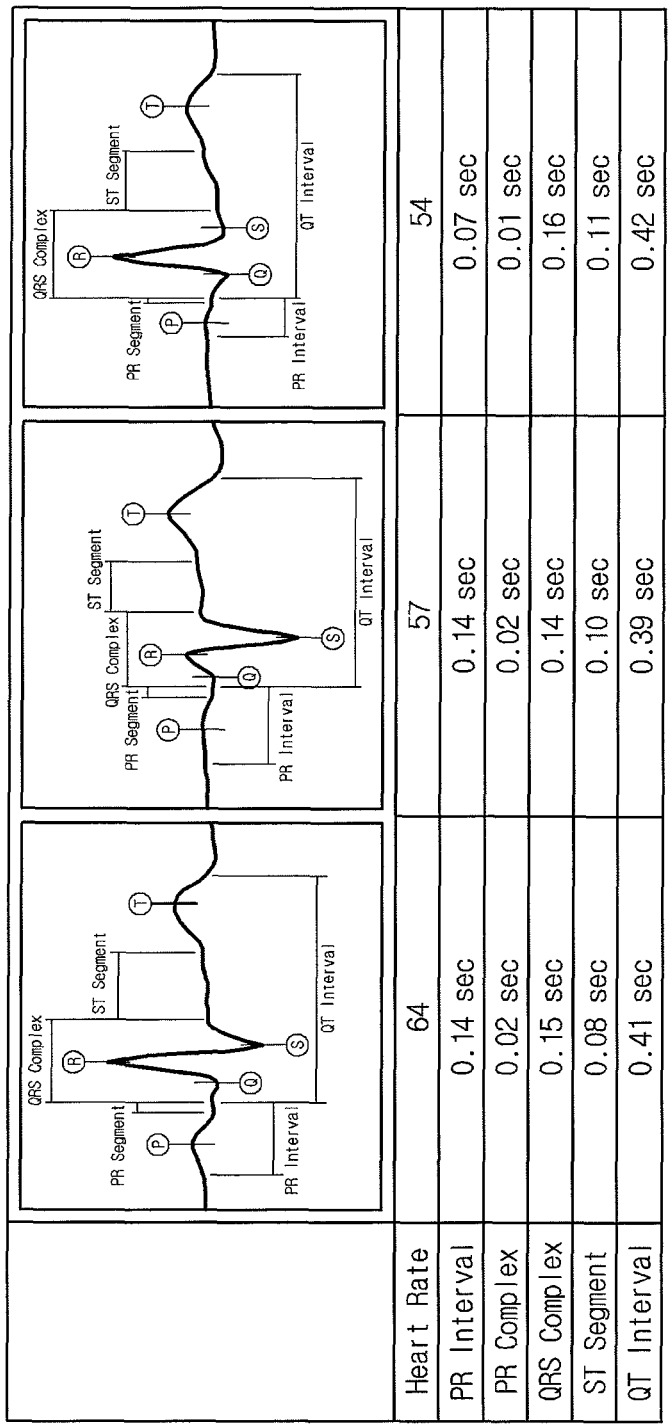
FIG. 27 is a view of an ECG pattern according to an embodiment.

FIG. 27 is a view of an ECG pattern according to an embodiment.

As shown in FIG. 27, an ECG signal includes a P point, a Q point, an R point, an S point, and a T point. Through these, several segments such as a heart rate, PR interval, PR complex, QRS complex, ST segment, and QT interval may be extracted from an ECG signal. Some segments are unique to each other. Accordingly, the portable terminal 100 may obtain an ECG pattern from the segments, and may perform ECG authentication through the obtained ECG pattern. As the segments are increased, security may be enhanced further.

Figure 28:
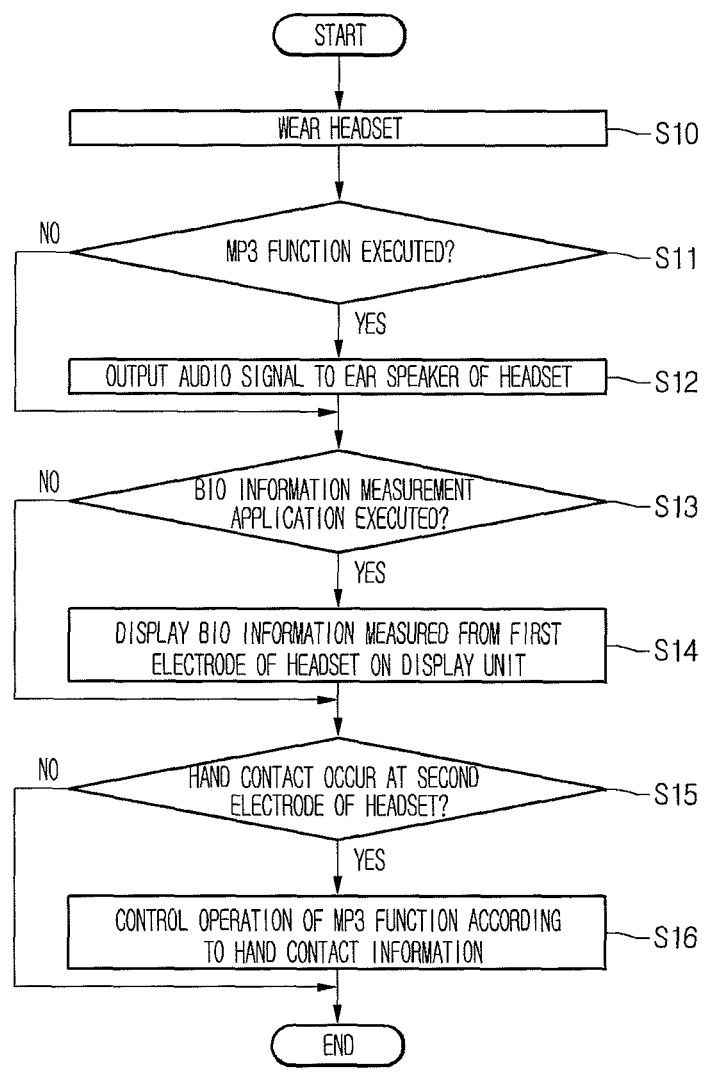
FIG. 28 is a flowchart illustrating a method of controlling an operation of a portable terminal according to an embodiment.

FIG. 28 is a flowchart illustrating a method of controlling an operation of a portable terminal according to an embodiment.

As shown in FIG. 28, it is assumed that the portable terminal 100 operates in linkage with an ear accessory such as the headset 51 or the headphone 300, and the ear accessory includes an ear speaker, an ear contact ECG electrode, and a hand contact ECG electrode. The ear accessory may be connected to the portable terminal 100 wire/wirelessly.

First, the control unit 180 detects that a user wears an ear accessory through an ear contact ECG electrode in operation S10. At this point, while audio is outputted through the speaker of the portable terminal 100, the control unit 180 stops the audio output through the speaker and outputs audio through the ear speaker of the ear accessory.

When a user executes a music application, i.e. an MP3 function, after wearing the ear accessory in operation S11, the control unit 180 outputs an audio signal outputted from an audio codec to the ear speaker of the ear accessory in operation S12. At this point, when the control unit 180 detects that a user removes the ear accessory through the ear contact ECG electrode of the ear accessory, it may pause audio playback, or may output audio through the speaker of the portable terminal 100 after stopping the audio output through the ear speaker of the ear accessory.

While audio is outputted through the ear accessory, a user selects a bio information related application, i.e. an ECG related application, from a menu, and executes it in operation S13. Then, the control unit 180 receives the ECG signal, detected through the ear contact ECG electrode of the ear accessory, by using the earphone jack 176 and the ECG sensor, and displays information, obtained from the ECG signal, and the ECG signal on the display unit 151 in operation S14. Accordingly, according to an embodiment, listening to music and ECG measurement may be performed simultaneously by using the ear accessory.

Then, when detect signals Hand_R and Hand_L are received through the earphone jack 176 in operation S15 after the user's hand contacts the hand contact ECG electrode at the outside of the ear accessory, the control unit 180 determines a hand contact type through the contact sensing unit and controls audio playback (for example, Play, Forward, Reverse, Pause, and others) according to hand contact information in operation S16. Especially, the control unit 180 controls audio playback according to Table 1.

Moreover, when an audio function is not executed with the ear accessory put on and the ECG related application is executed in operations S10 and S13, the control unit 180 receives the ECG signal, detected from the ear contact ECG electrode of the ear accessory, through the earphone jack 176 and the ECG sensor, and displays information obtained from the ECG signal or the ECG signal on the display unit 151 in operation S14. Accordingly, in this case, only an ECG measurement function is performed by using the ear accessory.

Then, a usage case of a mode changing method of a portable terminal according to an embodiment will be described with reference to FIGS. 29 to 38.

Figure 29:
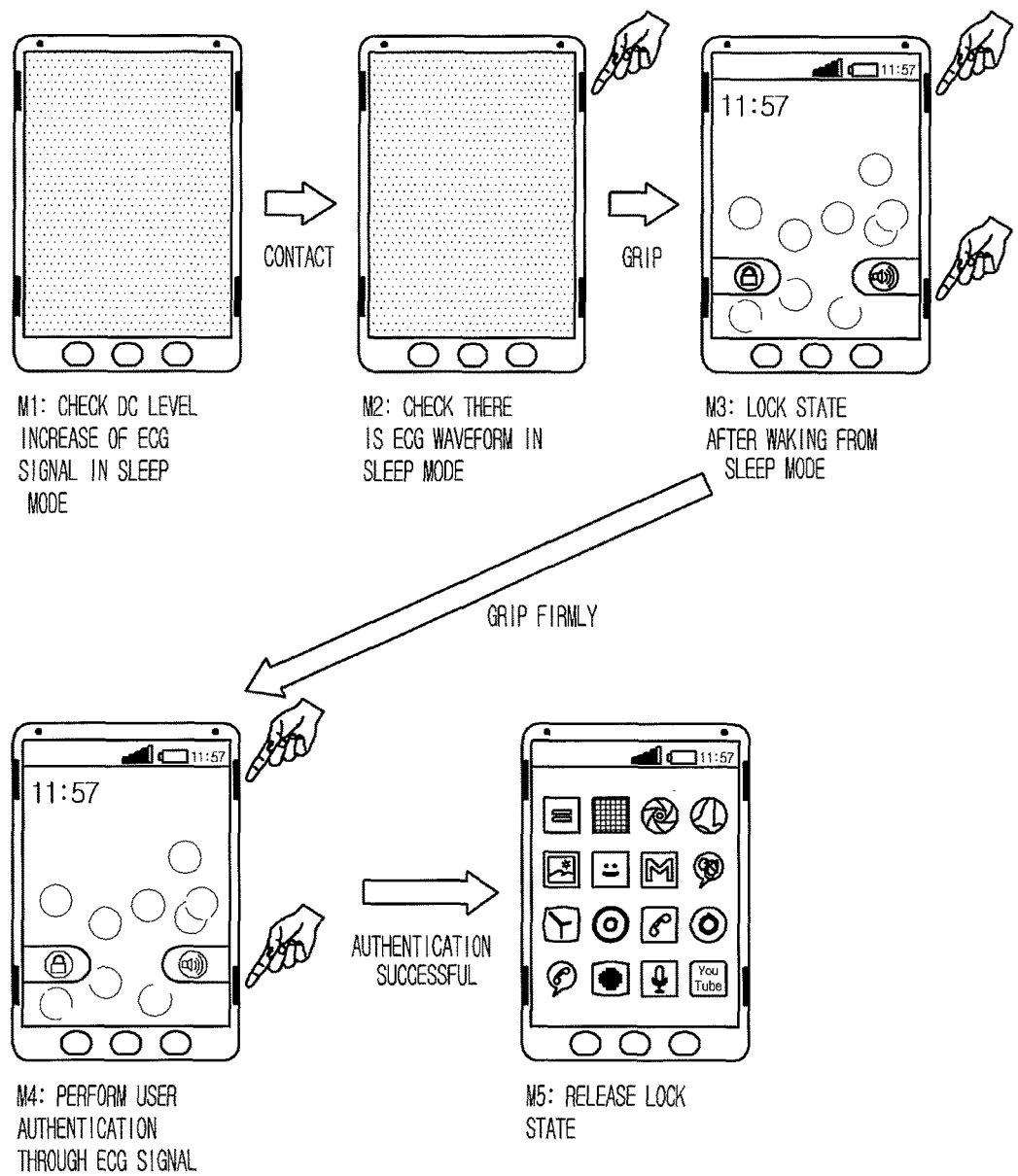
FIG. 29 is a view illustrating a process for releasing a lock state according to an embodiment.

FIG. 29 is a view illustrating a process for releasing a lock state according to an embodiment.

First, the portable terminal 100 checks a DC level increase of an ECG signal in a sleep mode during a first mode M1. When the body does not contact the electrode, the portable terminal 100 only need to check a DC level increase of an ECG signal without checking whether there is an ECG waveform, so the power consumption of the portable terminal 100 may be reduced in the sleep mode.

When a user's finger contacts one of the plurality of ECG electrodes 171, the portable terminal 100 changes into the second mode M2 in order to check whether there is the ECG waveform in the sleep mode.

When a user grips the portable terminal 100 in the second mode M2 in which whether there is the ECG waveform is checked, the portable terminal 100 changes into the third mode M3 and wakes up from the sleep mode in order to display a lock state screen. When a predetermined time elapses after a user puts the portable terminal 100 down in the second mode M2, the portable terminal 100 changes into the first mode M1 in order to check a DC level increase of an ECG signal in a sleep mode.

When a user grips the portable terminal 100 in the third mode M3 in which the lock state screen is displayed, the portable terminal 100 changes into the fourth mode M4 in order to perform user authentication through an ECG signal. When a predetermined time elapses after a user puts the portable terminal 100 down in the third mode M3, the portable terminal 100 changes into the first mode M1 in order to check a DC level increase of an ECG signal in a sleep mode. When a predetermined time elapses after a user does not squeeze the portable terminal 100 and thus the finger contacts one of the plurality of ECG electrodes 171, the portable terminal 100 changes into the second mode M2 in order to check whether there is an ECG waveform in a sleep mode.

If the user authentication is successful in the fourth mode M4, the portable terminal 100 changes into the fifth mode M5 in order to release the lock state. When a predetermined time elapses after a user puts the portable terminal 100 down in the fourth mode M4, the portable terminal 100 changes into the first mode M1. When a predetermined time elapses after a user does not squeeze the portable terminal 100 and thus the finger contacts one of the plurality of ECG electrodes 171, the portable terminal 100 changes into the second mode M2.

When a predetermined time elapses after a user puts the portable terminal 100 down in the fifth mode M5 in which the lock state is released, the portable terminal 100 changes into the first mode M1. When a predetermined time elapses after a user does not squeeze the portable terminal 100 and thus the finger contacts one of the plurality of ECG electrodes 171 in the fifth mode M5, the portable terminal 100 changes into the second mode M2.

Figure 30:
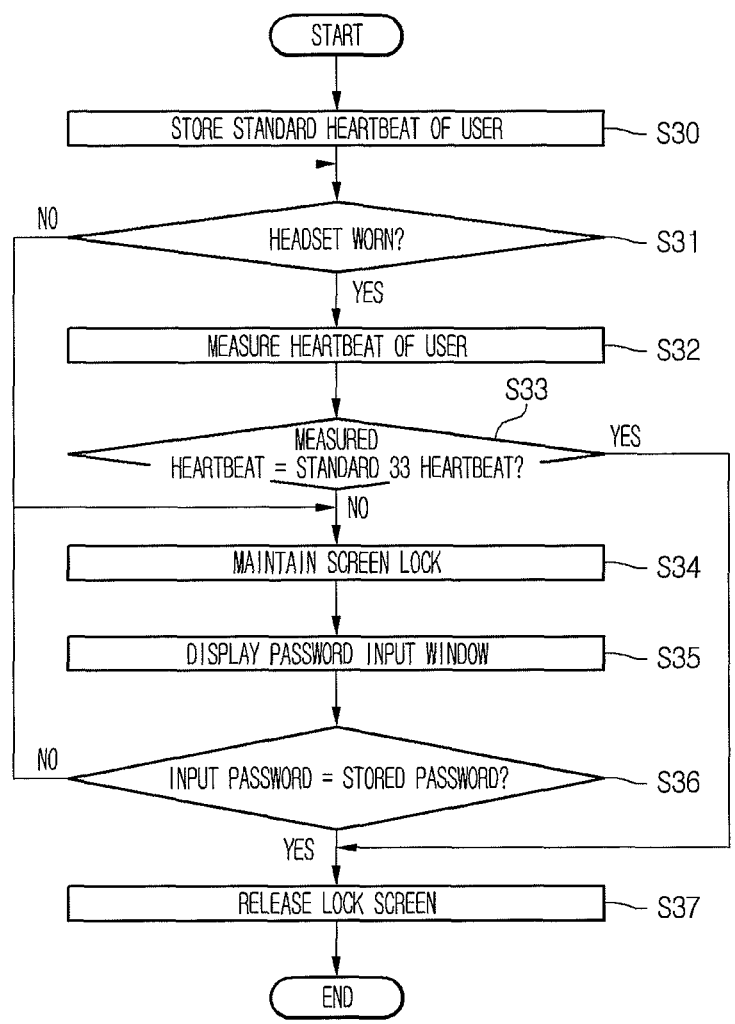
FIG. 30 is a flowchart illustrating a process for releasing a lock state according to another embodiment.

FIG. 30 is a flowchart illustrating a process for releasing a lock state according to another embodiment. Especially, FIG. 30 shows an example for releasing a screen lock by measuring a user's heartbeat.

As shown in FIG. 30, the control unit 180 measures the heartbeat of a user and stores it in the memory 160 in operation S10. Then, when the user wears an ear accessory, the control unit 180 confirms the current heartbeat of the user through an ECG signal detected from the ear contact ECG electrode of the ear accessory in operation S32.

Then, the control unit 180 compares the confirmed current heartbeat with a pre-stored reference heartbeat in operation S33, and if they are identical, the screen lock is released in operation S37. However, if the two heartbeats are not identical, the screen lock state is maintained in operation S34, and a password input window for inputting a password is displayed on the display unit 151 in operation S35. Then, if a password inputted in the password input window is identical to a pre-stored password, the control unit 180 releases the screen lock in operation S37. If they are identical, the screen lock state is maintained in operation S34.

As mentioned above, according to an embodiment, with an ECG sensor equipped in a wire/wireless headset or an ECG sensor, a user may measure ECG naturally while listening to music. By contacting one side of the headset by the hand, audio playback may be controlled or operation controls (for example, call reception and lock control) of various portable terminals may be performed.

Figure 31:
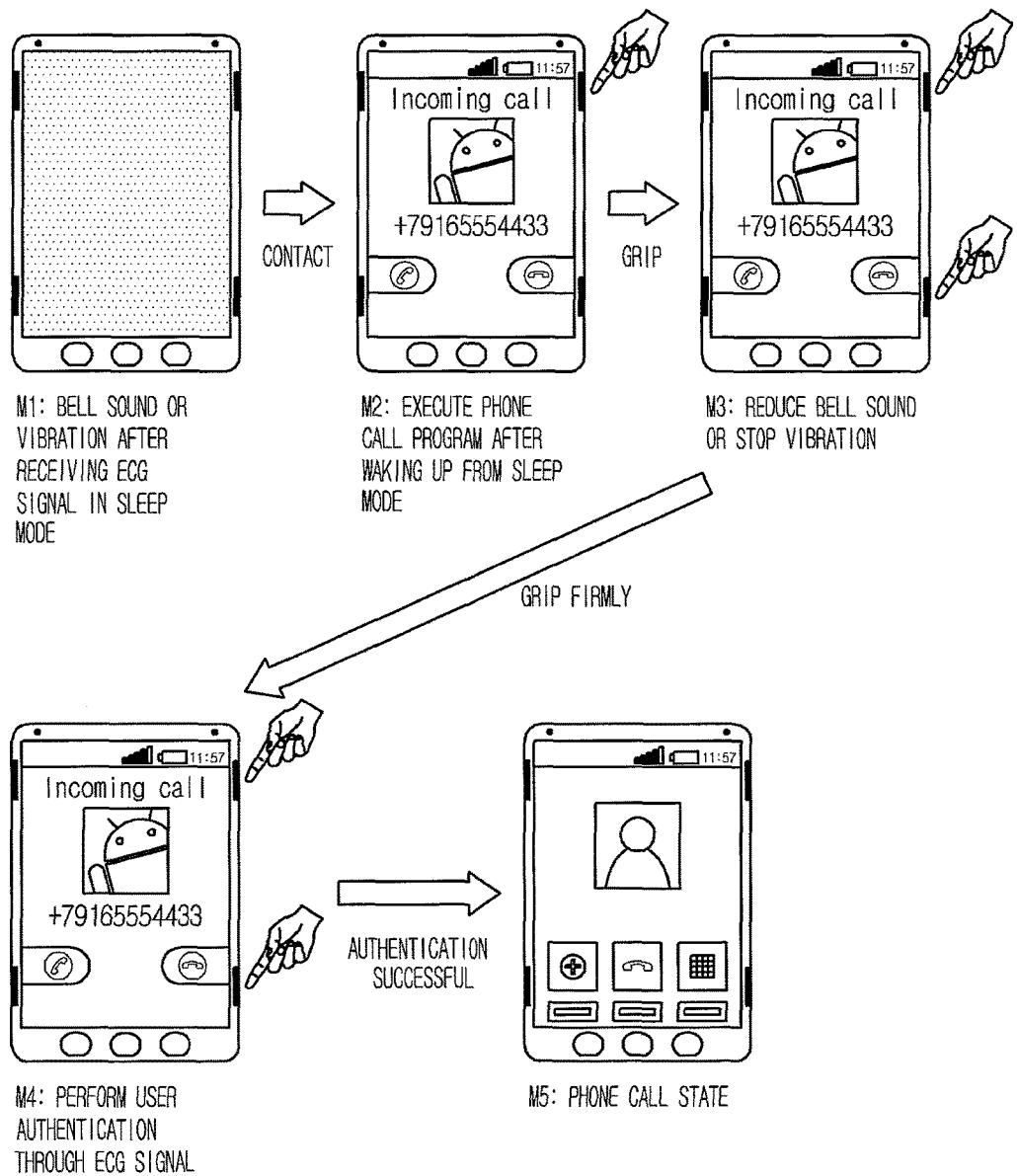
FIG. 31 is a view illustrating a process for making a call according to an embodiment.

FIG. 31 is a view illustrating a process for making a call according to an embodiment.

First, the portable terminal 100 plays bell sound, or generates vibration by receiving a call in a sleep mode during a first mode M1.

When a user's finger contacts one of the plurality of ECG electrodes 171 in the first mode M1, the portable terminal 100 changes into the second mode M2 in order to wake up and executes a phone call program.

When a user grips the portable terminal 100 in the second mode M2, the portable terminal 100 changes into the third mode M3 in order to reduce the volume of the bell sound, stop the bell sound playback, or stop the vibration.

When a user grips the portable terminal 100 in the third mode M3, the portable terminal 100 changes into the fourth mode M4 in order to perform user authentication through an ECG signal.

If the user authentication is successful, the portable terminal 100 changes into the fifth mode M5 in order to start a phone call.

Figure 32:
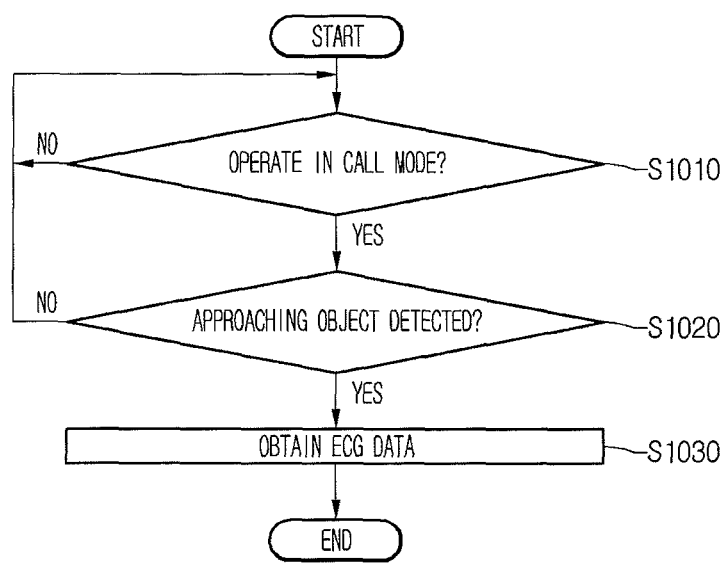
FIG. 32 is a flowchart illustrating a method of controlling an operation of a portable terminal according to an embodiment.

FIG. 32 is a flowchart illustrating a method of controlling an operation of a portable terminal according to an embodiment.

The control unit 180 recognizes whether the portable terminal 100 enters a call mode in operation S1010.

While the portable terminal 100 enters the call mode, in case that an object adjacent to a specific region of the body of the portable terminal 100 is detected in operation S1020, the control unit 180 obtains ECG data through the ECG electrode 171 in operation S1030.

In operation S1020, an object adjacent to the specific region of the body of the portable terminal 100 may be detected by the proximity sensor 141. Moreover, the specific region where the adjacent object is detected is a region having the sound outputting module 152 that operates as a speaker for outputting a call sound during a call mode. That is, an object adjacent to the sound outputting module 152 may be detected in operation S1020 through the proximity sensor 141 adjacent to the sound outputting module 152.

Moreover, in operation S1020, when detecting an object adjacent to the specific region of the body of the portable terminal 100 through the proximity sensor 141, the control unit 180 transmits a control signal to the switch 310 in order to connect the ECG sensor 142*c* with the ECG electrode 171 at the body of the portable terminal 100. Especially, the control unit 180 transmits a control signal to the switch 310 in order to connect the ECG sensor 142*c* adjacent to the sound outputting module 152 with the ECG electrode 171 at the body of the portable terminal 100.

Moreover, as shown in FIG. 32, only when the portable terminal 100 enters the call mode and an object adjacent to a specific region of the body of the portable terminal 100 is detected, ECG data are obtained from the control unit 180. However, the present invention is not limited thereto.

According to the present invention, when a user uses an ear accessory such as the headset 50 or the earphone 300, i.e. an ear accessory is attached to the portable terminal 100, the control unit 180 may obtain ECG data even if an object adjacent to a specific area of the body of the portable terminal 100 is not detected. In this case, when entering a call mode, the control unit 180 transmits a control signal to the switch 310 in order to connect the ECG sensor 142*c* with the ECG electrode 171 at the body of the portable terminal 100. Then, when the ear accessory has an ECG electrode, the control unit 180 transmits a control signal to the switch 310 in order to the ECG sensor 142*c* with the ECG electrode of the ear accessory.

Figure 33:
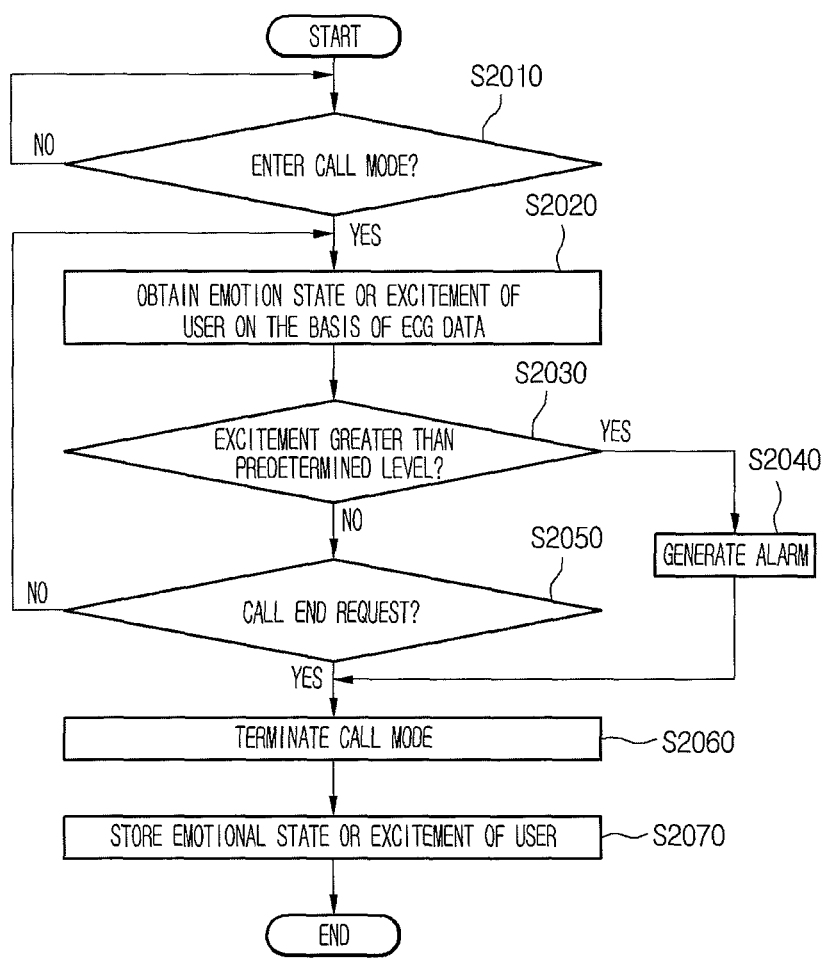
FIG. 33 is a flowchart illustrating a method of determining whether to end a call of a portable terminal according to another embodiment.

FIG. 33 is a flowchart illustrating a method of determining whether to end a call of a portable terminal according to another embodiment.

Referring to FIG. 33, when the portable terminal 180 enters a call mode in operation S2010, the control unit 180 analyzes ECG data obtained from the ECG sensor 142*c*, and obtains an emotional state or excitement of a user in operation S2020. At this point, the control unit 180 obtains feature parameters, which are criteria for determining an emotional state or excitement of a user, from ECG data through the analysis of the ECG data, in order to obtain the emotional state or excitement of a user from the feature parameters. The feature parameters may be a peak value of an ECG signal and a heart rate or a cardiac cycle, which is obtained by using the peak value of the ECG signal.

If the user's excitement obtained in operation S2020 is greater than the predetermined level in operation S2030, the control unit 180 outputs an alarm that notifies the user's excitement state in operation S2040. Additionally, the control unit 180 may end a call with the other party in order for the stability of a user in operation S2060.

An alarm that notifying a user's excitement state may be outputted in various forms.

For example, if the user's excitement is greater than the predetermined level, the control unit 180 may transmit a guide sound that notifies the user's excitement to the other side.

Additionally, for example, if the user's excitement is greater than the predetermined level, the control unit 180 may output a guide sound or a vibration sound that notifies the user's excitement to a user, or may display a warning message on the display module 151.

Furthermore, when the user's excitement is greater than the predetermined level, a call is terminated compulsorily as shown in FIG. 33, but the present invention is not limited thereto.

According to the present invention, if the user's excitement is greater than the predetermined level, the control unit 180 may output an alarm that notifies a user's state and may not terminate the call.

Moreover, according to the present invention, if the user's excitement is greater than the predetermined level, the control unit 180 may store a call history to the other side in the memory 160.

Again, referring to FIG. 33, if call termination is requested from a user in operation S2050, or a call mode is terminated when the user's excitement is greater than the predetermined level, the control unit 180 a user's emotions state or excitement in the memory 160 in operation S2070.

For example, the control unit 180 may include a user's emotional state or excitement obtained by a call mode in the call history, and then, may store it.

Furthermore, for example, the control unit 180 may match the user's emotional state or excitement obtained in a call mode to the contact information of the other side, and then, may store it.

Figure 34:
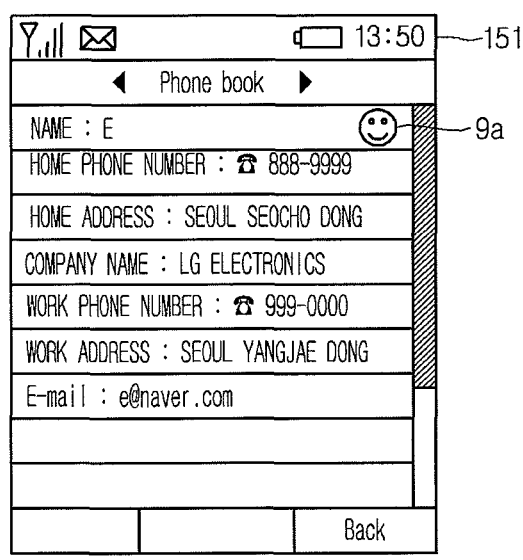
FIG. 34 is a view when a user's emotional state is matched to the contact information of the other side call and is stored in a phone book.

FIG. 34 is a view when a user's emotional state is matched to the contact information of the other side call and is stored in a phone book.

Referring to FIG. 34, as a call with the other side A is terminated, the control unit 180 matches to the contact information of the other side A an emotional state (for example, feels good) that a user feels about the other side A during a call and stores it in a phone book.

Then, when the control unit 180 reads the contact information of the other side A from the phone book and displays it on a screen, the stored emotional state 9*a* of the user is additionally read and displayed on the same screen. The user's emotional state may be represented with various forms such as emoticon and text. FIG. 34 is a view when a user's emotional state is represented with an emoticon form.

Additionally, if information on a user's emotional state or excitement for the other side is already stored, the control unit 180 may update the user's emotional state or excitement by using the currently-obtained emotional state or excitement.

Moreover, the control unit 180 may continuously store a user's emotional state or excitement obtained during a call mode.

Figure 35:
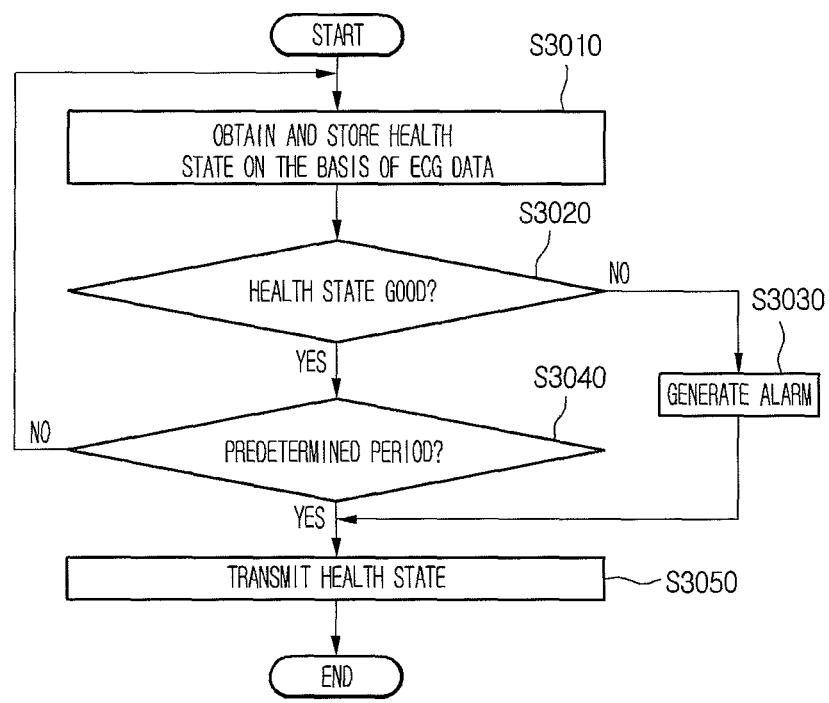
FIG. 35 is a view illustrating a method of managing a user's health state by using ECG data in a portable terminal 100 according to an embodiment.

FIG. 35 is a view illustrating a method of managing a user's health state by using ECG data in a portable terminal 100 according to an embodiment.

Referring to FIG. 35, the control unit 180 obtains the user's health state on the basis of the user's ECG data obtained through the ECG sensor 142*c* in operation S3010.

The control unit 180 obtains feature parameters such as a peak value, a heart rate, and a cardiac cycle, which are criteria for determining a user's health state, from the ECG data through an analysis of ECG data. Moreover, the control unit 180 obtains a user's health state on the basis of the feature parameters.

Additionally, the control unit 180 stores the obtained ECG data and health state in the memory 160. The user's ECG data and health state may be stored in addition to the time and position at which they are obtained.

The control unit 180 confirms the user's health state on the basis of the obtained health state, and if it is determined that the user's health state is poor in operation S3020, generates an alarm in operation S3030.

For example, the control unit 180 outputs guide sound or vibration sound, which notifies the health state abnormality to the user, or displays a message, which notifies the health state abnormality through the display module 151.

Moreover, for example, the control unit 180 transmits a message notifying a user's health state abnormality or user's health state information by using a predetermined phone number.

Again, referring to FIG. 35, even if it is determined that the user's health state is normal, when it comes to a predetermined period in operation S3040, the control unit 180 transmits the user's health state including the obtained ECG data, heart rate, and cardiac period to the predetermined other side by using the phone number and e-mail address of the predetermined other side in operation S3050.

In operation S3020, the control unit 180 compares the previously-obtained ECG data heart rate, and cardiac period with the currently-obtained ECG data heart rate, and cardiac period, and if there is a great change, determines that the user's health abnormality occurs.

Moreover, in operation S3020, the control unit 180 compares the obtained ECG data heart rate, and cardiac period with the predetermined level, and if they are out of the predetermined range, determines that the user's health abnormality occurs.

According to an embodiment, the user's ECG data obtained through the ECG sensor 142*c* may be used in various fields in addition to the above-mentioned call mode control and health state management.

For example, the control unit 180 obtains the user's emotional state from the ECG data obtained through the ECG sensor 142*c*, and then, stores them combined with the current position of the portable terminal 100. The health state combined with the position information and stored may be used for criteria for searching specific position information such as famous restaurants and providing it to a user. For example, restaurants having a negative rating of a user's emotional state may be excluded from a famous restaurant list that recommended to a user. Furthermore, for example, restaurants having a positive rating of a user's emotional state may be recommended first to a user.

Furthermore, for example, the control unit 180 obtains the user's emotional state from the ECG data through the ECG sensor 142*c*, and then, selectively provides only specific position information matching the user's emotional state to a user.

Furthermore, for example, the control unit 180 obtains the user's emotional state from the ECG data or stress index through the ECG sensor 142*c*, and then, recommends specific content to a user on the basis of them. When a user shows a negative emotional state or a high stress index, the control unit 18 may recommend or provide specific kinds of contents that help user's stability or refresh to the user. Here, the contents provided for user's stability or refresh may be set by a user.

Moreover, according to the above embodiment, a case that a user's ECG signal is measured when the portable terminal 100 operates in a call mode was described but the present invention is not limited thereto. According to the present invention, the control unit 180 may be applicable to measuring a user's ECG signal when a user requests ECG signal measurement through the user input unit 130.

According to the above-mentioned embodiment, a portable terminal may measure user's ECG signal without additional electronic device or equipment. Furthermore, a portable terminal, which performs various functions in addition to an ECG signal measurement function, activates ECG signal measurement only in a designated mode, so that power consumption for ECG signal measurement may be minimized. Furthermore, when the portable terminal does not operate in a call mode, electrodes are electrically separated from a signal processing unit. Therefore, noise from an external, which flows through electrodes, may be minimized and an internal circuit may be protected.

Figure 36:
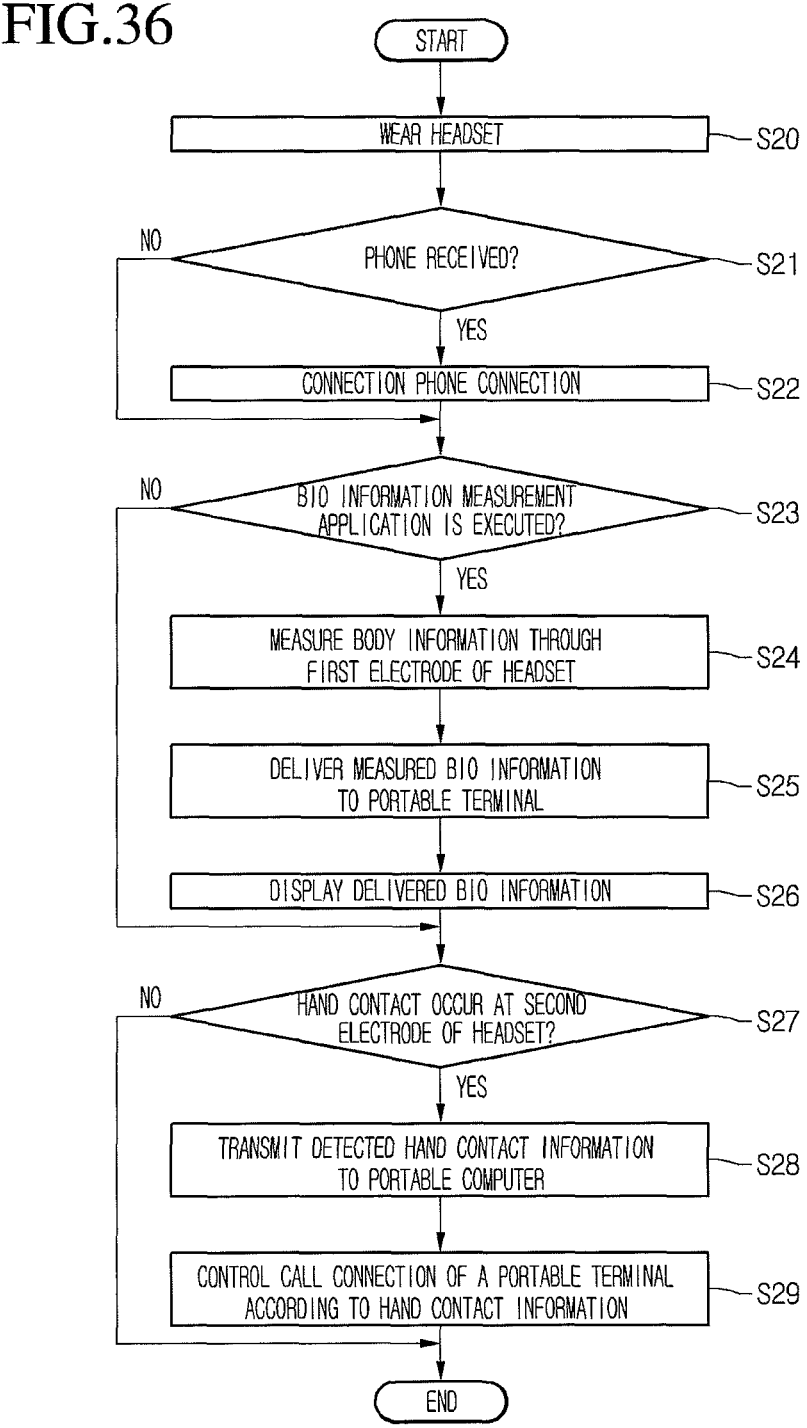
FIG. 36 is a flowchart illustrating a method of controlling an operation of a portable terminal according to another embodiment.

FIG. 36 is a flowchart illustrating a method of controlling an operation of a portable terminal according to another embodiment. The embodiment of FIG. 36 relates to a process of call reception instead of an MP3 function, and its basic operation is similar to that of the embodiment of FIG. 28.

That is, when a call is received with the headset being worn by a user, the control unit 180 automatically connects a phone call in operation S20 to S22 While a user selects a bio information measurement application, i.e. an ECG measurement application, from a menu, and executes it in operation S23, the control unit 180 receives the ECG signal, detected from the ear contact electrode of the ear accessory, through the earphone jack 176 and the ECG sensor, and displays information, obtained from the ECG signal, and the ECG signal on the display unit 151 in operations S23 to S26. Accordingly, the present invention may measure ECG during a phone call by using the headset.

Then, when detect signals Hand_R and Hand_L are received through the earphone jack 176 in operations S27 and 28 after the user's hand contacts the hand contact electrode 50b of the ear accessory, the control unit 180 determines a hand contact type through the contact sensing unit and controls the phone call connection (for example, call connection and call waiting) according to hand contact information in operation S29.

Figure 37:
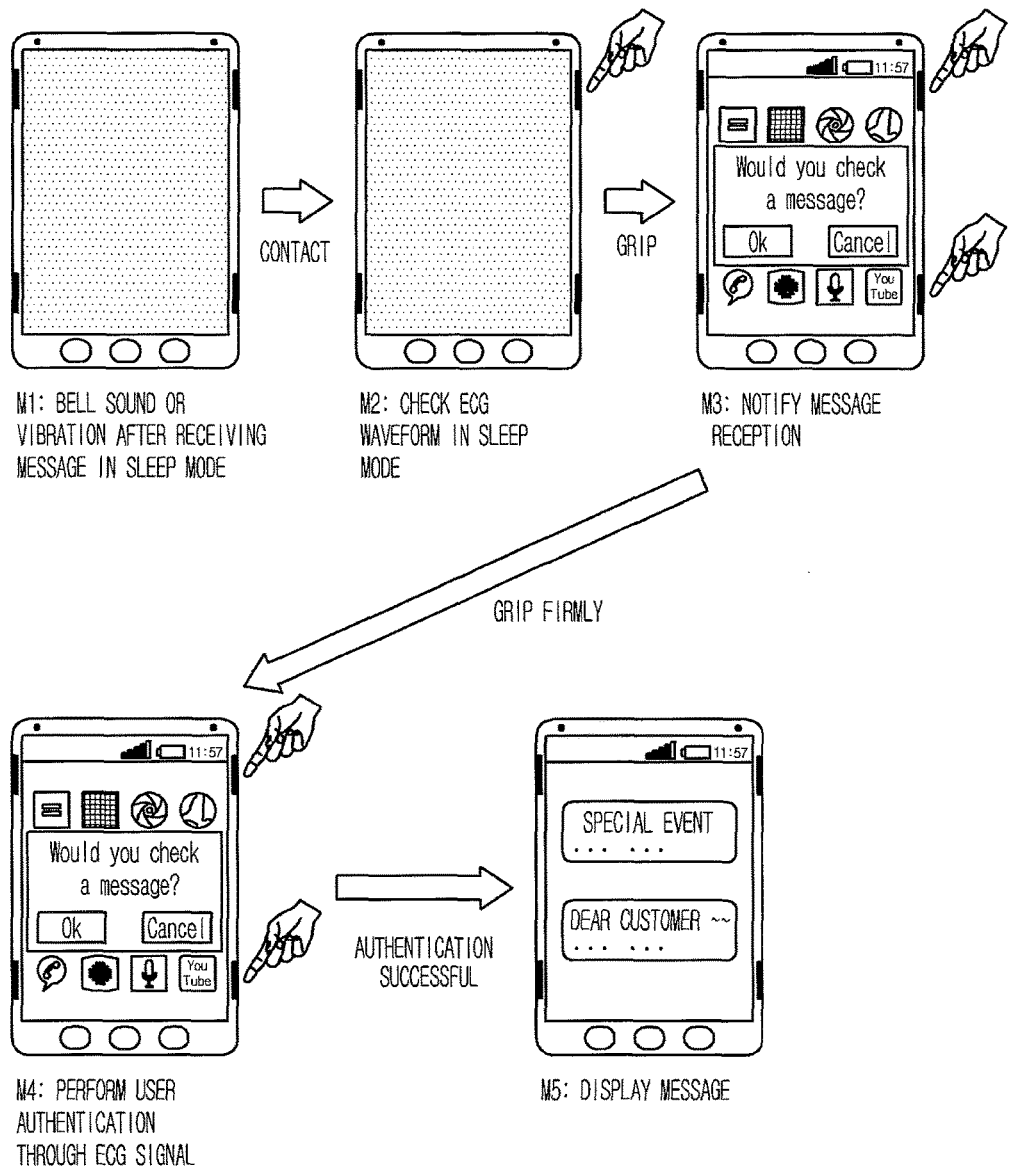
FIG. 37 is a view illustrating a process for confirming message content according to an embodiment.

FIG. 37 is a view illustrating a process for confirming message content according to an embodiment.

First, the portable terminal 100 plays bell sound, or generates vibration by receiving a message in a sleep mode during a first mode M1.

When a user's finger contacts one of the plurality of ECG electrodes 171 in the first mode M1, the portable terminal 100 changes into the second mode M2 in order to check an ECG waveform in the sleep mode.

When a user grips the portable terminal 100 in the second mode M2, the portable terminal 100 changes into the third mode M3 in order to display a message reception alarm.

When a user squeezes the portable terminal 100 in the third mode M3, the portable terminal 100 changes into the fourth mode M4 in order to perform user authentication through an ECG signal.

If the user authentication is successful, the portable terminal 100 changes into the fifth mode M5 in order to display the received message.

Figure 38:
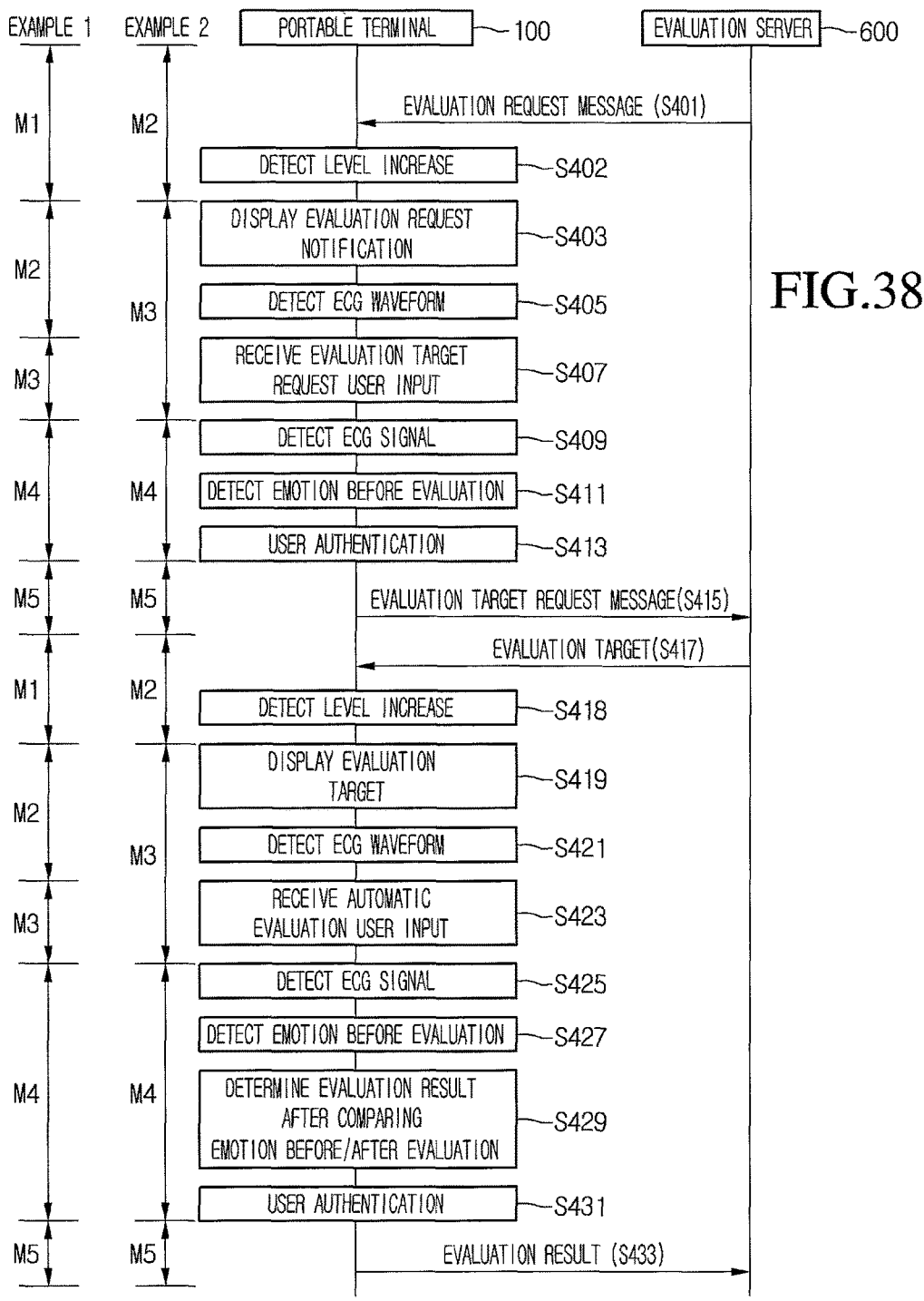
FIG. 38 is a ladder diagram illustrating a method of evaluating an evaluation target through an emotion sensed from an ECG signal according to an embodiment.

FIG. 38 is a ladder diagram illustrating a method of evaluating an evaluation target through an emotion sensed from an ECG signal according to an embodiment.

The evaluation target may correspond to figures, pictures, comments, and news articles.

FIG. 38 is described based on an ECG signal, but another body signal may be used.

First, the evaluation server 600 transmits an evaluation request message to the portable terminal 100.

The control unit 180 senses a DC level increase of an ECG signal in operation S402. According to an embodiment, the control unit 180 may sense an ECG waveform.

When the DC level of an ECG signal is sensed, the control unit 180 of the portable terminal 100 displays an evaluation request alarm in operation S403.

After the evaluation request alarm is displayed, the control unit 180 senses an ECG waveform in operation S405. Operation S405 may be omitted.

The control unit 180 receives an evaluation target request user input in operation S409. The evaluation target request user input may correspond to an EMG waveform.

When the evaluation target request user input is displayed, the control unit 180 detects an ECG waveform in operation S409.

In operation S411, the control unit 180 detects an emotion before evaluation from the ECG signal detected in operation S409.

The control unit 180 confirms whether a pattern of the ECG signal detected in operation S409 is identical to that registered by a user of the portable terminal 100, and then, performs user authentication in operation S413.

If the user authentication is successful, the control unit 180 transmits an evaluation target request message to the evaluation server 600 through a communication module in operation S415.

According to an embodiment, when operations S401 to S407 and operation S413 are omitted, the control unit 180 detects a touch of an evaluation target link in order to transmit an evaluation target request message.

The evaluation server 600 transmits an evaluation target in response to the evaluation target request message in operation S417.

The control unit 180 detects a DC level increase of an ECG signal in operation S418. According to an embodiment, the control unit 180 may detect an ECG waveform.

When a DC level of an ECG signal is sensed, the control unit 180 displays the received evaluation target in operation S419.

After the evaluation target is displayed, the control unit 180 detects an ECG waveform in operation S421. Operation S421 may be omitted.

The control unit 180 receives an automatic evaluation user input in operation S423. The automatic evaluation user input may correspond to an EMG waveform.

The control unit 180 detects an ECG signal in operation S425.

In operation S427, the control unit 180 detects an emotion after evaluation from the ECG signal detected in operation S425.

For example, the control unit 180 may determine a user's emotion according to Table 3.

TABLE 3

|  | Beats per minute |
| --- | --- |
| Very excited | 120 over |
| Excited | 90-120 |
| Stable | 50-90 |
| Depressed | 50 below |

The control unit 180 compares the emotion before evaluation with the emotion after evaluation and determines an evaluation result in operation S429. For example, the control unit 180 determines excitement or stability through a change in a pulse frequency and on the basis of this, determines an evaluation result. If an interesting video is an evaluation target, whether the video is funny is determined on the basis of an increased heart rate, compared to a heart rate before watching the video.

The control unit 180 confirms whether a pattern of the ECG signal detected in operation S425 is identical to that registered by a user of the portable terminal 100, and then, performs user authentication in operation S431.

If the user authentication is successful, the control unit 180 transmits an evaluation result to the evaluation server 600 through a communication module in operation S433.

According to an embodiment, operation S401 and operation S402 correspond to the first mode M1; operation S403 and operation S405 correspond to the second mode M2; operation S407 corresponds to the third mode M3; operation S409, operation S411, and operation S413 correspond to the fourth mode M1; and operation S415 corresponds to the fifth mode M5. Additionally, operation S417 and operation S418 correspond to the first mode M1; operation S419 and operation S421 correspond to the second mode M2; operation S423 corresponds to the third mode M3; operation S427, operation S429, and operation S431 correspond to the fourth mode M1; and operation S433 corresponds to the fifth mode M5.

Relations of operations and modes of FIG. 38 may be changed. For example, operation S401 and operation S402 may correspond to the second mode M2; operation S403, operation S405, and operation S407 may correspond to the third mode M3; operation S409, operation S411, and operation S413 may correspond to the fourth mode M4; and operation S415 may correspond to the fifth mode M5. Additionally, operation S417 and operation S418 may correspond to the second mode M2; operation S419, operation S421, and operation S423 may correspond to the third mode M3; operation S425, operation S427, and operation S429 may correspond to the fourth mode M4; and operation S433 may correspond to the fifth mode M5.

A data transmitting method of a portable terminal according to an embodiment will be described with reference to FIGS. 39 to 45.

Figure 39:
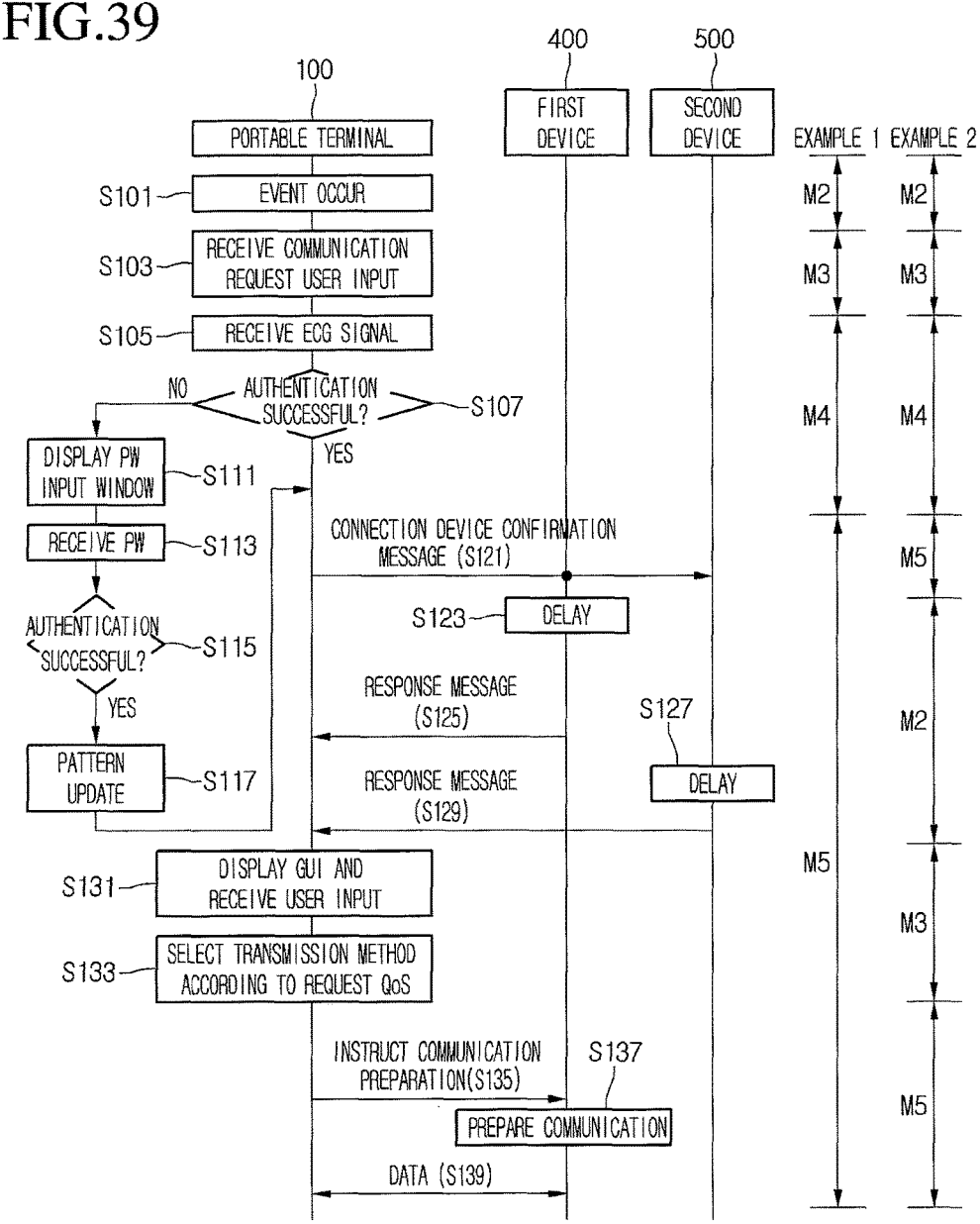
FIG. 39 is a flowchart illustrating a data transmitting method of a portable terminal according to an embodiment.

FIG. 39 is a flowchart illustrating a data transmitting method of a portable terminal according to an embodiment.

As shown in FIG. 39, a portable terminal 100 may communicate with a first device 400 and a second device 500. However, let's assume that the portable terminal communicates with the first device 400.

First, the control unit 180 detects event occurrence in operation S101, and waits to receive an ECG signal. Here, an event may correspond to call reception, program execution, file selection for transmission, device selection for connection, and communication method selection. Here, a program may correspond to a contact related program, a name card related program, a document transmission related program, a music playback program, and a video playback program. A file for transmission may correspond to contacts, name cards, documents, music files and video files.

The control unit 180 receives a communication request user input in operation S103. Here, the communication request user input may correspond to an EMG waveform.

Then, the control unit 180 detects en ECG signal through the ECG sensor 142c.

The control unit 180 recognizes an ECG pattern from the ECG signal, and confirms whether an ECG pattern of a user stored in the memory 160 is identical to the recognized ECG pattern in order to perform ECG authentication in operation S107.

If the user's ECG pattern is not stored in the memory 160 or they are not identical, the control unit 180 displays a password input window on the display unit 151 in operation S111.

The control unit 180 receives a password in operation S113, and confirms whether the received password is identical to a password stored in the memory 160 in order to perform password authentication in operation S115. If the password authentication is failed, the control unit 180 terminates data transmission.

Moreover, if the password authentication is successful, the control unit 180 stores the recognized ECG pattern in the memory 160 in order to perform ECG pattern update in operation S117. The ECG pattern update will be described with reference to FIG. 40.

Figure 40:
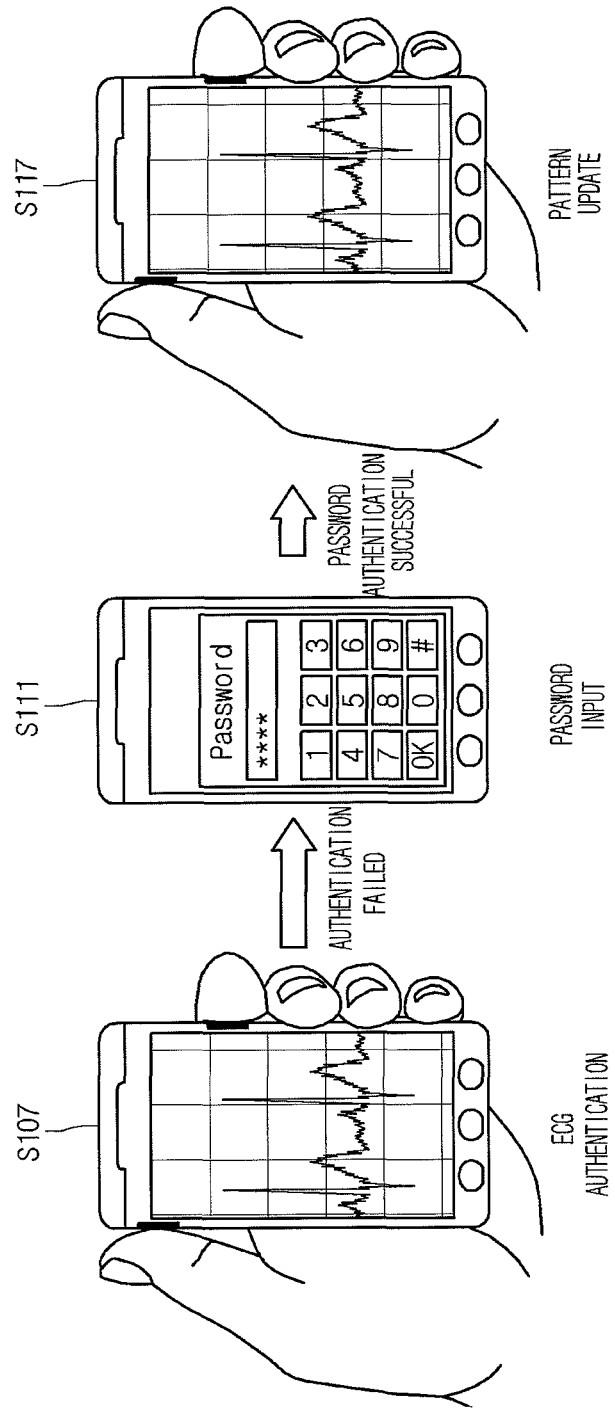
FIG. 40 is a view illustrating a process for ECG pattern update according to an embodiment.

FIG. 40 is a view illustrating a process for ECG pattern update according to an embodiment.

As shown in FIG. 40, a user performs ECG authentication through two electrodes attached to the left and right of the portable terminal 100 in operation S107. However, if the ECG authentication is failed, a password input window is displayed on the display unit 151. The user inputs a password by touching the display unit 151 in operation S111. If the password authentication is successful, the control unit 180 recognizes an ECG pattern in order to perform ECG pattern update in operation S117.

When the ECG authentication is successful or the password authentication is successful, the control unit 180 of the portable terminal 100 transmits a connection device confirmation message to devices around in operation S121. According to an embodiment, the control unit 180 of the portable terminal 100 outputs a connection device confirmation message to devices around through the body communication module 116. According to an embodiment, the control unit 180 transmits a connection device confirmation message through another communication module such as a WLAN communication modem, a Wibro communication modem, an HSDPA communication modem, a Bluetooth communication module, and an infrared communication modem. At this point, if there are more than two devices around, the connection device confirmation message may be transmitted to all the devices 400 around.

Additionally, while a device receiving the connection device confirmation message transmits a response message, if the first device 400 and the second device 500 transmit the response message, conflict may occur. Accordingly, the first device 400 determines delay time through a random function in operation S123, and transmits a response message to the portable terminal 100 after a predetermined delay time elapses in operation S125. Also, the second device 500 determines delay time through a random function in operation S127, and transmits a response message to the portable terminal 100 after a predetermined delay time elapses in operation S129.

The devices around may transmit a response message through a communication module such as the body communication module 116, a WLAN communication modem, a Wibro communication modem, an HSDPA communication modem, a Bluetooth communication module, and an infrared communication modem. The devices around may transmit a response message by using the same communication method as the one through which the connection device confirmation message is transmitted, or by using a different communication method from the one through which the connection device confirmation message is transmitted.

The response message may include a device identifier, a device type, owner information, communication capability information, and connection setting information. The device type may be information on whether a device is the headset, a mobile phone, a TV, or a computer. The communication capability information may correspond to information on which one of a plurality of communication methods such as WLAN communication, Wibro communication, HSDPA communication, Bluetooth communication, and infrared communication is supported by a device. The connection setting information may correspond to information necessary for connecting to a supported communication method. According to an embodiment, a device identifier, a device type, owner information, communication capability information, and connection setting information may be transmitted through an additional message separated from a response message.

The control unit 180 of the portable terminal 100 receiving the response message displays a graphical user interface (GUI) supporting various selections on the display unit 151, and receives a user input if necessary in operation S131. The GUI according to various embodiments will be described with reference to FIGS. 41 to 45.

Figure 41:
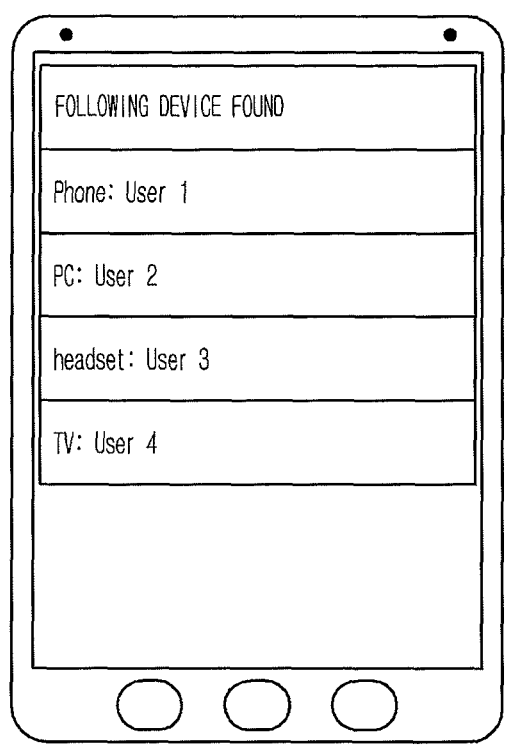
FIG. 41 is view illustrating GUI for connection device selection according to an embodiment.

FIG. 41 is view illustrating GUI for selecting a device to be connected according to an embodiment.

As shown in FIG. 41, the control unit 180 displays a searched device list on the display unit 151, and provides selection for device connection to a user. Each item of the displayed list may include at least one of a device identifier, a device type, owner information, communication capability information, and connection setting information.

According to an embodiment, if the number of the searched devices is one, the control unit 180 may not display the searched device list. According to an embodiment, the control unit 180 may select a device for connection without user's selection on the basis of types of events and files to be transmitted instead of not displaying the searched device list. When control unit 180 detects event occurrence and a connection device is selected, displaying the GUI for selecting a device to be connected may not be omitted.

Figure 42:
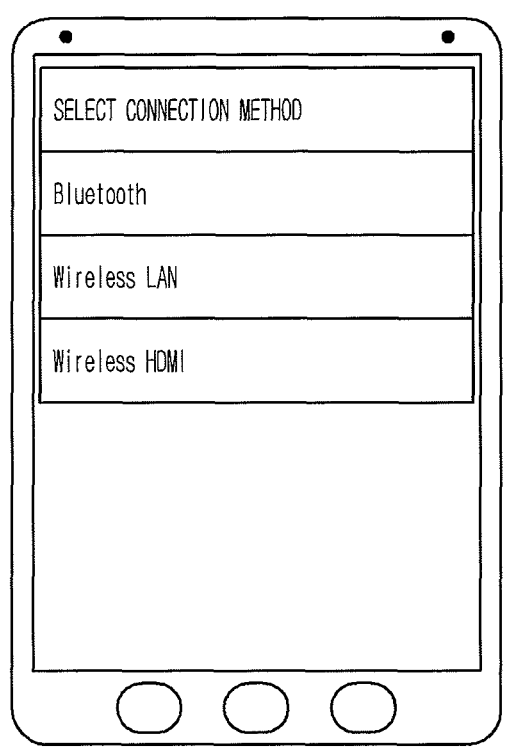
FIG. 42 is view illustrating GUI for selecting a device to be connected according to an embodiment.

FIG. 42 is view illustrating GUI for selecting a device to be connected according to an embodiment.

As shown in FIG. 42, the control unit 180 displays on the display unit 151 a list of a common connection type among a connection type that the selected device supports and a connection type that the portable terminal 100 supports, and provides selection for connection type to a user. Especially, the control unit 180 determines required quality of service (QoS) on the basis of types of events and files to be transmitted, and displays on the display unit 151 a list of a connection type that satisfies QoS, which is determined from the common connection type. When control unit 180 detects event occurrence and a connection type is selected, displaying the GUI to select a connection type may be omitted.

Figure 43:
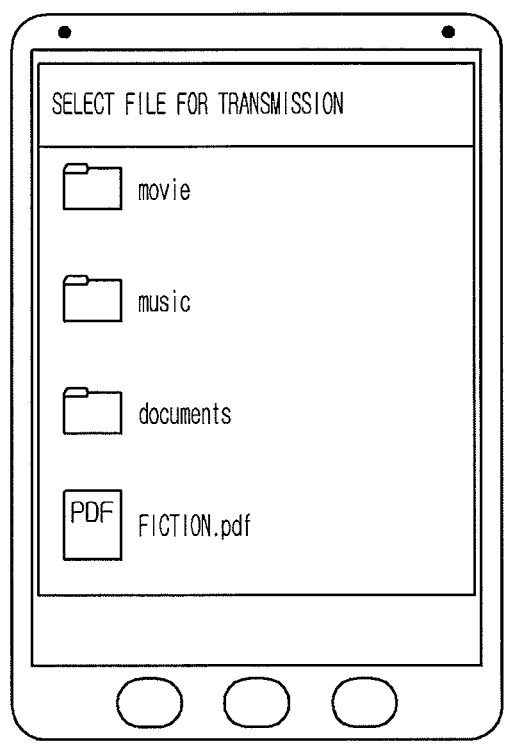
FIG. 43 is view illustrating GUI for file selection according to an embodiment.

FIG. 43 is view illustrating GUI for file selection according to an embodiment.

As shown in FIG. 43, the control unit 180 displays an icon of at least one file on the display unit 151, and provides selection for a file to be transmitted to a user. When control unit 180 detects event occurrence and a file to be transmitted is selected, displaying the GUI for file selection may be omitted.

Figure 44:
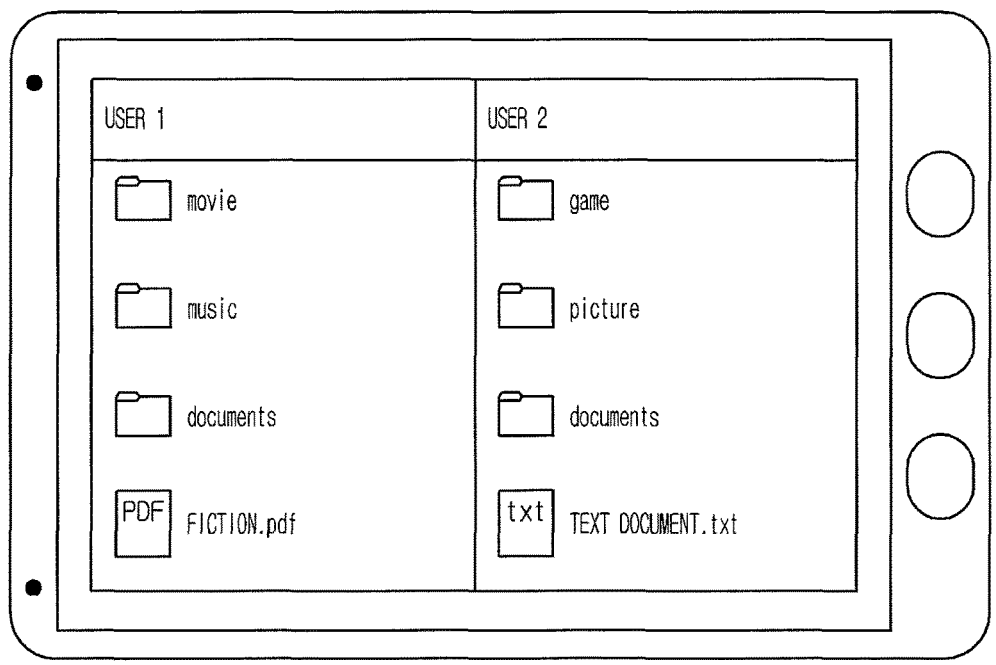
FIG. 44 is view illustrating GUI for file selection according to another embodiment.

FIG. 44 is view illustrating GUI for file selection according to another embodiment.

As shown in FIG. 44, the control unit 180 displays the GUI including a first region that displays a transmission available file list that the portable terminal 100 has and a second region that displays a transmission available file list that a connected device has. When a file in the first region is dragged on the second region, the control unit 180 may transmits the dragged file to a device through a selected connection type. When a file in the second region is dragged on the first region, the control unit 180 may receive the dragged file from the connected device through a selected connection type.

Figure 45:
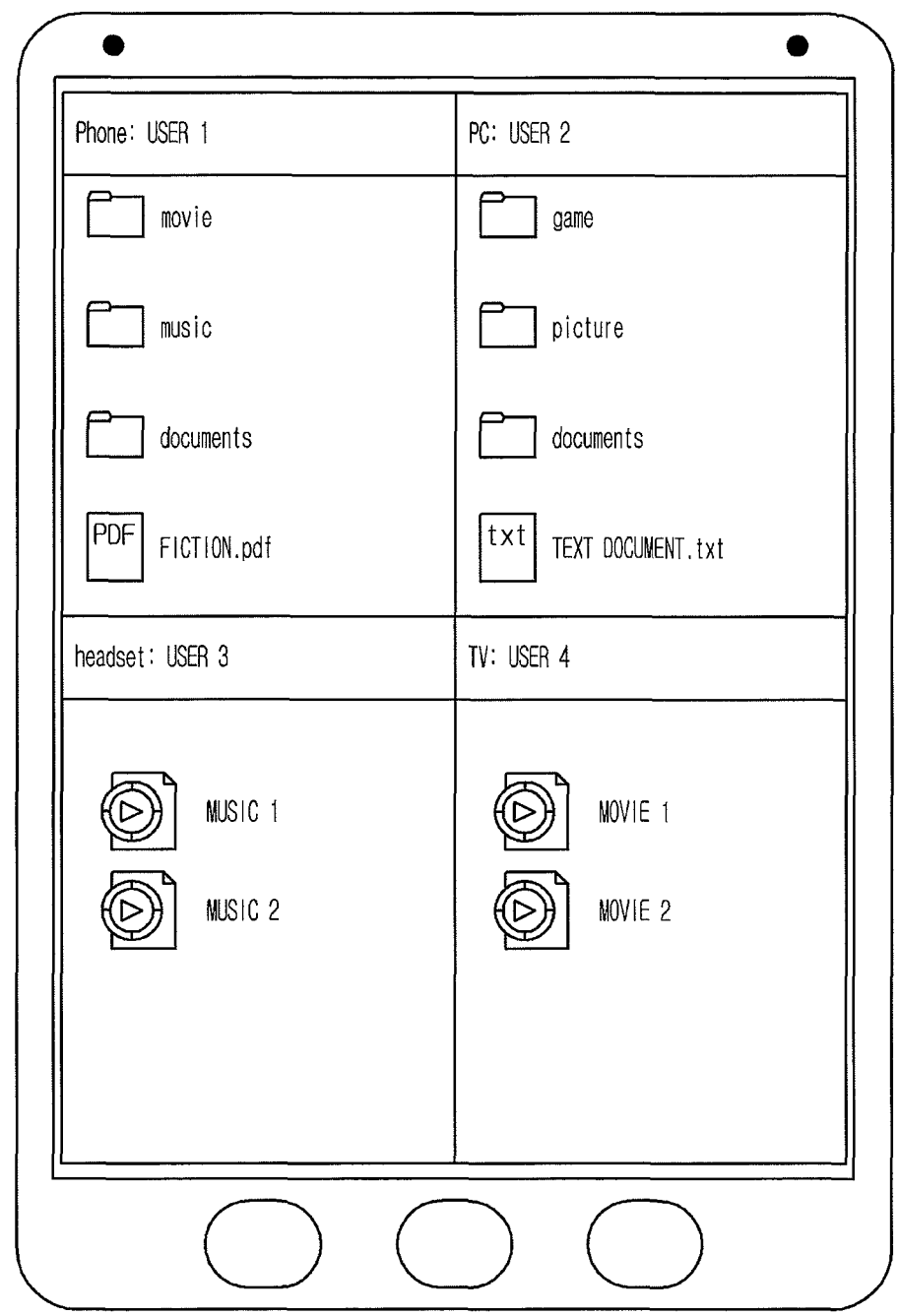
FIG. 45 is view illustrating GUI according to an embodiment.

FIG. 45 is view illustrating GUI according to an embodiment.

The GUI shown in FIG. 45 includes a plurality of regions, which correspond to a plurality of searched devices, respectively. Each region includes GUI for controlling a corresponding device. That is, GUI for connection type selection, GUI for transmission file selection, and GUI for volume adjustment may be provided to each region.

FIG. 39 is described again.

The control unit 180 determines required QoS on the basis of types of events and files to be transmitted, and selects a connection type that satisfies QoS in operation S133 in order to provide user convenience.

The control unit 180 provides a communication preparation command message to the first device 400, i.e. the selected device, in operation S135. The control unit 180 may output the communication preparation command message to the two ECG electrodes 171 through the body communication module 116. When a connection type is selected, the control unit 180 may provide the communication preparation command message to the selected device through a communication module for the selected connection type.

Once the communication preparation command message is received, the first device 400 prepares communication in operation S137. The communication preparation command message may include information on the selected connection type. In this case, the first device 400 may turn on a communication module for the selected connection type.

Then, the control unit 180 of the portable terminal 100 performs communication with the selected device, i.e. the first device 400, through the communication module for the selected communication method in operation S139.

According to an embodiment, operation S101 may correspond to the second mode M2; operation S103 may correspond to the third mode M3; operations S105 to operation S117 may correspond to the fourth mode M4; and operations S121 to S139 may correspond to the fifth mode M5.

According to another embodiment, operation S101 may correspond to the second mode M2; operation S103 may correspond to the third mode M3; operations S105 to operation S117 may correspond to the fourth mode M4; operations S121 to S129 may correspond to the second mode M2; operations S131 and S133 may correspond to the third mode M3; and operations S135 to S139 may correspond to the fifth mode M5. At this point, in the third mode M3, the control unit 180 provides recommendation on a communication target, a communication method, and transmission files, and changes into the next mode after detecting an EMG waveform. Moreover, the forth mode M4 may be added between operation S133 and operation S135.

Then, usage cases according to an embodiment will be described with reference to FIGS. 46 to 52.

Figure 46:
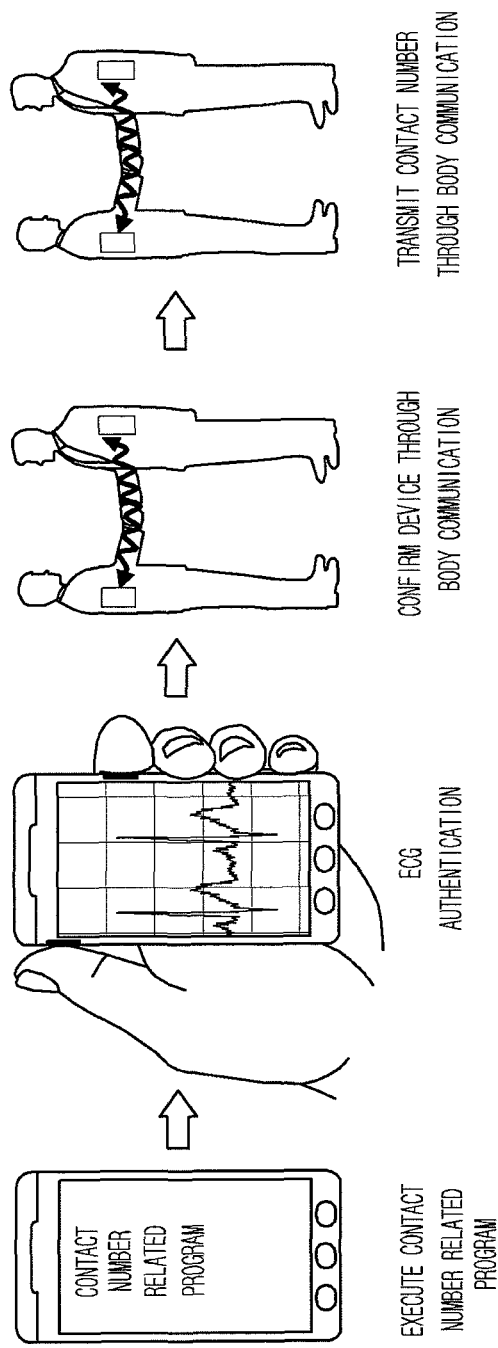
FIG. 46 is a view illustrating a process for transmitting a contact number to a mobile phone at the other side according to an embodiment.

FIG. 46 is a view illustrating a process for transmitting a contact number to the other side's mobile phone according to an embodiment.

As shown in FIG. 46, once a contact number related program is executed, it waits for ECG authentication. When the user's hand contacts the two ECG electrodes 171, the contact number related program or an ECG authentication program related thereto performs ECG authentication. Then, when the user shakes hands with the other side, the contact number related program confirms the other side's mobile phone by using the two ECG electrodes 171 through a body communication method. Once the other side's mobile phone is confirmed, the contact number related program exchanges a contact number with the other side's mobile phone by using the two ECG electrodes 171 through a body communication method.

Figure 47:
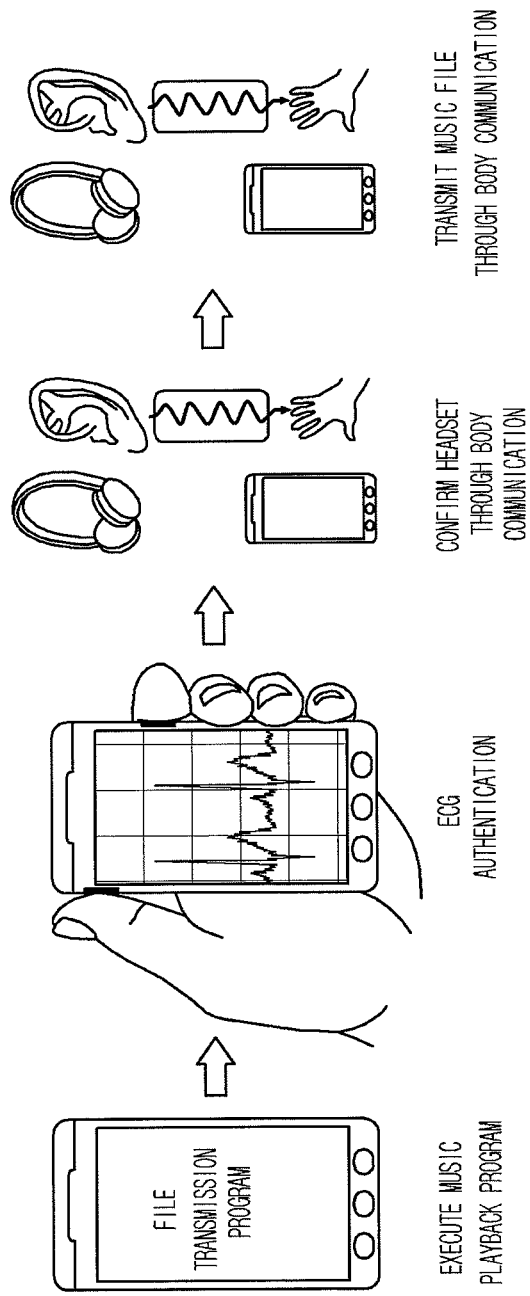
FIG. 47 is a view illustrating a process for listening to music according to an embodiment.

FIG. 47 is a view illustrating a process for listening to music according to an embodiment.

As shown in FIG. 47, once a music playback program is executed, it waits for ECG authentication. When the user's hand contacts the two ECG electrodes 171, the music playback program or an ECG authentication program related thereto performs ECG authentication. Then, the music playback program confirms the headset by using the two ECG electrodes 171 through a body communication method. Once the headset is confirmed, the music playback program transmits music to the headset by using the two ECG electrodes 171 through a body communication method.

Figure 48:
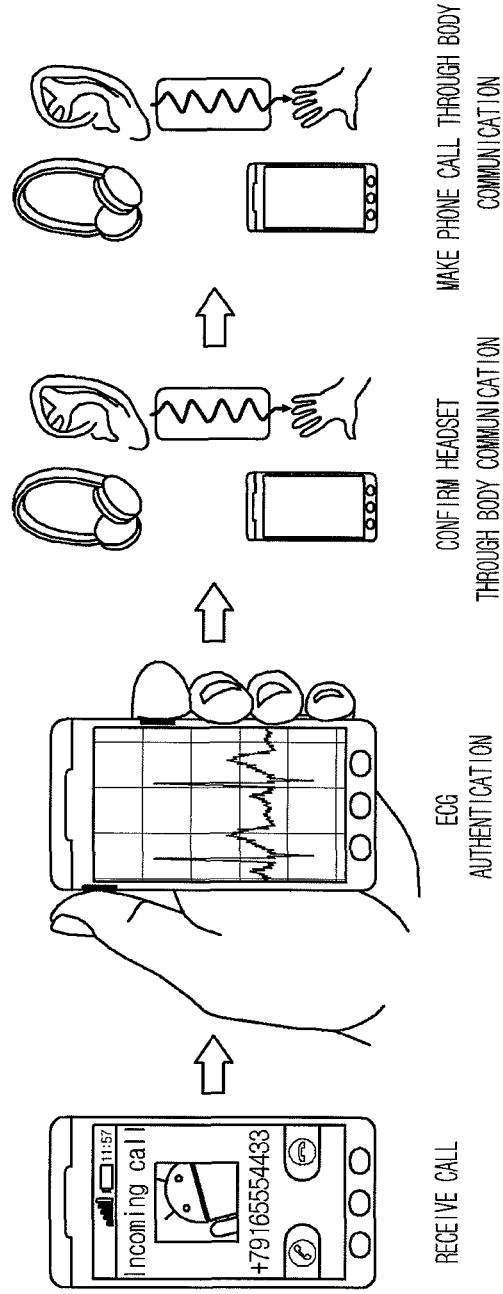
FIG. 48 is view illustrating a process for phone call according to an embodiment.

FIG. 48 is view illustrating a process for phone call according to an embodiment.

As shown in FIG. 48, when a mobile phone receives a call, a phone call program notifies a call reception to a user through bell sound or vibration, and waits for ECG authentication. When the user's hand contacts the two ECG electrodes 171, the phone call program or an ECG authentication program related thereto performs ECG authentication. Then, the phone call program confirms the headset by using the two ECG electrodes 171 through a body communication method. Once the headset is confirmed, the phone call program transmits the other side's voice to the headset by using the two ECG electrodes 171 through a body communication method, and receives a user's voice from the headset.

Figure 49:
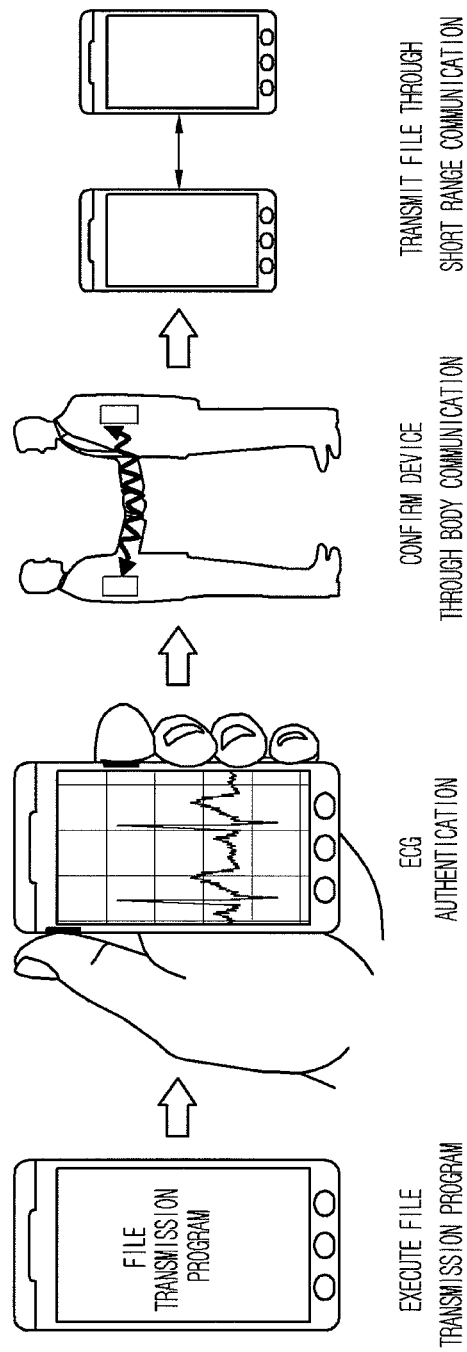
FIG. 49 is a view illustrating a process for transmitting a security file to the other side's mobile phone according to an embodiment.

FIG. 49 is a view illustrating a process for transmitting a security file to the other side's mobile phone according to an embodiment.

As shown in FIG. 49, once a file transmission program is executed, it waits for ECG authentication. When the user's hand contacts the two ECG electrodes 171, the file transmission program or an ECG authentication program related thereto performs ECG authentication. Then, when the user shakes hands with the other side, the file transmission program confirms the other side's mobile phone by using the two ECG electrodes 171 through a body communication method. Once the other side's mobile phone is confirmed, the file transmission program determines a communication method on the basis of the size of the security file. If the size of the security file is too large and thus a body communication method cannot be used, the file transmission program transmits the security file to the other side's mobile phone through a short range communication method.

Figure 50:
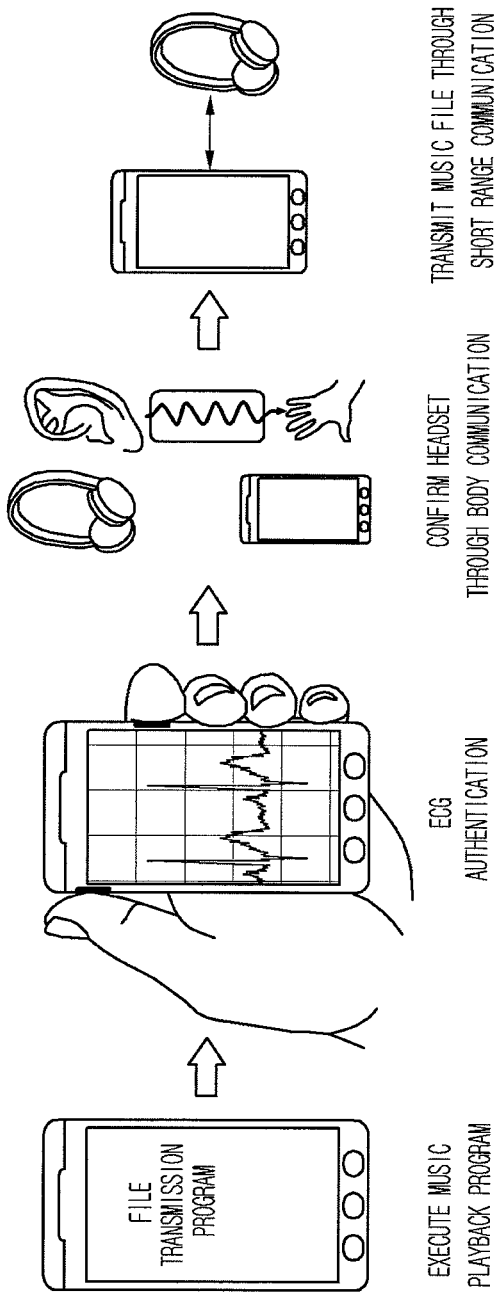
FIG. 50 is a view illustrating a process for listening to music according to an embodiment.

FIG. 50 is a view illustrating a process for listening to music according to an embodiment.

As shown in FIG. 50, once a music playback program is executed, it waits for ECG authentication. When the user's hand contacts the two ECG electrodes 171, the music playback program or an ECG authentication program related thereto performs ECG authentication. Then, the music playback program confirms the headset by using the two ECG electrodes 171 through a body communication method. According to an embodiment, the music playback program may confirm the headset through a Bluetooth communication method. If a user wants to listen to high-quality music or wants to put down the mobile phone, the music playback program transmits music to the headset through a short range communication method such as a Bluetooth communication method.

Figure 51:
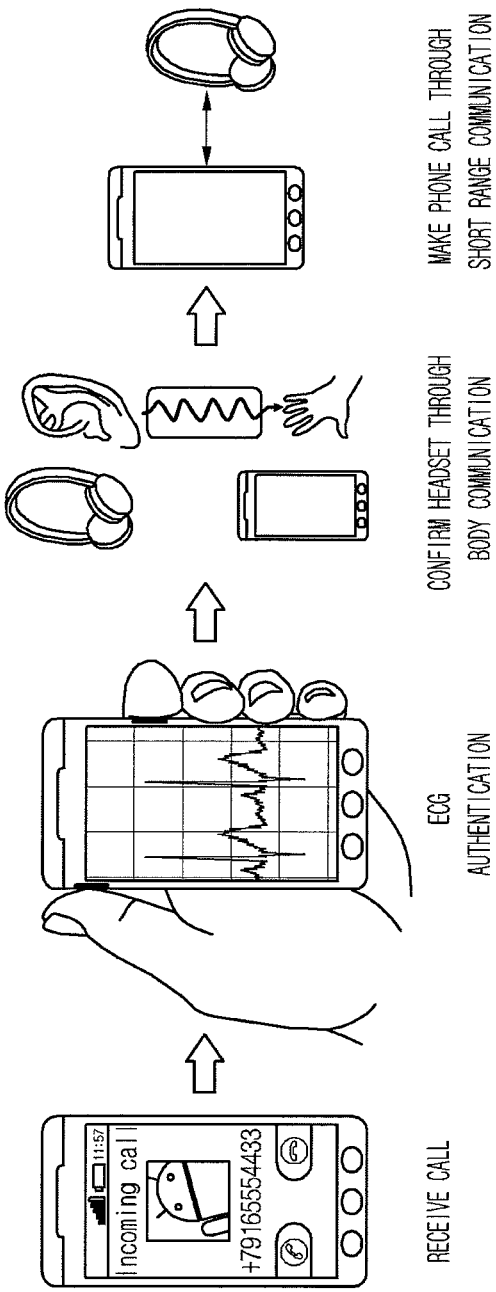
FIG. 51 is view illustrating a process for phone call according to an embodiment.

FIG. 51 is view illustrating a process for phone call according to an embodiment.

As shown in FIG. 51, when a mobile phone receives a call, a phone call program notifies a call reception to a user through bell sound or vibration, and waits for ECG authentication. When the user's hand contacts the two ECG electrodes 171, the phone call program or an ECG authentication program related thereto performs ECG authentication. Then, the phone call program confirms the headset by using the two ECG electrodes 171 through a body communication method. According to an embodiment, the music playback program may confirm the headset through a Bluetooth communication method. If a user wants to put down the mobile phone, the music playback program transmits the other side' voice to the headset through a short range communication method such as a Bluetooth communication method, and receives a user's voice from the headset.

Figure 52:
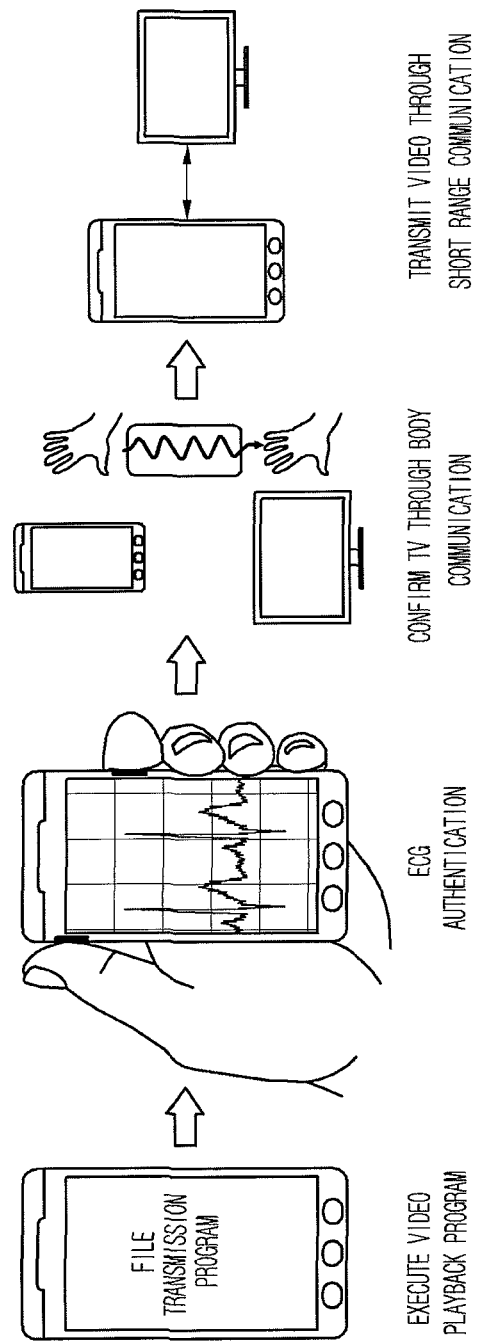
FIG. 52 is a view illustrating a process for watching a video according to an embodiment.

FIG. 52 is a view illustrating a process for watching a video according to an embodiment.

As shown in FIG. 52, once a video playback program is executed, it waits for ECG authentication. When the user's hand contacts the two ECG electrodes 171, the video playback program or an ECG authentication program related thereto performs ECG authentication. Then, the video playback program confirms a TV or a monitor by using the two ECG electrodes 171 through a body communication method. According to an embodiment, the video playback program may confirm a TV through a wireless LAN method, wireless High-Definition Multimedia Interface (HDMI), and a Bluetooth communication method. Since video transmission requires a large bandwidth, the video playback program transmits a video to a TV through a communication method having a large bandwidth such as wireless HDMI.

According to various embodiments of the present invention, a user can control various functions of a terminal through a signal obtained from a body without an external input device such as a keyboard or a mouse.

Even if a user intentionally does not try to measure an electrocardiogram (ECG) signal, a mobile/portable terminal according to embodiments of the present invention can measure an ECG signal automatically during a call or listening to music. Moreover, power consumed for measuring an ECG signal may be reduced in a mobile/portable terminal.

The above method can also be embodied as computer readable codes on a computer readable recording medium. Examples of the computer readable recording medium include read-only memory (ROM), random-access memory (RAM), CD-ROMs, magnetic tapes, floppy disks, and optical data storage devices. The method can also be embodied as carrier waves (such as data transmission through the Internet).

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A user terminal device comprising:
an ear accessory of the user terminal device including:
a first electrocardiogram (ECG) electrode contacted with an ear of a user,
a second ECG electrode contacted with a hand of the user, and
a first speaker configured to output an audio signal;
a display; and
a controller configured to:
display, on the display, bio information based on a first ECG signal from the first ECG electrode when the ear of the user is contacted with the first ECG electrode,
control an audio playback in response to a second ECG signal from the second ECG electrode when the hand of the user is contacted with the second ECG electrode,
receive the second ECG signal from the second ECG electrode when the hand of the user is contacted with the second ECG electrode,
determine a contact type of a user hand with the second ECG electrode, and
control the audio playback according to the contact type of the user hand.

2. The user terminal device according to claim 1, wherein the bio information includes a result of an ECG measurement.

3. The user terminal device according to claim 1, further comprising:
an ECG sensor configured to generate the first ECG signal through the first ECG electrode and the second ECG signal through the ECG electrode, respectively.

4. The user terminal device according to claim 1, wherein the ear accessory further includes:
an ECG sensor configured to generate the first ECG signal through the first ECG electrode and the second ECG signal through the ECG electrode, respectively.

5. The user terminal device according to claim 1, further comprising:
a second speaker,
wherein when the audio signal is being output through the second speaker and the ear of the user is contacted with the first ECG electrode, the controller is configured to pause an output of the audio signal through the second speaker and control the audio signal to output through the first speaker.

6. The user terminal device according to claim 1, wherein the controller is configured to output the audio signal through the first speaker in response to an execution of an audio application when the ear accessory is worn.

7. The user terminal device according to claim 6, wherein the controller is configured to pause an output of the audio signal through the first speaker and control the audio signal to output through the second speaker when the ear accessory is taken off.

8. The user terminal device according to claim 1, wherein the controller is configured to display, on the display, the bio information from the first ECG electrode in response to an execution of a bio application.

9. The user terminal device according to claim 8, wherein at the same time, the controller is configured to control the audio signal through the first speaker.

10. A method of controlling a user terminal device, the user terminal device including an ear accessory of the user terminal device, a second speaker and a display, the ear accessory including a first electrocardiogram (ECG) electrode contacted with an ear of a user, a second ECG electrode contacted with a hand of the user, and a first speaker configured to output an audio signal, the method comprising:

detecting if the ear accessory is worn;
displaying, on the display, bio information based on a first ECG signal from the first ECG electrode when the ear of the user is contacted with the first ECG electrode;
controlling an audio playback in response to a second ECG signal from the second ECG electrode when the hand of the user is contacted with the second ECG electrode;
receiving the second ECG signal from the second ECG electrode when the hand of the user is contacted with the second ECG electrode;
determining a contact type of a user hand with the second ECG electrode; and
controlling the audio playback according to the contact type of the user hand.

11. The method according to claim 10, wherein the bio information includes a result of an ECG measurement.

12. The method according to claim 10, wherein when the audio signal is being output through the second speaker and the ear of the user is contacted with the first ECG electrode, pausing an output of the audio signal through the second speaker and controlling the audio signal to output through the first speaker.

13. The method according to claim 10, further comprising:
outputting the audio signal through the first speaker in response to an execution of an audio application when the ear accessory is worn.

14. The method according to claim 13, further comprising:
pausing an output of the audio signal through the first speaker and controlling the audio signal to output through the second speaker when the ear accessory is taken off.

15. The method according to claim 10, further comprising:
displaying, on the display, the bio information from the first ECG electrode in response to an execution of a bio application.

16. The method according to claim 15, further comprising:
at the same time, controlling the audio signal through the first speaker.

* * * * *